(12) United States Patent
Hedrick et al.

(10) Patent No.: US 11,124,565 B2
(45) Date of Patent: *Sep. 21, 2021

(54) METHOD FOR TREATING PRE-TYPE 1 DIABETES IN A HUMAN SUBJECT

(71) Applicant: Janssen Biotech, Inc., Horsham, PA (US)

(72) Inventors: Joseph Hedrick, New Hope, PA (US); Elizabeth C. Hsia, Kenneth Square, PA (US); Paul Imm, Newtown, PA (US); Jocelyn Leu, Ambler, PA (US); Bethany Paxson, Philadelphia, PA (US); Mark Rigby, Abington, PA (US); Songmao Zheng, Ambler, PA (US); Ramineh Zoka, Lower Gwynedd, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,388

(22) Filed: Aug. 14, 2019

(65) Prior Publication Data

US 2019/0375836 A1    Dec. 12, 2019

Related U.S. Application Data

(62) Division of application No. 15/421,473, filed on Feb. 1, 2017, now Pat. No. 10,465,003.

(60) Provisional application No. 62/291,673, filed on Feb. 5, 2016.

(51) Int. Cl.
| | |
|---|---|
| *C07K 16/24* | (2006.01) |
| *A61P 3/10* | (2006.01) |
| *A61P 29/00* | (2006.01) |
| *A61M 5/00* | (2006.01) |
| *A61M 5/315* | (2006.01) |
| *A61K 39/00* | (2006.01) |

(52) U.S. Cl.
CPC ........... *C07K 16/241* (2013.01); *A61M 5/003* (2013.01); *A61M 5/31533* (2013.01); *A61M 5/31573* (2013.01); *A61M 5/31591* (2013.01); *A61P 3/10* (2018.01); *A61P 29/00* (2018.01); *A61K 2039/505* (2013.01); *A61K 2039/545* (2013.01); *C07K 2317/21* (2013.01); *C07K 2317/565* (2013.01)

(58) Field of Classification Search
CPC .......................... C07K 16/241; C07K 2317/10
See application file for complete search history.

(56) References Cited

U.S. PATENT DOCUMENTS

| | | |
|---|---|---|
| 4,603,106 A | 7/1986 | Cerami et al. |
| 4,816,567 A | 3/1989 | Cabilly et al. |
| 4,822,776 A | 4/1989 | Cerami et al. |
| 4,873,316 A | 10/1989 | Meade et al. |
| 5,075,236 A | 12/1991 | Yone et al. |
| 5,223,395 A | 6/1993 | Gero |
| 5,231,024 A | 7/1993 | Moeller et al. |
| 5,304,489 A | 4/1994 | Rosen |
| 5,342,613 A | 8/1994 | Creaven et al. |
| 5,360,716 A | 11/1994 | Ohmoto et al. |
| 5,436,154 A | 7/1995 | Barbanti et al. |
| 5,565,362 A | 10/1996 | Rosen |
| 5,654,407 A | 8/1997 | Boyle et al. |
| 5,658,570 A | 8/1997 | Newman et al. |
| 5,656,272 A | 12/1997 | Le et al. |
| 5,698,195 A | 12/1997 | Le et al. |
| 5,698,419 A | 12/1997 | Wolpe et al. |
| 5,700,788 A | 12/1997 | Mongelli et al. |
| 5,730,975 A | 3/1998 | Hotamisligil et al. |
| 5,741,488 A | 4/1998 | Feldman et al. |
| 5,750,105 A | 5/1998 | Newman et al. |
| 5,776,947 A | 7/1998 | Koremer et al. |
| 5,827,690 A | 10/1998 | Meade et al. |
| 5,849,992 A | 12/1998 | Meade et al. |
| 5,888,511 A | 3/1999 | Skurkovich et al. |
| 5,919,452 A | 7/1999 | Le et al. |
| 5,958,413 A | 9/1999 | Anagnostopulos et al. |
| 5,959,087 A | 9/1999 | Rathjen et al. |
| 5,993,833 A | 11/1999 | DeLacharriere et al. |
| 5,994,616 A | 11/1999 | Rosen |
| 6,015,558 A | 1/2000 | Hotamisligil et al. |
| 6,172,202 B1 | 1/2001 | Marcucci et al. |
| 6,190,691 B1 | 2/2001 | Mak |
| 6,194,451 B1 | 2/2001 | Aplegiani et al. |
| 6,277,969 B1 | 8/2001 | Le et al. |
| 6,284,471 B1 | 9/2001 | Le et al. |

(Continued)

FOREIGN PATENT DOCUMENTS

| | | |
|---|---|---|
| AU | 668864 B2 | 10/1992 |
| AU | 17649/92 | 5/1996 |
| EP | 0212489 B1 | 3/1987 |
| EP | 0218868 A2 | 4/1987 |
| EP | 0260610 B1 | 3/1988 |
| EP | 0288088 B1 | 10/1988 |
| EP | 0308378 B1 | 3/1989 |
| EP | 0350690 A2 | 1/1990 |
| EP | 0351789 B1 | 1/1990 |
| EP | 0380068 A1 | 8/1990 |

(Continued)

OTHER PUBLICATIONS

Beutler, B. et al., "Identity of tumour necrosis factor and the macrophage-secreted factor cachectin," *Nature*, 316:552-554 (1985).

(Continued)

*Primary Examiner* — Gyan Chandra
(74) *Attorney, Agent, or Firm* — Riverside Law LLP

(57) ABSTRACT

The present invention relates to compositions and methods utilizing anti-TNF antibodies having a heavy chain (HC) comprising SEQ ID NO:36 and a light chain (LC) comprising SEQ ID NO:37 for use in the treatment or prevention of Type I Diabetes (T1D).

8 Claims, 25 Drawing Sheets
(6 of 25 Drawing Sheet(s) Filed in Color)
Specification includes a Sequence Listing.

(56) References Cited

U.S. PATENT DOCUMENTS

| | | | |
|---|---|---|---|
| 6,309,640 | B1 | 10/2001 | Cerami et al. |
| 6,419,927 | B1 | 7/2002 | Cerami et al. |
| 6,790,444 | B2 | 9/2004 | Junming et al. |
| 6,835,823 | B2 | 12/2004 | Junming et al. |
| 6,991,791 | B2 | 1/2006 | Junming et al. |
| 7,070,775 | B2 | 7/2006 | Junming et al. |
| 7,101,674 | B2 | 9/2006 | Junming et al. |
| 7,128,907 | B2 | 10/2006 | Le et al. |
| 7,192,584 | B2 | 3/2007 | Le et al. |
| 7,250,165 | B2 | 7/2007 | Heavner et al. |
| 7,521,206 | B2 | 4/2009 | Heavner et al. |
| 7,691,378 | B2 | 4/2010 | Heavner et al. |
| 8,241,899 | B2 | 8/2012 | Heavner et al. |
| 8,889,136 | B2 | 11/2014 | Hoffman |
| 2006/0009385 | A1 | 1/2006 | Hoffman |
| 2009/0214528 | A1 | 8/2009 | Dorai |

FOREIGN PATENT DOCUMENTS

| | | |
|---|---|---|
| EP | 0393438 A2 | 10/1990 |
| EP | 0398327 B1 | 11/1990 |
| EP | 0412486 B1 | 2/1991 |
| EP | 0486526 B2 | 3/1991 |
| EP | 0433900 A1 | 6/1991 |
| EP | 0453898 A2 | 10/1991 |
| EP | 0 526 905 A2 | 8/1992 |
| EP | 0512528 B1 | 11/1992 |
| EP | 0 525 570 A2 | 2/1993 |
| EP | 0585705 B1 | 3/1994 |
| EP | 0614984 B1 | 9/1994 |
| EP | 0101681 B1 | 12/1994 |
| EP | 0663836 B1 | 7/1997 |
| EP | 0 610 201 B1 | 5/2001 |
| JP | 61-047500 B2 | 3/1986 |
| JP | 02-227095 A1 | 9/1990 |
| JP | 11127855 A | 10/1997 |
| JP | 2004523209 | 8/2004 |
| JP | 2009508476 | 3/2009 |
| WO | WO 89/08460 A1 | 9/1989 |
| WO | WO 90/00902 A1 | 2/1990 |
| WO | WO 90/09150 A1 | 3/1990 |
| WO | WO 91/02078 A1 | 2/1991 |
| WO | WO 91/04054 A1 | 4/1991 |
| WO | WO 91/09967 A1 | 7/1991 |
| WO | WO 92/01059 A1 | 1/1992 |
| WO | WO 92/01472 A1 | 2/1992 |
| WO | WO 92/07076 A | 4/1992 |
| WO | WO 92/11383 A1 | 7/1992 |
| WO | WO 92/13095 A1 | 8/1992 |
| WO | WO 92/16553 A1 | 10/1992 |
| WO | WO 93/02108 A1 | 2/1993 |
| WO | WO 93/11383 A1 | 2/1993 |
| WO | WO 93/11236 A1 | 6/1993 |
| WO | WO 94/08609 A1 | 4/1994 |
| WO | WO 94/08619 A1 | 4/1994 |
| WO | WO 96/33735 A1 | 10/1996 |
| WO | WO 97/29131 A1 | 8/1997 |
| WO | 2002012502 | 2/2002 |
| WO | WO 02/12502 A2 | 2/2002 |
| WO | WO 03/083061 A2 | 10/2003 |
| WO | 2007028106 | 3/2007 |

OTHER PUBLICATIONS

Beutler, B. et al., "Passive Immunization Against Cachectin/Tumor Necrosis Factor Protects Mice from Lethal Effect of Endotoxin," *Science*, 229:869-871 (1985).

Morrison, Sherie L., "Transfectomas Provide Novel Chimeric Antibodies," *Science*, 229:1202-1207 (1985).

Aggarwali, Bharat B. et al., "Human Tumor Necrosis Factor Production, Purification and Characterization," *J. of Biol. Chem.*, 260(4):2345-2354 (1985).

Beutler, B. et al., "Purification of Cachectin, A Lipoprotein Lipase-Suppressing Hormone Secreted by Endotoxin-induced RAW 264.7 Cells," *J. Exp. Med.*, 161:984-995 (1985).

Paulus, H., "A Preparation and Biomedical Applications of Bispecific Antibodies", *Behring Inst. Mitt*, No. 78:118-132 (1985).

Hayashi, H. et al., "An Enzyme-linked Immunosorbent Assay for Recombinant Human Tumor Necrosis Factor Using Monoclonal Antibody," *Recent Adv. Chemother*, 820-821 (1985).

Liang, Chi-Ming et al., "Production and Characterization of Monoclonal Antibodies Against Recombinant Human Tumor Necrosis Factor/Cachectin," *Biochem. & Biophy. Res. Comm.*, 137(2):847-854 (1986).

Hirai, Makoto et al., "Production and characterization of monoclonal antibodies to human tumor necrosis factor," *J. of Immun. Methods*, 96:57-62 (1987).

Piguet, Pierre-Francois et al., "Tumor Necrosis Factor/Cachectin is an Effector of Skin and Gut Lesions of the Acute Phase of Graft-vs.-Host Disease," *J. Exp. Med.*, 166:1280-1289 (1987).

Meager, Anthony et al., "Preparation and Characterization of Monoclonal Antibodies Directed Against Antigenic Determinants of Recombinant Human Tumour Necrosis Factor (rTNF)," *Hybridoma*, 6(3):305-311 (1987).

Fendly, Brian M. et al., "Murine Monoclonal Antibodies Defining Neutralizing Epitopes on Tumor Necrosis Factor," *Hybridoma*, 6(4):359-370 (1987).

Bringman, Timothy S. and Aggarwal, Bharat B., "Monoclonal Antibodies to Human Tumor Necrosis Factors Alpha and Beta: Applications for Affinity Purification, Immunoassays, and as Structural Probes," *Hybridoma*, 6(5):489-507 (1987).

Tracey, Kevin J. et al., "Anti-cachectin/TNF monoclonal antibodies prevent septic shock during lethal bacteraemia," *Nature*, 330:662-664 (1987).

Nagai, M. et al., "Antibody to tumor necrosis factor (TNF) reduces endotoxin fever," *Experientia*, 44:606-607 (1988).

Shimamoto, Yoshinori et al., "Monoclonal antibodies against human recombinant tumor necrosis factor: prevention of endotoxic shock," *Immunology Letters*, 17:311-318 (1988).

Di Giovine, Francesco, S. et al., "Tumour necrosis factor in synovial exudates," *Annals of the Rheumatic Diseases*, 47:768-772 (1988).

Sunahara, N. et al., "Simple enzyme immunoassay methods for recombinant human tumor necrosis factor [ and its antibodies using a bacterial cell wall carrier," *J Immunol Methods*, 109:203-214 (1988).

Exley, A.R. et al., "Monoclonal Antibody (Mab) to Recombinant Human Tumour Necrosis Factor (rhTNF) in the Prophylaxis and Treatment of Endotoxic Shock in Cynomolgus Monkeys," *Medical Research Society*, Abstract 184, p. 50 (1989).

Cross, A.S. et al., "Pretreatment with Recombinant Murine Tumor Necrosis Factor α Cachectin and Murine Interleukin 1 α Protects Mice from Lethal Bacterial Infection," *J of Exp Med.*, 169:2021-2027 (1989).

Whittle, Nigel, et al., "Construction and Expression of a CDR-Grafted Anti-TNF Antibody," *J. Cell Biochem*, Supl. 13A:96 (1989).

Duncombe, Andrew S. et al., "Tumor Necrosis Factor Mediates Autocrine Growth Inhibition in a Chronic Leukemia," *J Immunol*, 143:3828-3834 (1989).

Aderka, Dan et al., "IL-6 Inhibits Lipopolysaccharide-Induced tumor Necrosis Factor Production in Cultured Human Monocytes, U937 Cells, and in Mice," *J Immunol*, 143:3517-3523 (1989).

Eck, Michael J. and Sprang, Stephen R., "The Structure of Tumor Necrosis Factor-a at 2.6 a Resolution," *J Biol Chem*, 264:17595-17605 (1989).

Gillies, Stephen D. et al., "High-level expression of chimeric antibodies using adapted cDNA variable region cassettes," *J Immunol Methods*, 125:191-202 (1989).

Englemann, Hartmut et al., "A Tumor Necrosis Factor-binding Protein Purified to Homogeneity from Human Urine Protects Cells from Tumor Necrosis Factor Toxicity," *J. of Bio. Chem.*, 264(20):11974-11980 (1989).

Kawasaki, Hajime et al., "Analysis of Endotoxin Fever in Rabbits by Using a Monoclonal Antibody to Tumor Necrosis Factor (Cachectin)," *Infection and Immunity*, 57(10):3131-3135 (1989).

(56) References Cited

OTHER PUBLICATIONS

Fong, Yuman et al., "Antibodies to Cachectin/Tumor Necrosis Factor Reduce Interleukin 1β and Interleukin 6 Appearance During Lethal Bacteremia," *J. Exp. Med.*, 170:1627-1633 (1989).
Collins, M.S. et al., "Immunoprophylaxis of Polymicrobic Cellulitis with a Human Monoclonal Antibody Against Lipopolysaccharide Antigen of Pseudomonas aeruginosa," Abstract E-63, *Abstracts of Annual Meeting 1989*.
Kameyama, Koh-zoh, et al., "Convenient plasmid vectors for construction of chimeric mouse/human antibodies," *FEBS Lett*, 244:301-306 (1989).
Genebank Accession, No. N90300 (Nov. 1, 1989).
Engelmann, Hartmut et al., "Two Tumor Necrosis Factor-binding Proteins Purified from Human Urine," *J. of Bio. Chem.*, 265(3):1531-1536 (1990).
Tavernier, Jan et al., "Analysis of the Structure-Function Relationship of Tumour Necrosis Factor. Human/Mouse Chimeric TNF Proteins: General Properties and Epitope Analysis," *J. Mol. Biol.*, 211:493-501 (1990).
Lucas, R. et al., "Generation and characterization of a neutralizing rat anti-rm TNF-α monoclonal antibody," *Immunology*, 71:218-223 (1990).
Hinshaw, L.B. et al., "Survival of Primates in $LD_{100}$ Septic Shock Following Therapy with Antibody to Tumor Necrosis Factor (TNFα)," *Circulatory Shock*, 30:279-292 (1990).
Nophar, Yaron et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *The EMBO Journal*, 9(10):3269-3278 (1990).
Verhoef, J. and Torensma, R., "Prospects for Monoclonal Antibodies in the Diagnosis and Treatment of Bacterial Infections," *Eur. J. Clin. Microbiol. Dis.*, 9(4):247-250 (1990).
Leotscher, Hansruedi et al., "Molecular Cloning and Expression of the Human 55 kd Tumor Necrosis Factor Receptor," *Cell*, 61:351-359 (1990).
Schall, Thomas J. et al., "Molecular Cloning and Expression of a Receptor for Human Tumor Necrosis Factor," *Cell*, 61:361-370 (1990).
Akama, Hideto et al., "Mononuclear Cells Enhance Prostaglandin $E_2$ Production of Polymorphonuclear Leukocytes via Tumor Necrosis Factor α," *Biochemical and Biophysical Research Comm.*, 168(2):857-862 (1990).
Exley, A.R. et al., "Monoclonal antibody to TNF in severe septic shock," *The Lancet*, 335:1275-1277 (1990).
Möller, Achim et al., "Monoclonal Antibodies to Human Tumor Necrosis Factor α: In Vitro and In Vivo Application," *Cytokine*, 2(3):162-169 (1990).
Gorman, S.D. and Clark, M.R., "Humanization of monoclonal antibodies for therapy," *Sem Immunol*, 2:457-466 (1990).
Echtenacher, Bernd et al., "Requirement of Endogenous Tumor Necrosis Factor/Cachectin for Recovery from Experimental Peritonitis," *J. of Immunology*, 145(11):3762-3766 (1990).
Ruddle, Nancy H. et al., "An Antibody to Lymphotoxin and Tumor Necrosis Factor Prevents Transfer of Experimental Allergic Encephalomyelitis," *J. Exp. Med.*, 172:1193-1200 (1990).
Von Asmuth, E.J.U. et al., "Tumour Necrosis Factor Alpha (TNF-α) and Interleukin 6 in a Zymosan-Induced Shock Model," *Scand. J. Immunol.*, 32:313-319 (1990).
Herve, P. et al., "Monoclonal Anti TNF α Antibody for the Treatment of Severe Acute GvHD in Humans," Abstract 3.25, *Lymphoma Res.* 9:591 (1990).
Silva, Ayona T. et al., "Prophylactic and Therapeutic Effects of a Monoclonal Antibody to Tumor Necrosis Factor-α in Experimental Gram-Negative Shock," *J. of Infectious Diseases*, 162:421-427 (1990).
Opal, Steven M. et al., "Efficacy of a Monoclonal Antibody Directed Against Tumor Necrosis Factor in Protecting Neutropenic Rats from Lethal Infection with Pseudomonas aeruginosa," *J. of Infectious Diseases*, 161:1148-1152 (1990).

Fong, Yuman and Lowry, Stephen F., "Tumor Necrosis Factor in the Pathophysiology of Infection and Sepsis," *Clin Immunol Immunopathol*, 55:157-170 (1990).
Starnes, H. Fletcher, Jr., et al., "Anti-IL-6 Monoclonal Antibodies Protect Against Lethal *Escherichia Coli* Infection and Lethal Tumor Necrosis Factor-a Challenge in Mice," *J Immunol*, 145:4185-4191 (1990).
Genebank Accession, No. M32046 (Jun. 15, 1990).
Smith, Craig R., "Human and Chimeric Antibodies to LPS and TNF," 4Abstract, *Endotoxemia & Sepsis Conference* (1991).
Bodmer, Mark, "Humanized Antibodies for Anti-TNF Therapy," Abstract, *Endotoxemia & Sepsis Conference* (1991).
Aderka, Dan, "Role of Tumor Necrosis Factor in the Pathogenesis of Intravascular Coagulopathy of Sepsis: Potential New Therapeutic Implications," *Isr J Med Sci*, 27:52-60 (1991).
Galloway, Cynthia J. et al., "Monoclonal anti-tumor necrosis factor (TNF) antibodies protect mouse and human cells from TNF cytotoxicity," *J. of Immunological Methods*, 140:37-43 (1991).
Waldmann, Thomas A., "Monoclonal Antibodies in Diagnosis and Therapy," *Science*, 252:1657-1662 (1991).
Lassalle, Ph., et al., "Potential Implication of Endothelial Cells in Bronchial Asthma," *Int Arch Allergy Appl Immunol*, 94:233-238 (1991).
Aderka, Dan et al., "The Possible Role of Tumor Necrosis Factor (TNF) and Its Natural Inhibitors, The Soluble-TNF Receptors, In Autoimmune Diseases," *Israel J. Med. Sci.*, 28(2):126-130 (1992).
Pennington, James, "TNF: Therapeutic Target in Patients with Sepsis," *ASM News*, 58(9):479-482 (1992).
Harris, William J. and Emery, Steven, "Therapeutic antibodies—the coming of age," *TBTECH*, 11:42-44 (1993).
Parrillo, Joseph E., "Pathogenetic Mechanisms of Septic Shock," *N.E. Journal of Medicine*, 328(20):1471-1477 (1993).
Mendez, M. et al., "Functional transplant of megabase human immunoglobulin loci recapitulates human antibody response in mice", *Nature Genetics*, vol. 15, No. 2, pp. 146-156 XP02067603 (Feb. 1997).
Stephens, S. et al., "Comprehensive pharmacokinestic of a humanized antibody and analysis of residual anti-idoiotypic responses", *Immunology*, vol. 85, No. 4, pp. 668-674 XP000881488 (Aug. 1995).
Siegal, S. et al., "The mouse/human chimeric momoclonia antibody cA2 neutralizes TNF in vitro and protects transgenic mice from cachexia and TNF lethality in vivo", *Cytokine*, vol. 7, No. 1 pp. 15-25 XP000990566 (Jan. 1995).
Rankin, E. et al., "The therapeutic effects of an engineered human anti-tumour necrosis factor alpha antibody (CDP571) in rheumatoid arthritis", *British Journal of Rheumatology*, vol. 34, No. 4, pp. 334-342, XP000674590 (Apr. 1995).
Mocellin et al., "Tumor necrosis factor, cancer and anticancer therapy", *Cytokine Growth Factor Rev.* Feb. 2005; 16(1) 35-53, Epub Dec. 19, 2004.
Larmonier et al., "The inhibition of TNF-alpha anti-tumoral properties by blocking antibodies promotes tumor growth in a rat model", *Exp. Cell Res*. Mar. 30, 2007; Epub ahead of print; Abstract only.
Scott et al., "An Anti-Tumor Necrosis Factor-a Antibody Inhibits the Development of Experimental Skin Tumors", *Mol. Can Therapy*, May 2003, 2:445-451.
Berkow et al., "The Merck Manual of Diagnosis and Therapy", Sixteenth Edition, Merck Research Laboratories, Rahway, NJ 1992 p. 1263-1287.
"Carcinoma", *Steadman' Medical Dictionary*, $27^{th}$ Ed. 2000 Lippincott Williams & Wilkins.
Rudikoff et al., Single amino acid substitution altering antigen-binding specificity, *PNAS*, Mar. 1982, vol. 79, p. 1979-83.
Stone et al., "Solid malignancies among patients in the Wegener's Granulomatosis Etanercept Trial", *Arthritis Rheum*. May 2006 ; 54(5) 1608-18 abstract only.
Green, L. "Antibody engineering via genetic engineering of the mouse: Xenomouse strains are a vehicle for the facile generation of therapeutic human monoclonal antibodies", *Journal of Immunological Methods*, 231, pp. 11-23 (1999).

(56) References Cited

OTHER PUBLICATIONS

Hoogenboom, H. et al., "By-passing immunization. Human antibodies from synthetic repertoires of germline VH gene segments rearranged in vitro", *Journal of Molecular Biology*, vol. 227, No. 2, XP024020530; p. 386 (Sep. 10, 1992).

Barone et al., "Tumor Necrosis Factor-a: A Mediator of Focal Ischemic Brain Injury", *Stroke*. vol. 28, pp. 1233-1244 (1997).

Himmerich et al., "Depression, comorbidities and the TNF-a system", *European Psychiatry*, vol. 23, pp. 421-429 (2008).

Bard et al., "Peripherally administered antibodies against amyloid B-peptide enter the central nervous system and reduce pathology in a mouse model of Alzheimer disease", *Nature Medicine*, vol. 6, No. 8, pp. 916-919 (2000).

Pardride, W., "Biopharmaceutical drug targeting to the brain", *Journal of Drug Targeting*, 18(3):157-167, 2010.

Takahashi et al., "An anti-tumor necrosis factor antibody suppresses sleep in rats and rabbits", *Brain Research*, 690: p. 241-244, 1994.

Holsboer-Trachsler et al., "Sleep in Depression and Sleep Deprivation: A Brief Conceptual Review", *World J. Biol. Psychiatry*, 1(4):180-186, 2000.

Van Oosten et al., "Increased MRI activity and immune activation in two multiple sclerosis patients treated with the monoclonal anti-tumor necrosis factor antibody cA2", *Neurology*, 47; 1531-1534, 1996.

De Mattos et al., "Peripheral anti-Aß antibody alters CNS and plasma Aß clearance and decreases brain Aß burden in a mouse model of Alzheimer's Disease", *PNAS USA*, 98 (15) pp. 8850-8855, 2001.

De Maattos et al., "Brain to Plasma Amyloid-ß Efflux: a Measure of Brain Amyloid Burden in a Mouse Model of Alzheimer's Disease", *Science*, 295(5563): pp. 2264-2267, 2002.

Shealy, D. et al., "Characterization of golimumab, a human monoclonal antibody specific for human tumor necrosis factor alpha", *MABS*, vol. 2, No. 4, pp. 428-439 (Jul. 2010).

Foote et al., "Antibody Framework Residues Affecting the Conformation of the Hypervariable Loops", *Journal of Molecular Biology*, 224(2), pp. 487-499 (1992).

Winter et al., "Antibody-based Therapy", *Immunology Today*, 14(6), pp. 243-246 1993.

Ngo et al., "Computational Complexity, Protein Structure Prediction, and the Levinthal Paradox", *The Protein Folding Problem and Tertiary Structure Prediction*, p. 492-495, 1994.

Wells, Additivity of Mutational Effects in Proteins, *Biochemistry*, vol. 26, No. 37 p. 8509-8517, 1990.

Socher, S., et al. "Antibodies against amino acids 1-15 of tumor necrosis factor block its binding to cell-surface receptor", *Proc. Natl. Acad. Sci.*, USA 84:8829-8833, 1987.

Borrebaeck, C.A.K. (Ed.), Antibody Engineering, 2nd Edition, *Pub Oxford University Press*, p. 267-293, 1995.

Goh, C., "Tumor Necrosis Factors in Clincal Practice", *Annals of the Academy of Medicine*, 19(2):235-239, 1990.

Yan, L. et al., "A Preparation and Characterization of Monoclonal Antibodies Against Recombinant Human Tumor Necrosis Factor Alpha", *Chinese J. Biotechnology*, 7(2):121-126, 1991.

Elliott, M.J. et al., "A Repeated Therapy with Monoclonal Antibody to Tumour Necrosis Factor α (cA2) in Patients with Rheumatoid Arthritis", *The Lancet*, 344:1125-1127, 1994.

Knight, D. M. et al., "A Construction and Initial Characterization of a Mouse-Human Chimeric Anti-TNF Antibody", *Mol. Immunol.* 30 (16): 1443-1453, 1993.

Davenport, C. et al., "A Stimulation of Human B Cells Specific for Candida Albicans for Monoclonal Antibody Production", FEMS *Microbiol. Immunol.* 4(6):335-343 Abstract, 1992.

Pennica, D., et al., "A Human Tumour Necrosis Factor: Precursor Structure, Expression and Homology to Lymphotoxin", *Nature*, 312 (20/27): 724-729, 1984.

Gray, P. W., et al., "A Cloning and Expression of cDNA for Human Lumphotoxin, a Lympholine with Tumour Necrosis Activity", *Nature*, 312 (20/27):721-724, 1984.

Peterson, C.M., et al., "A bioactive human recombinant tumor necrosis factor-α: an unstable dimer", *Eur. J. Immunol.*, 19:1887-1894, 1989.

Smith, C.A. et al., "A Receptor for Tumor Necrosis Factor Defines an Unusual Family of Cellular and Viral Proteins", *Science*, 248-1019-1023, 1990.

Brennan, F.M. et al., "A Inhibitory Effect of TNF α Antibodies on Synovial Cell Interleukin-1 Production in Rheumatoid Arthritis", *The Lancet*, 244-247, 1989.

Hahn, T., et al., "A use of monoclonal antibodies to a human cytotoxin for its isolation and for examining the self-induction of resistance to this protein", *Proc. Natl. Acad, Sci. USA* 82:3814-3818, 1985.

Grau, G.E. et al, "A tumor necrosis factor (cachectin) as an essential mediator in murine cerebral malaria", *Science*, 237:1210-1212, 1987.

Jones, E.Y., et al., "A structure of tumour necrosis factor", *Nature*, 338:225-228, 1989.

Clark, W.R., "A Types of Antibody Reactions", *The Experimental Foundations of Modern Immunology*, (NY: John Wiley & Sons, Inc.), 4th Ed, p. 143-155, 1991.

Beutler, B. et al., "A cachectin and tumour necrosis factor as two sides of the same biological coin", *Nature*, 320-584-588, 1986.

Folks, T.M. et al., "A tumor necrosis factor α induces expression of human immunodeficiency virus in a chronically infected T-cell clone", *Proc. Natl, Acad, Sci, USA* 86:2365-2368, 1989.

Hird, V. et al., "Immunotherapy with Monoclonal Antibodies", *Genes and Cancer* (John Wiley and Sons, Ltd), pp. 183-189, 1990.

Rhein, R. "Another sepsis drug down-Immunex-TNF receptor", *Biotechnology Newswatch*, Monday, Oct. 4, 1993, p. 1, 3.

Boyle, P., et al., "A Novel Monoclonal Human IgM Autoantibody which Binds Recombinant Human and Mouse Tumor Necrosis Factor-α" *Cellular Immunology*, 152:556-568, 1993.

Boyle, P. et al., "The B5 Monoclonal Human Autoantibody Binds to Cell Surface TNF α on Human Lumphoid Cells and Cell Lines and Appears to Recognize a Novel Epitope", *Cellular Immunology*, 152:569-581, 1993.

Sheehan, K.C.F. et al., "A Generation and Characterization of Hamster Monoclonal Antibodies That Neutralize Murine Tumor Necrosis Factors", *The Journal of Immunology*, 142(11): 3884-3893, 1989.

Jacob, C.O. et al., "A tumor necrosis factor-α in murineautoimmune-lupus-nephritis", *Nature*, 331:356-358, 1988.

Mateo C., et al., "A Removal of Amphipathic Epitopes from Genetically Engineered Antibodies: Production of Modified Immunoglobulins with Reduced Immunogenicity", *Hybridoma*, 19(6): 463-471, 2000.

Paul, W.E. (Ed)., "Structure and Function of Immunoglobulins", *Fundamental Immunology*, 3rd Edition, Pub Raven Press Ltd., pp. 292-293, 1993.

Kawaski, H. et al., "Analysis of Endotoxin Fever in Rabbits by Using a Monoclonal Antibody to Tumor Necrosis Factor (Cachectin)", *Infection and Immunity*, 57 (10):3131-3135, 1989.

Oliff, A., et al., "Tumors Secreting Human TNF/Cachectin Induce Cachexia in Mice", *Cell*, 50:555-563, 1987.

Mule, J.J. et al., "A antitumor activity of recombinant interleukin 6 in mice", *The Journal of Experimental Medicine*, 171:629-636, 1990.

Leuttig, B., et al., "Evidence for the existence of two forms of membrane tumor necrosis factor: an integral protein and a molecule attached to its receptor", *The Journal of Immunology*, 143:4034-4038, 1989.

Barbuto, J.A.M. et al., "A production of neutralizing antibodies to tumor necrosis factor y human tumor-infiltrating B lymphocytes", *Proceedings of the American Association for Cancer Research*, 34:387, Abstract 2904, 1993.

Bendtzen, K. et al., "Auto-antibodies to IL-1 α and TNF α in normal individuals and in infectious and immunoinflammatory disorders", *The Physiological and Pathological Effects of Cytokines*, 10B:447-452, 1990.

(56) References Cited

OTHER PUBLICATIONS

Fomsgaard, A. et al., "Auto-antibodies to tumour necrosis factor α in healthy humans and patients with inflammatory disease and gram-negative bacterial infections", *Scan J. Immunol.*, 30: 219-223, 1989.

James, K. et al., "A Human Monoclonal Antibody Production Current Status and Future Prospects", *Journal of Immunological Methods*, 100:5-40, 1987.

Alberts, B. et al., "Molecular Biology of the Cell", *Garland Publishing Inc.* pp. 182-183, 1983.

Simpson, S.Q. et al., "A Role of Tumor Necrosis Factor in Sepsis and Acute Lung Injury", *Critical Care Clinics*, 5:27-47, 1989.

Bendtzen, K. et al., "Native inhibitors (autoantibodies) of IL-1 α and TNF", *Immunology Today*, 10(7):222, 1989.

Agarwal et al.(2012) "Update on islet cell transplantation for type 1 diabetes." *Semin Intervent Radiol* 29(2): 90-98.

Argiles et al.,(1994). "Cytokines and diabetes: the final step? Involvement of TNF-alpha in both type I and II diabetes mellitus." *Horm Metab Res* 26(10): 447-449.

Arif et al., (2010). "Anti-TNFalpha therapy—killing two birds with one stone?" *Lancet* 375(9733): 2278.

Atkinson et al.,(2011). "How does type 1 diabetes develop?: the notion of homicide or beta-cell suicide revisited." *Diabetes* 60(5): 1370-1379.

Blau et al.,(2015). "Long-term immunosuppression after solitary islet transplantation is associated with preserved C-peptide secretion for more than a decade." *Am J Transplant* 15(11): 2995-3001.

Bluestone et al.,(2010). "Genetics, pathogenesis and clinical interventions in type 1 diabetes." *Nature* 464(7293): 1293-1300.

Bougneres et al.,(1988). "Factors associated with early remission of type I diabetes in children treated with cyclosporine." *N Engl J Med* 318(11): 663-670.

Bougneres, et al.,(1990). "Limited duration of remission of insulin dependency in children with recent overt type I diabetes treated with low-dose cyclosporin." *Diabetes* 39(10): 1264-1272.

Boulton et al., (2007). "Unstable diabetes in a patient receiving anti-TNF-alpha for rheumatoid arthritis." *Rheumatology* (Oxford) 46(1): 178-179.

Cavallo et al., (1991). "Cytokines in sera from insulin-dependent diabetic patients at diagnosis." *Clin Exp Immunol* 86(2): 256-259.

Chase, et al.,(1990). "A trial of nicotinamide in newly diagnosed patients with type 1 (insulin-dependent) diabetes mellitus." *Diabetologia* 33(7): 444-446.

Cook, et al.,(1989). "Double-blind controlled trial of azathioprine in children with newly diagnosed type I diabetes." *Diabetes* 38(6): 779-783.

Daneman, D. (2006). "Type 1 diabetes." *Lancet* 367(9513): 847-858.

Dunger, et al. (1995). "Impact of metabolic activity of beta cells on cytokine-induced damage and recovery of rat pancreatic islets." *Acta Diabetol* 32(4): 217-224.

Eisenbarth,G. S. (2004). "Type 1 diabetes: molecular, cellular and clinical immunology." *Adv Exp Med Biol* 552: 306-310.

Gitelman, et al., (2013). "Antithymocyte globulin treatment for patients with recent-onset type 1 diabetes: 12-month results of a randomised, placebo-controlled, phase 2 trial." *Lancet Diabetes Endocrinol* 1(4): 306-316.

Gitelman, et al.,(2013). "Antithymocyte globulin therapy for patients with recent-onset type 1 diabetes: a randomized double-blind phase 2 trial." *The Lancet Diabetes and Endocrinology in Press*.

Glandt et al.,(2004). "Treatment of type 1 diabetes with anti-T-cell agents: from T-cell depletion to T-cell regulation." *Curr Diab Rep* 4(4): 291-297.

Gottlieb et al.,(2010). "Failure to preserve beta-cell function with mycophenolate mofetil and daclizumab combined therapy in patients with new-onset type 1 diabetes." *Diabetes Care* 33(4): 826-832.

Han, S. et al.,(2013). "Novel autoantigens in type 1 diabetes." *Am J Transl Res* 5(4): 379-392.

Harrison et al.,(1985). "Increase in remission rate in newly diagnosed type I diabetic subjects treated with azathioprine." *Diabetes* 34(12): 1306-1308.

Herold et al.,(2009). "Treatment of patients with new onset Type 1 diabetes with a single course of anti-CD3 mAb Teplizumab preserves insulin production for up to 5 years." *Clin Immunol* 132(2): 166-173.

JDRF. (2013). "Type 1 diabetes facts; http://jdrf.org/about-jdrf/fact-sheets/type-1-diabetes-facts/." 2013.

Kawahara et al.,(1991). "Species differences in human and rat islet sensitivity to human cytokines. Monoclonal anti-interleukin-1 (IL-1) influences on direct and indirect IL-1-mediated islet effects." *Cytokine* 3(2): 117-124.

Kleijwegt et al.,(2010). "Critical role for TNF in the induction of human antigen-specific regulatory T cells by tolerogenic dendritic cells." *J Immunol* 185(3): 1412-1418.

Kodama, et al.,(2005). "The therapeutic potential of tumor necrosis factor for autoimmune disease: a mechanistically based hypothesis." *Cell Mol Life Sci* 62(16): 1850-1862.

Koulmanda et al.,(2012). "The role of TNF-alpha in mice with type 1- and 2-diabetes." *PLoS One* 7(5): e33254.

Ludvisson et al.,(2001). "Treatment with antioxidants at onset of type 1 diabetes in children: a randomized, double-blind placebo-controlled study." *Diabetes Metab Res Rev* 17(2): 131-136.

Maahs et al., (2010). "Epidemiology of type 1 diabetes." *Endocrinol Metab Clin North Am* 39(3): 481-497.

Mandrup-Poulsen et al.,(1987). "Human tumor necrosis factor potentiates human interleukin 1-mediated rat pancreatic beta-cell cytotoxicity." *J Immunol* 139(12): 4077-4082.

Mastrandrea et al.,(2009). "Etanercept treatment in children with new-onset type 1 diabetes: pilot randomized, placebo-controlled, double-blind study." *Diabetes Care* 32(7): 1244-1249.

Molbak et al.,(1994). "Incidence of insulin-dependent diabetes mellitus in age groups over 30 years in Denmark." *Diabet Med* 11(7): 650-655.

Moran et al. (2013 "Interleukin-1 antagonism in type 1 diabetes of recent onset: two multicentre, randomised, double-blind, placebo-controlled trials." *Lancet* 381(9881): 1905-1915.

Mordes et al.,(1996). "The BB/Wor rat and the balance hypothesis of autoimmunity." *Diabetes Metab Rev* 12(2): 103-109.

Orban et al.,(2011). "Co-stimulation modulation with abatacept in patients with recent-onset type 1 diabetes: a randomised, double-blind, placebo-controlled trial." *Lancet* 378(9789): 412-419.

Pescovitz et al.,(2009). "Rituximab, B-lymphocyte depletion, and preservation of beta-cell function." *N Engl J Med* 361(22): 2143-2152.

Rabinovitch, A. (1998). "An update on cytokines in the pathogenesis of insulin-dependent diabetes mellitus." *Diabetes Metab Rev* 14(2): 129-151.

Ribgy et al.,(2015). "Alefacept provides sustained clinical and immunological effects in new-onset type 1 diabetes patients." *J Clin Invest* 125(8): 3285-3296.

Sherry et al (2011). "Teplizumab for treatment of type 1 diabetes (Protege study): 1-year results from a randomised, placebo-controlled trial." *Lancet* 378(9790): 487-497.

Stanescu et al., (2012). "The epidemiology of type 1 diabetes in children." *Endocrinol Metab Clin North Am* 41(4): 679-694.

Tolerx, G. A. (2011). "GlaxoSmithKline and Tolerx announce phase III DEFEND-1 study of otelixizumab in type 1 diabetes did not meet its primary endpoint." Retrieved Mar. 11, 2011.

Van Belle, T. L. et al. (2011). "Type 1 diabetes: etiology, immunology, and therapeutic strategies." *Physiol Rev* 91(1): 79-118.

Van Eijk, I.C., et al., (2007). "Decrease of fructosamine levels during treatment with adalimumab in patients with both diabetes and rheumatoid arthritis." *Eur J Endocrinol* 156(3): 291-293.

Yazdani-Biuki, B., H. et al., (2004). "Improvement of insulin sensitivity in insulin resistant subjects during prolonged treatment with the anti-TNF-alpha antibody infliximab." *Eur J Clin Invest* 34(9): 641-642.

Centocor, Inc., Trial Record for C0524T02 NCT00207714, "A Randomized, Double-blind, Dose-ranging Trial of CNTO148 Sub-

(56) References Cited

OTHER PUBLICATIONS cutaneous Injection Compared With Placebo in Subjects With Active Rheumatoid Arthritis Despite Treatment With Metrotrexate", pp. 1-3, Oct. 2012.

Centocor, Inc., Trial Record for C0524T03 NCT00207740, "A Phase 2, Multicenter, Randomized, Double-blind, Placebo-controlled, Parllel-group, Dose-ranging Study Evaluating the Efficacy and Safety of CNTO148 Administered Subcutaneously in Symptomatic Subjects With Severe Presistent Asthma", pp. 1-4 Aug. 2012.

Centocor, Inc., Trial Record for C0524T05 NCT00264537, "A Multicenter, Randomized, Double-blind, Placebo-controlled Trial of Golumumab, a Fully Human Anti-TNFa Monoclonal Antibody, Administered Subcutaneously, in Methotrexate-naive Subjects with Active Rheumatoid Arthrisis", pp. 1-5 Aug. 2014.

Centocor, Inc., Trial Record for C0524T06 NCT00264550, "A Multicenter, Randomized, Double-blind, Placebo-controlled Trial of Golimumab, a Fully Human Anti-TNFa Monoclonal Antibody, Administered Subcutaneously, in Subjects with Active Rheumatoid Arhtritis Despite Methrotrexate Therapy", pp. 1-5 Apr. 2014.

Centocor, Inc., Trial Record for C0524T08 NCT00265096, "A Multicenter, Randomized, Double-blind, Placebo-controlled Trial of Golimumab, a Fully Human Anti-TNFa Monoclonal Antibody, Administered Subcutaneously in Subjects with Active Psoriatic Arthritis", pp. 1-4, Jul. 2013.

Centocor, Inc., Trial Record for C0524T09 NCT00265083, "A Multicenter, Randomized Double-blind, Placebo-controlled Trial of Golimumab, a Fully Human Anti-TNF alpha Monoclonal Antibody, Administered Subcutaneously, in Subject with Active Ankylosing Spondylitis", pp. 1-4 Jul. 2013.

Centocor, Inc., Trial Record for C0524T11 NCT00299546, "A Multicenter, Randomized Double-blind, Placebo-controlled Trial of Golimumab, a Fully Human Anti-TNF alpha Monoclonal Antibody, Administered Subcutaneously, in Subject with Active Rheumatoid Arthritis and Previously Treated with Biological AntiTNFa Agent(s)", p. 1-4 Jan. 2014.

Centocor, Inc., Trial Record for C0524T12 NCT00361335, "A Multicenter, Randomized Double-blind, Placebo-controlled Trial of Golimumab, a Fully Human Anti-TNF alpha Monoclonal Antibody, Administered Intravenously, in Subjects with Active Rheumatoid Arthritis Despite Methotrexate Therapy", p. 1-5 Jul. 2014

Janssen Research & Development, LLC., Trial Record for C0524T16 NCT0048774, "A Phase 2/3 Multicenter, Randomized, Placebo-controlled, Double-blind Study to evaluate the Safety and Efficacy of Golimumab Induction Therapy, Administered Intravenously, in Subjects with Moderately to Severely Active Ulcerative Colitis", pp. 1-4 Apr. 2013.

Janssen Research & Development, LLC, Trial Record for C0524T16 NCT00488631, "A Phase 3 Multicenter, Randomized, Placebo-controlled, Double-blind Study to Evaluate the Safety and Efficacy of Golimumab Maintenance Therapy, Administered Subcutaneously, in Subjects with Moderately to Severely Active Ulcerative Colitis", pp. 1-5. Mar. 2016.

Janssen Research & Development, LLC, Trial Record for C0524T17 NCT00487539, "A Phase 2/3 Multicenter, Randomized, Placebo-controlled, Double-blind Study to Evaluate the Safety and Efficacy of Golimumab Induction Therapy, Administered Subcutaneously, in Subjects with Moderately to Severely Active Ulcerative Colitis", pp. 1-4 Jan. 2014.

Janssen Research & Development, LLC, Trial Record for C0524T17 NCT00488631, "A Phase 3 Multicenter, Randomized, Placebo-controlled, Double-blind Study to Evaluate the Safety and Efficacy of Golimumab Maintenance Therapy, Administered Subcutaneously, in Subjects with Moderately to Severely Active Ulcerative Colitis", pp. 1-5 Mar. 2016.

Janssen Research & Development, LLC, Trial Record for C0524T18 NCT00488631, "A Phase 3 Multicenter, Randomized, Placebo-controlled, Double-blind Study to Evaluate the Safety and Efficacy of Golimumab Maintenance Therapy, Administered Subcutaneously, in Subjects with Moderately to Severely Active Ulcerative Colitis", pp. 1-5 Mar. 2016.

Janssen Research & Development, LLC, Trial Record for C0524T28 NCT01248780, "A Phase 2/3 Multicenter, Randomized, Double-blind, Placebo-controlled Study to Evaluate the Safety and Efficacy of Golimumab the Treatment of Chinese Subjects with Active Rheumatoid Arthritis Despite Methotrexate Therapy", pp. 1-4 Aug. 2013.

Centocor, Inc., Trial Record for C0524T29 NCT01248793, "A Phase 3 Multicenter, Randomized, Double-blind, Placebo-controlled, Study to Evaluating the Efficacy and Safety of Golimumab in the Treatment of Chinese Subjects with Ankylosing Spondylitis", pp. 1-3 Mar. 2013.

Centocor, Inc., Trial Record for CNTO148ART3001 NCT00973479, "A Multicenter, Randomized, Double-blind, Placebo-controlled Trial of Golimumab, an Anti-TNF alpha Monoclonal Antibody, Administered Intravenously, in Patients with Active Rheumatoid Arthritis Despite Methotrexate Therapy", p. 1-4 Nov. 2013.

Janssen Research and Development, LLC, Trial Record for CNTO148JIA3001 NCT0123087, "A Multicenter, Randomized, Double-blind, Randomized-Withdrawal Trial of Subcutaneous Golimumab, a Humanized Anti-TNa Antibody, in Subjects with Active Polyarticular Juvenile Idiopathic Arthritis (JAI) Despite Standard Therapy", p. 1-4 Mar. 2016.

Janssen Research & Development, LLC, Trial Record forCNTO148UCO1001 NCT01900574, "A Phase 1b Open-Label Study to Assess the Safety and Pharmacokinetics of Subcutaneously Administered Golimumab, a Human Anti-TNFa Antibody, Pediatric Subjects with Moderately to Severely Active Ulcerative Colotis", p. 1-4 Mar. 2017.

Merck Sharp & Dohme Corp., Trial Record for P07642 NCT01453725, "A Multicenter, Randomized, Double-blind, Placebo-controlled Study of the Effect of Golimumab Administered Subcutaneously in Subjects with Active Axial Spondyloarthritis", p. 1-4 Mar. 2017.

Insel et al., "Staging Presymptomatic Type 1 Diabetes: A Scientific Statement of JDRF, the Endocrine Society, and the American Diabetes Association", *Diabetes Care*, vol. 38, pp. 196401974, 2015.

Weigmann et al., "Immunotherapy in Autoimmune Type 1 Diabetes", *The Review of Diabetic Research*, vol. 9, pp. 68-81, 2012.

Barbanti et al., "Mode of interaction between tumor necrosis factor alpha and a monoclonal antibody expressing a recurrent idiotype", *Hybridoma* 12(1); pp. 1-13 1993.

Lee et al., "The role of TNF-a in the pathogenesis of type 1 diabetes in the nonobese diabetic mouse: Analysis of Dendritic cell maturation", vol. 102, No. 44, pgd. 15995016000, Nov. 2005.

Timper, Katharina et al., "Infliximab in the treatment of Crohn disease and type 1 diabetes", *Diabetes Care*, vol. 36, No. 7, pp. E90-e91 XP002793259, Jul. 2013.

Joerns, Anne et al., "TNF-aplha Antibody Therapy in Combination With the T-Cell-Specific Antibody Anti-TCE Reverses the Diabetic Metabolic State in the Lew.1AR1-iddm Rat", *Diabetes*, vol. 64, No. 8., pp. 2880-2891, XP002793260, Aug. 2015.

Dutta and Sengupta, "Men and Mice: Relating their Ages." Life Sci, May 1, 2016;152:244-8. (epub Oct. 24, 2015).

```
TNVs        ATGGGGTTTGGGCTGAGCTGGGTTTTCCTCGTTGCTCTTTTAAGA

Q  V  Q  L  V  E  S  G  G  V
germline                 CAGGTGCAGCTGGTGGAGTCTGGGGGAGGCGTG
TNVs        GGTGTCCAGTGT............................
TNV148(B)   GGTGTCCAGTGT.....A......................

V  Q  P  G  R  S  L  R  L  S  C  A  A  S  G
germline    GTCCAGCCTGGGAGGTCCCTGAGACTCTCCTGTGCAGCCTCTGGA
TNVs        .............................................

F  T  F  S  S  Y  A  M  H  W  V  R  Q  A  P
germline    TTCACCTTCAGTAGCTATGCTATGCACTGGGTCCGCCAGGCTCCA
TNV14,15    .............................................
TNV148(B)   ....T........................................
TNV196      ...................C.........................

G  K  G  L  E  W  V  A  V  I  S  Y  D  G  S
germline    GGCAAGGGGCTGGAGTGGGTGGCAGTTATATCATATGATGGAAGC
TNV14       ........................A....C.T............T
TNV15       ........................T......T............T
TNV148(B)   .....C..................T....G..............
TNV196      ................................T...........

N  K  Y  Y  A  D  S  V  K  G  R  F  T  I  S
germline    AATAAATACTACGCAGACTCCGTGAAGGGCCGATTCACCATCTCC     SEQ ID NO: 7 cont'd.->
TNV14       .GC...A.G.....G..............A...............     SEQ ID NO: 34 cont'd.->
TNV15       ..C...A.G............................C......
TNV148(B)   ......A.G....................................
TNV196      ......A.G.C................................G....
```

FIGURE 2A

```
                    R   D   N   S   K   N   T   L   Y   L   Q   M   N   S   L
germline     AGAGACAATTCCAAGAACACGCTGTATCTGCAAATGAACAGCCTG
TNV14        ............................................
TNV15        ..................G.........................
TNV148       .........C..................................
TNV148B      ............................................
TNV196       ...............................T............

R   A   E   D   T   A   V   Y   Y   C   A   R
germline     AGAGCTGAGGACACGGCTGTGTATTACTGTGCGAGA
TNV14,15     ....................................GATCGAGGT
TNV148(B)    ............................................A
TNV196       ....................T...............

Y   Y   Y   Y   Y   G   M   D   V   W
germline                          TACTACTACTACTACGGTATGGACGTCTGG
TNV14        ATATCAGCAGGTGGAA..............................
TNV15        G.C...........A.T..T..........................
TNV148(B)    ...G..........A...............................
TNV196       ..TGG.........A...............................

G   Q   G   T   T   V   T   V   S   S       SEQ ID NO: 7
germline     GGGCAAGGGACCACGGTCACCGTCTCCTCAG                    SEQ ID NO: 34
TNV14        ..C............................
TNV15        ..C............................
TNV148(B)    ..C............................
TNV196       ..C..G.........................
```

FIGURE 2B

```
TNVs         ATGGAAGCCCCAGCTCAGCTTCTCTTCCTCCTGCTACTCTGGCTC

E  I  V  L  T  Q  S  P  A  T
germline     GAAATTGTGTTGACACAGTCTCCAGCCACC
TNVs         CCAGATACCACCGGA................................

L  S  L  S  P  G  E  R  A  T  L  S  C  R  A
germline     CTGTCTTTGTCTCCAGGGGAAAGAGCCACCCTCTCCTGCAGGGCC
TNVs         .............................................

S  Q  S  V  S  S  Y  L  A  W  Y  Q  Q  K  P
germline     AGTCAGAGTGTTAGCAGCTACTTAGCCTGGTACCAACAGAAACCT
TNV14,15     .............................................
TNV148,196   ..........TA.................................

G  Q  A  P  R  L  L  I  Y  D  A  S  N  R  A
germline     GGCCAGGCTCCCAGGCTCCTCATCTATGATGCATCCAACAGGGCC
TNVs         .............................................

T  G  I  P  A  R  F  S  G  S  G  S  G  T  D
germline     ACTGGCATCCCAGCCAGGTTCAGTGGCAGTGGGTCTGGGACAGAC
TNVs         .............................................

F  T  L  T  I  S  S  L  E  P  E  D  F  A  V
germline     TTCACTCTCACCATCAGCAGCCTAGAGCCTGAAGATTTTGCAGTT
TNVs         .............................................

Y  Y  C  Q  Q  R  S  N  W  P  P  F  T  F  G
Germline     TATTACTGTCAGCAGCGTAGCAACTGGCCTCCATTCACTTTCGGC
TNVs         ............................A................

P  G  T  K  V  D  I  K  R
germline     CCTGGGACCAAAGTGGATATCAAACGT
TNVs         ...........................
```

FIGURE 3

```
germline    MGFGLSWVFLVALLRGVQC                         signal
TNVs        ...................

germline    QVQLVESGGGVVQPGRSLRLSCAASGFTFS              FR1
TNVs        ..............................
TNV148(B)   ............................I..

germline    SYAMH                                       CDR1
TNVs        .....

germline    WVRQAPGKGLEWVA                              FR2
TNVs        .............
TNV148(B)   .......N.....

germline    VISYDGSNKYYADSVKG                           CDR2
TNV14       I.L....S.K......D
TNV15       F.L.......K......
TNV148(B)   FM........K......
TNV196      F.........KS.....

germline    RFTISRDNSKNTLYLQMNSLRAEDTAVYYCAR            FR3
TNV14       ................................
TNV15       ..........A.....................
TNV148      .......P........................
TNV148B     ................................
TNV196      ...V........F...............F....

germline    ---------YYYYYGMDV
TNV14       DRGISAGGN.........                          CDR3
TNV15       ...V....N.........
TNV148(B)   ....A...N.........
TNV196      ....G...N.........

germline    WGQGTTVTVSS                                 J6
TNVs        ...........
```

FIGURE 4

```
TNVs         MEAPAQLLFLLLLWLPDTTG                        signal germline     EIVLTQSPATLSLSPGERATLSC                     FR1
TNVs         .......................

germline     RASQSVSSYLA                                 CDR1
TNV14        ..........
TNV15        ..........
TNV148(B)    ......Y...
TNV196       ......Y...

germline     WYQQKPGQAPRLLIY                             FR2
TNVs         ...............

germline     DASNRAT                         CDR2
TNVs         .......

germline     GIPARFSGSGSGTDFTLTISSLEPEDFAVYYC            FR3
TNVs         ................................

germline     QQRSNWPPFT                                  CDR3
TNVs         ..........

germline     FGPGTKVDIK                                  J3
TNVs         ..........
```

FIGURE 5

Figure 18: Study schema for study CNTO148DML2001
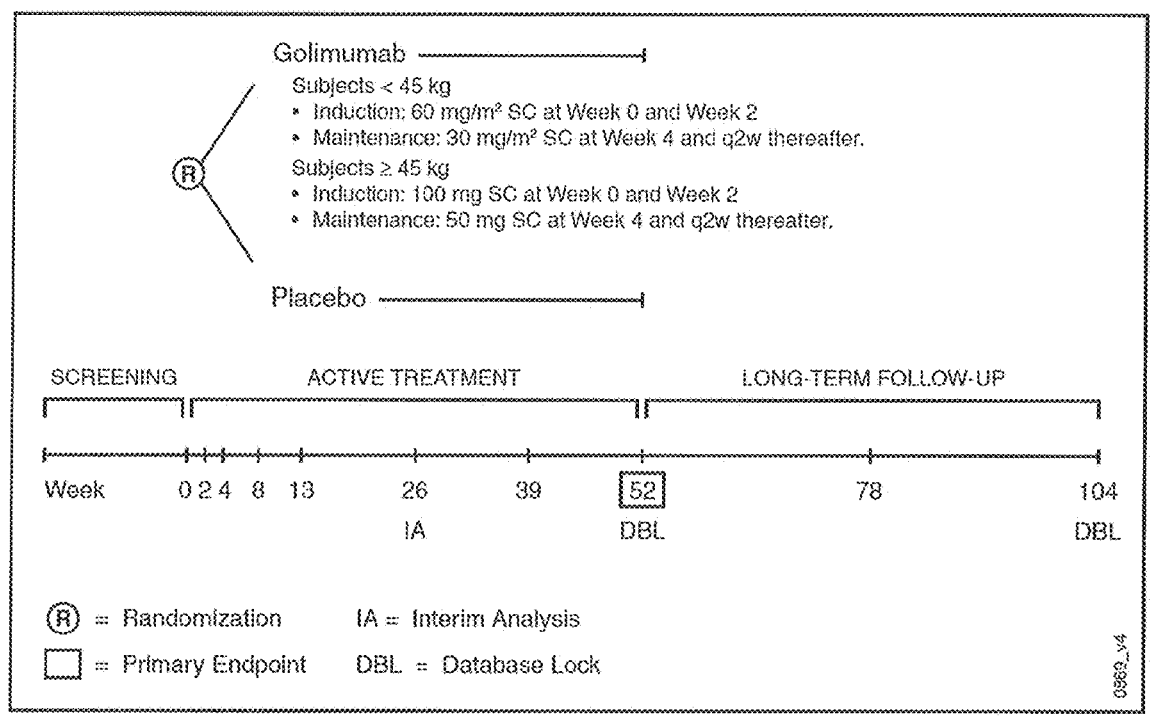

Figure 19: Simulated golimumab concentrations (median and 95% Prediction Interval) through Week 24 for various dosing regimens (without MTX) in virtual patients ages 6 - 21

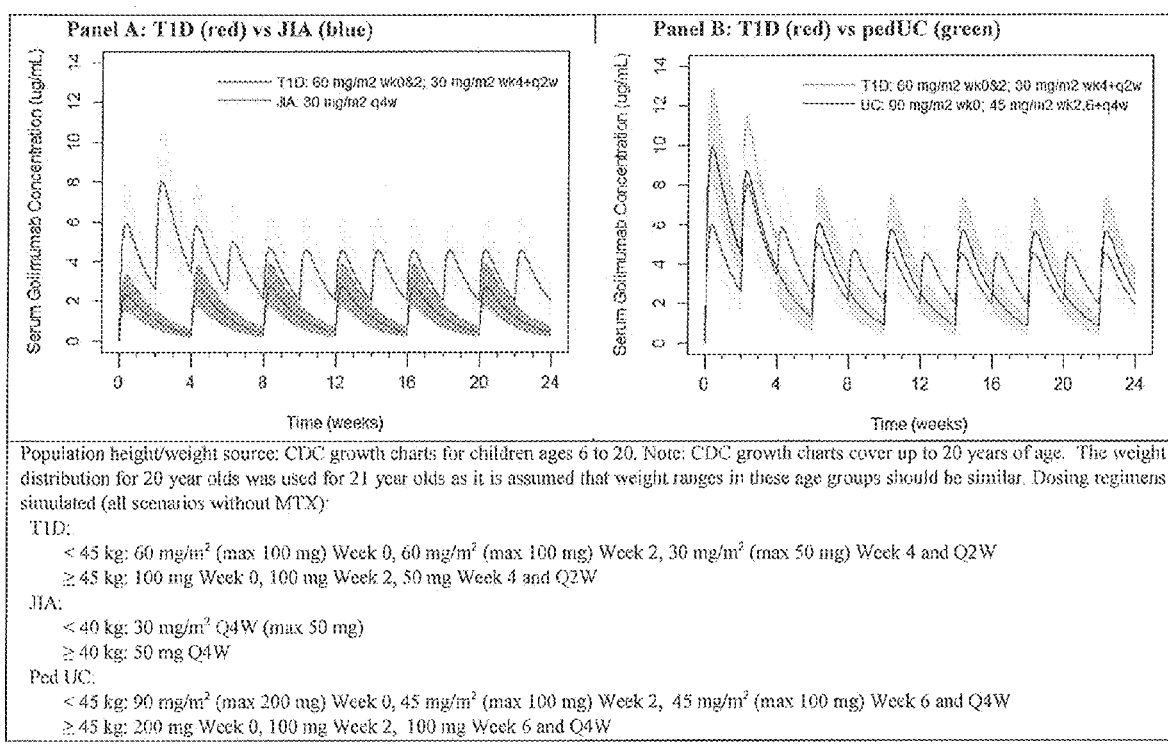

Population height/weight source: CDC growth charts for children ages 6 to 20. Note: CDC growth charts cover up to 20 years of age. The weight distribution for 20 year olds was used for 21 year olds as it is assumed that weight ranges in these age groups should be similar. Dosing regimens simulated (all scenarios without MTX):

T1D:
  < 45 kg: 60 mg/m² (max 100 mg) Week 0, 60 mg/m² (max 100 mg) Week 2, 30 mg/m² (max 50 mg) Week 4 and Q2W
  ≥ 45 kg: 100 mg Week 0, 100 mg Week 2, 50 mg Week 4 and Q2W
JIA:
  < 40 kg: 30 mg/m² Q4W (max 50 mg)
  ≥ 40 kg: 50 mg Q4W
Ped UC:
  < 45 kg: 90 mg/m² (max 200 mg) Week 0, 45 mg/m² (max 100 mg) Week 2, 45 mg/m² (max 100 mg) Week 6 and Q4W
  ≥ 45 kg: 200 mg Week 0, 100 mg Week 2, 100 mg Week 6 and Q4W

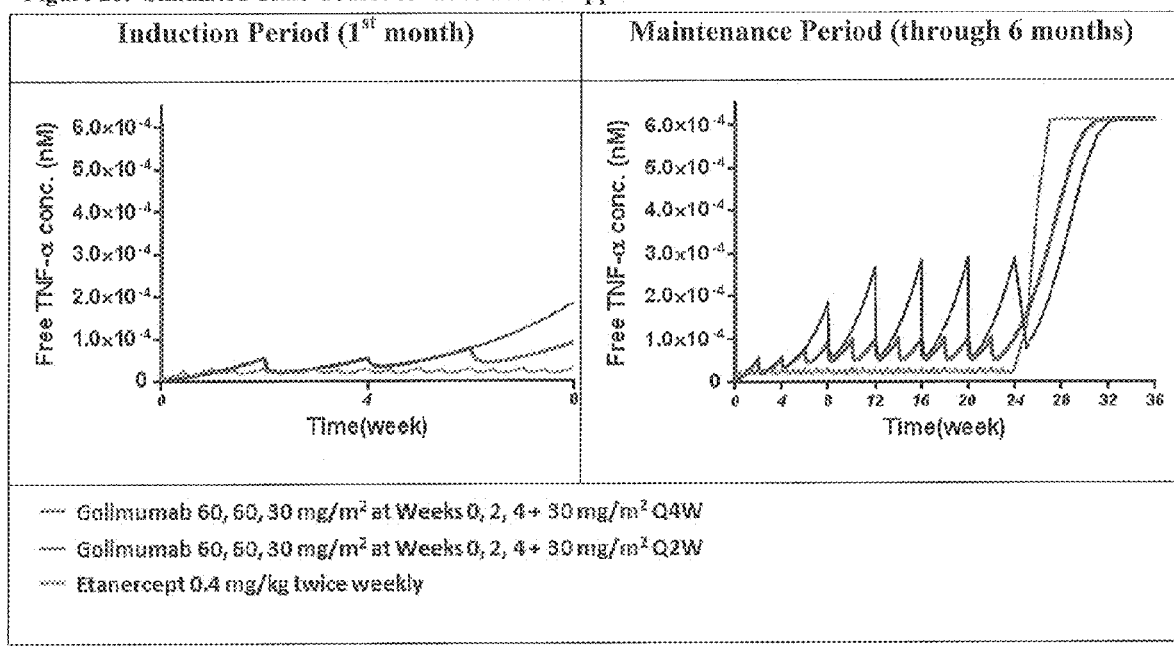
Figure 20: Simulated Time Course for Free TNFα Suppression

Figure 21: Features of the UltraSafe
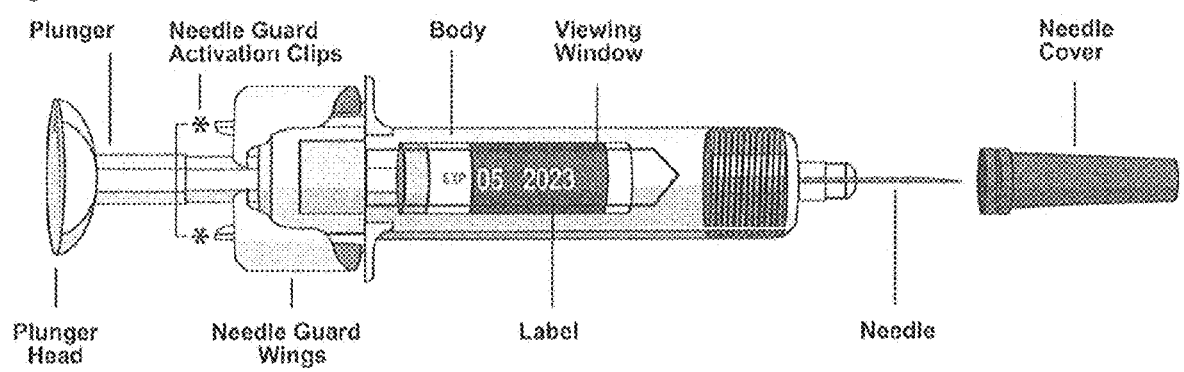

Figure 22: Illustration of the SIMPONI® VarioJect and features
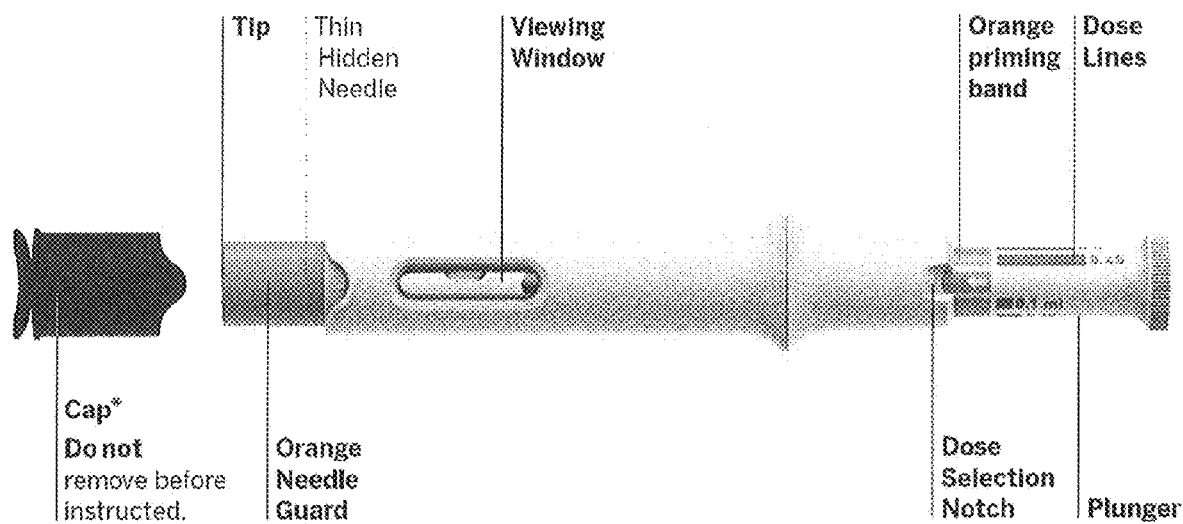

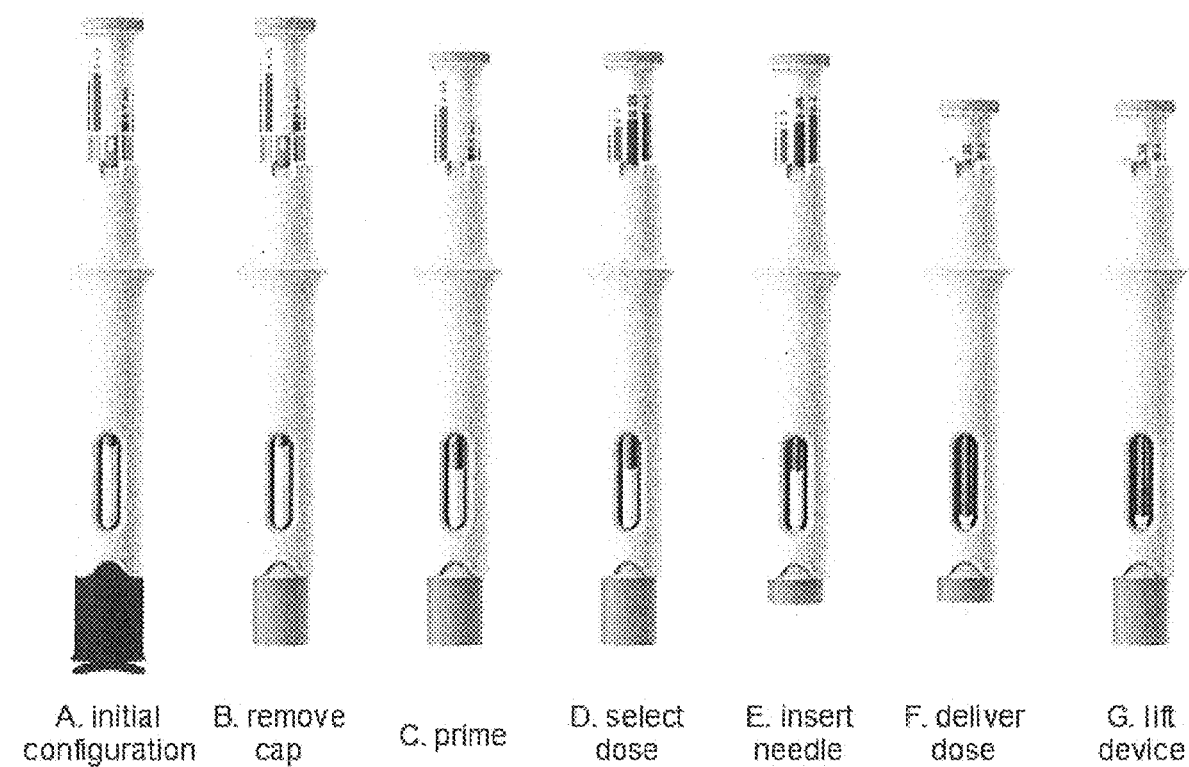
Figure 23: Steps in the administration of SIMPONI® using the VarioJect™

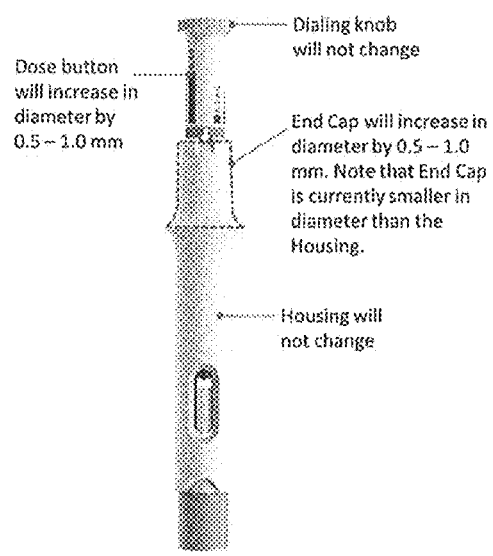
Figure 24: Proposed Design Modifications to VarioJect Device

SEQUENCE LISTING

```
<160> NUMBER OF SEQ ID NOS: 37

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Heavy Chain complementarity determining region
      1 (CDR1).

<400> SEQUENCE: 1

Ser Tyr Ala Met His
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      2 (CDR2).
<220> FEATURE:
<221> NAME/KEY: MISC_FEATURE
```

```
<222> LOCATION: (1)..(1)
<223> OTHER INFORMATION: Xaa at position 1 is selected from Ile, Phe or
      Val.
<220> FEATURE:
<221> NAME/KEY: MISC_FEATURE
<222> LOCATION: (2)..(2)
<223> OTHER INFORMATION: Xaa at position 2 is selected from Ile or Met.
<220> FEATURE:
<221> NAME/KEY: MISC_FEATURE
<222> LOCATION: (3)..(3)
<223> OTHER INFORMATION: Xaa at position 3 is selected from Ser or Leu.
<220> FEATURE:
<221> NAME/KEY: MISC_FEATURE
<222> LOCATION: (4)..(4)
<223> OTHER INFORMATION: Xaa at position 4 is selected from Tyr or Phe.
<220> FEATURE:
<221> NAME/KEY: MISC_FEATURE
<222> LOCATION: (10)..(10)
<223> OTHER INFORMATION: Xaa at position 10 is selected from Lys or Tyr.
<220> FEATURE:
<221> NAME/KEY: MISC_FEATURE
<222> LOCATION: (11)..(11)
<223> OTHER INFORMATION: Xaa at position 11 is selected from Ser or Tyr.
<220> FEATURE:
<221> NAME/KEY: MISC_FEATURE
<222> LOCATION: (17)..(17)
<223> OTHER INFORMATION: Xaa at position 17 is selected from Asp or Gly.

<400> SEQUENCE: 2

Xaa Xaa Xaa Xaa Asp Gly Ser Asn Lys Xaa Xaa Ala Asp Ser Val Lys
1               5                   10                  15

Xaa

<210> SEQ ID NO 3
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      3 (CDR3).
<220> FEATURE:
<221> NAME/KEY: MISC_FEATURE
<222> LOCATION: (4)..(4)
<223> OTHER INFORMATION: Xaa at position 4 is selected from Ile or Val.
<220> FEATURE:
<221> NAME/KEY: MISC_FEATURE
<222> LOCATION: (5)..(5)
<223> OTHER INFORMATION: Xaa at position 5 is selected from Ser, Ala or
      Gly.
<220> FEATURE:
<221> NAME/KEY: MISC_FEATURE
<222> LOCATION: (9)..(9)
<223> OTHER INFORMATION: Xaa at position 9 is selected from Asn or Tyr.

<400> SEQUENCE: 3

Asp Arg Gly Xaa Xaa Ala Gly Gly Xaa Tyr Tyr Tyr Tyr Gly Met Asp
1               5                   10                  15

Val

<210> SEQ ID NO 4
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Light Chain complementarity determining region
      1 (CDR1).
<220> FEATURE:
<221> NAME/KEY: MISC_FEATURE
<222> LOCATION: (7)..(7)
```

```
<223> OTHER INFORMATION: Xaa at position 7 is selected from Ser or Tyr.

<400> SEQUENCE: 4

Arg Ala Ser Gln Ser Val Xaa Ser Tyr Leu Ala
1               5                   10

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Light Chain complementarity determining region
      2 (CDR2).

<400> SEQUENCE: 5

Asp Ala Ser Asn Arg Ala Thr
1               5

<210> SEQ ID NO 6
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Light Chain complementarity determining region
      3 (CDR3).

<400> SEQUENCE: 6

Gln Gln Arg Ser Asn Trp Pro Pro Phe Thr
1               5                   10

<210> SEQ ID NO 7
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: heavy chain variable region sequences as
      presented in original Figure 4
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (28)..(28)
<223> OTHER INFORMATION: Xaa at position 28 is selected from Ile or Thr.
<220> FEATURE:
<221> NAME/KEY: MISC_FEATURE
<222> LOCATION: (31)..(35)
<223> OTHER INFORMATION: complementarity determining region 1 (CDR1).
<220> FEATURE:
<221> NAME/KEY: MISC_FEATURE
<222> LOCATION: (36)..(49)
<223> OTHER INFORMATION: framework 2
<220> FEATURE:
<221> NAME/KEY: MISC_FEATURE
<222> LOCATION: (43)..(43)
<223> OTHER INFORMATION: Xaa at position 43 is selected from Lys or Asn.
<220> FEATURE:
<221> NAME/KEY: MISC_FEATURE
<222> LOCATION: (50)..(66)
<223> OTHER INFORMATION: complementarity determining region 2 (CDR2).
<220> FEATURE:
<221> NAME/KEY: MISC_FEATURE
<222> LOCATION: (50)..(50)
<223> OTHER INFORMATION: Xaa at position 50 is selected from Ile, Phe or
      Val.
<220> FEATURE:
```

```
<221> NAME/KEY: MISC_FEATURE
<222> LOCATION: (51)..(51)
<223> OTHER INFORMATION: Xaa at position 51 is selected from Ile or Met.
<220> FEATURE:
<221> NAME/KEY: MISC_FEATURE
<222> LOCATION: (52)..(52)
<223> OTHER INFORMATION: Xaa at position 52 is selected from Ser or Leu.
<220> FEATURE:
<221> NAME/KEY: MISC_FEATURE
<222> LOCATION: (53)..(53)
<223> OTHER INFORMATION: Xaa at position 53 is selected from Tyr or Phe.
<220> FEATURE:
<221> NAME/KEY: MISC_FEATURE
<222> LOCATION: (59)..(59)
<223> OTHER INFORMATION: Xaa at position 59 is selected from Lys or Tyr.
<220> FEATURE:
<221> NAME/KEY: MISC_FEATURE
<222> LOCATION: (60)..(60)
<223> OTHER INFORMATION: Xaa at position 60 is selected from Ser or Tyr.
<220> FEATURE:
<221> NAME/KEY: MISC_FEATURE
<222> LOCATION: (66)..(66)
<223> OTHER INFORMATION: Xaa at position 66 is selected from Asp or Gly.
<220> FEATURE:
<221> NAME/KEY: MISC_FEATURE
<222> LOCATION: (67)..(98)
<223> OTHER INFORMATION: framework 3
<220> FEATURE:
<221> NAME/KEY: MISC_FEATURE
<222> LOCATION: (70)..(70)
<223> OTHER INFORMATION: Xaa at position 70 is selected from Val or Ile.
<220> FEATURE:
<221> NAME/KEY: MISC_FEATURE
<222> LOCATION: (75)..(75)
<223> OTHER INFORMATION: Xaa at position 75 is selected from Ser or Pro.
<220> FEATURE:
<221> NAME/KEY: MISC_FEATURE
<222> LOCATION: (78)..(78)
<223> OTHER INFORMATION: Xaa at position 78 is selected from Thr or Ala.
<220> FEATURE:
<221> NAME/KEY: MISC_FEATURE
<222> LOCATION: (80)..(80)
<223> OTHER INFORMATION: Xaa at position 80 is selected from Tyr or Phe.
<220> FEATURE:
<221> NAME/KEY: MISC_FEATURE
<222> LOCATION: (94)..(94)
<223> OTHER INFORMATION: Xaa at position 94 is selected from Tyr or Phe.
<220> FEATURE:
<221> NAME/KEY: MISC_FEATURE
<222> LOCATION: (99)..(115)
<223> OTHER INFORMATION: complementarity determining region 3 (CDR3).
<220> FEATURE:
<221> NAME/KEY: MISC_FEATURE
<222> LOCATION: (102)..(102)
<223> OTHER INFORMATION: Xaa at position 102 is selected from Ile or
      Val.
<220> FEATURE:
<221> NAME/KEY: MISC_FEATURE
<222> LOCATION: (116)..(126)
<223> OTHER INFORMATION: J6 region

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Xaa Phe Ser Ser Tyr
            20                  25                  30

Ala Met His Trp Val Arg Gln Ala Pro Gly Xaa Gly Leu Glu Trp Val
        35                  40                  45

Ala Xaa Xaa Xaa Xaa Asp Gly Ser Asn Lys Xaa Xaa Ala Asp Ser Val
    50                  55                  60

Lys Xaa Arg Phe Thr Xaa Ser Arg Asp Asn Xaa Lys Asn Xaa Leu Xaa
65                  70                  75                  80

Leu Gln Met Asn Ser Leu Arg Ala Glu Asp Thr Ala Val Xaa Tyr Cys
```

```
                    85                  90                  95

Ala Arg Asp Arg Gly Xaa Ala Ala Gly Gly Asn Tyr Tyr Tyr Tyr Gly
                100                 105                 110

Met Asp Val Trp Gly Gln Gly Thr Thr Val Thr Val Ser Ser
                115                 120                 125

<210> SEQ ID NO 8
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: light chain variable region sequences as
      presented in original Figure 5
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(34)
<223> OTHER INFORMATION: complementarity determining region 1 (CDR1).
<220> FEATURE:
<221> NAME/KEY: MISC_FEATURE
<222> LOCATION: (35)..(49)
<223> OTHER INFORMATION: framework 2
<220> FEATURE:
<221> NAME/KEY: MISC_FEATURE
<222> LOCATION: (50)..(56)
<223> OTHER INFORMATION: complementarity determining region 2 (CDR2).
<220> FEATURE:
<221> NAME/KEY: MISC_FEATURE
<222> LOCATION: (57)..(88)
<223> OTHER INFORMATION: framework 3
<220> FEATURE:
<221> NAME/KEY: MISC_FEATURE
<222> LOCATION: (89)..(98)
<223> OTHER INFORMATION: complementarity determining region 3 (CDR3).
<220> FEATURE:
<221> NAME/KEY: MISC_FEATURE
<222> LOCATION: (99)..(108)
<223> OTHER INFORMATION: J3 region

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
                100                 105

<210> SEQ ID NO 9
<211> LENGTH: 157
<212> TYPE: PRT
<213> ORGANISM: Homo sapiens
<220> FEATURE:
<221> NAME/KEY: MISC_FEATURE
<222> LOCATION: (1)..(157)
<223> OTHER INFORMATION: human TNF alpha monomer sequence
```

<400> SEQUENCE: 9

| | | | | | | | | | | | | | | |
|---|---|---|---|---|---|---|---|---|---|---|---|---|---|---|
| Val | Arg | Ser | Ser | Ser | Arg | Thr | Pro | Ser | Asp | Lys | Pro | Val | Ala | His | Val |
| 1 | | | | 5 | | | | | 10 | | | | | 15 | |
| Val | Ala | Asn | Pro | Gln | Ala | Glu | Gly | Gln | Leu | Gln | Trp | Leu | Asn | Arg | Arg |
| | | | 20 | | | | | 25 | | | | | 30 | | |
| Ala | Asn | Ala | Leu | Leu | Ala | Asn | Gly | Val | Glu | Leu | Arg | Asp | Asn | Gln | Leu |
| | | 35 | | | | | 40 | | | | | 45 | | | |
| Val | Val | Pro | Ser | Glu | Gly | Leu | Tyr | Leu | Ile | Tyr | Ser | Gln | Val | Leu | Phe |
| | 50 | | | | | 55 | | | | | 60 | | | | |
| Lys | Gly | Gln | Gly | Cys | Pro | Ser | Thr | His | Val | Leu | Leu | Thr | His | Thr | Ile |
| 65 | | | | | 70 | | | | | 75 | | | | | 80 |
| Ser | Arg | Ile | Ala | Val | Ser | Tyr | Gln | Thr | Lys | Val | Asn | Leu | Leu | Ser | Ala |
| | | | | 85 | | | | | 90 | | | | | 95 | |
| Ile | Lys | Ser | Pro | Cys | Gln | Arg | Glu | Thr | Pro | Glu | Gly | Ala | Glu | Ala | Lys |
| | | | 100 | | | | | 105 | | | | | 110 | | |
| Pro | Trp | Tyr | Glu | Pro | Ile | Tyr | Leu | Gly | Gly | Val | Phe | Gln | Leu | Glu | Lys |
| | | | | 115 | | | | | 120 | | | | | 125 | |
| Gly | Asp | Arg | Leu | Ser | Ala | Glu | Ile | Asn | Arg | Pro | Asp | Tyr | Leu | Asp | Phe |
| | 130 | | | | | 135 | | | | | 140 | | | | |
| Ala | Glu | Ser | Gly | Gln | Val | Tyr | Phe | Gly | Ile | Ile | Ala | Leu | | | |
| 145 | | | | | 150 | | | | | 155 | | | | | |

<210> SEQ ID NO 10
<211> LENGTH: 18
<212> TYPE: DNA
<213> ORGANISM: Homo sapiens

<400> SEQUENCE: 10
ttggtccagt cggactgg                                                  18

<210> SEQ ID NO 11
<211> LENGTH: 18
<212> TYPE: DNA
<213> ORGANISM: Homo sapiens

<400> SEQUENCE: 11
cacctgcact cggtgctt                                                  18

<210> SEQ ID NO 12
<211> LENGTH: 30
<212> TYPE: DNA
<213> ORGANISM: Homo sapiens

<400> SEQUENCE: 12
cactgttttg agtgtgtacg ggcttaagtt                                     30

<210> SEQ ID NO 13
<211> LENGTH: 18
<212> TYPE: DNA
<213> ORGANISM: Homo sapiens

<400> SEQUENCE: 13
gccgcacgtg tggaaggg                                                  18

<210> SEQ ID NO 14
<211> LENGTH: 25
<212> TYPE: DNA
<213> ORGANISM: Homo sapiens -continued

<400> SEQUENCE: 14
agtcaaggtc ggactggctt aagtt                                                25

<210> SEQ ID NO 15
<211> LENGTH: 28
<212> TYPE: DNA
<213> ORGANISM: Homo sapiens

<400> SEQUENCE: 15
gttgtcccct ctcacaatct tcgaattt                                             28

<210> SEQ ID NO 16
<211> LENGTH: 18
<212> TYPE: DNA
<213> ORGANISM: Homo sapiens

<400> SEQUENCE: 16
ggcggtagac tactcgtc                                                        18

<210> SEQ ID NO 17
<211> LENGTH: 7
<212> TYPE: PRT
<213> ORGANISM: Homo sapiens

<400> SEQUENCE: 17

Met Asp Trp Thr Trp Ser Ile
1               5

<210> SEQ ID NO 18
<211> LENGTH: 35
<212> TYPE: DNA
<213> ORGANISM: Homo sapiens

<400> SEQUENCE: 18
tttcgtacgc caccatggac tggacctgga gcatc                                     35

<210> SEQ ID NO 19
<211> LENGTH: 34
<212> TYPE: DNA
<213> ORGANISM: Homo sapiens

<400> SEQUENCE: 19
tttcgtacgc caccatgggg tttgggctga gctg                                      34

<210> SEQ ID NO 20
<211> LENGTH: 35
<212> TYPE: DNA
<213> ORGANISM: Homo sapiens

<400> SEQUENCE: 20
tttcgtacgc caccatggag tttgggctga gcatg                                     35

<210> SEQ ID NO 21
<211> LENGTH: 35
<212> TYPE: DNA
<213> ORGANISM: Homo sapiens

<400> SEQUENCE: 21
tttcgtacgc caccatgaaa cacctgtggt tcttc                                     35

<210> SEQ ID NO 22
<211> LENGTH: 35
<212> TYPE: DNA

<213> ORGANISM: Homo sapiens

<400> SEQUENCE: 22
tttcgtacgc caccatgggg tcaaccgcca tcctc                     35

<210> SEQ ID NO 23
<211> LENGTH: 6
<212> TYPE: PRT
<213> ORGANISM: Homo sapiens

<400> SEQUENCE: 23

Thr Val Thr Val Ser Ser
1               5

<210> SEQ ID NO 24
<211> LENGTH: 36
<212> TYPE: DNA
<213> ORGANISM: Homo sapiens

<400> SEQUENCE: 24
gtgccagtgg cagaggagtc cattcaagct taagtt                    36

<210> SEQ ID NO 25
<211> LENGTH: 5
<212> TYPE: PRT
<213> ORGANISM: Homo sapiens

<400> SEQUENCE: 25

Met Asp Met Arg Val
1               5

<210> SEQ ID NO 26
<211> LENGTH: 31
<212> TYPE: DNA
<213> ORGANISM: Homo sapiens

<400> SEQUENCE: 26
tttgtcgaca ccatggacat gagggtcctc c                         31

<210> SEQ ID NO 27
<211> LENGTH: 28
<212> TYPE: DNA
<213> ORGANISM: Homo sapiens

<400> SEQUENCE: 27
tttgtcgaca ccatggaagc cccagctc                             28

<210> SEQ ID NO 28
<211> LENGTH: 6
<212> TYPE: PRT
<213> ORGANISM: Homo sapiens

<400> SEQUENCE: 28

Thr Lys Val Asp Ile Lys
1               5

<210> SEQ ID NO 29
<211> LENGTH: 41
<212> TYPE: DNA
<213> ORGANISM: Homo sapiens

<400> SEQUENCE: 29
ctggtttcac ctatagtttg cattcagaat tcggcgcctt t              41

<210> SEQ ID NO 30
<211> LENGTH: 35
<212> TYPE: DNA
<213> ORGANISM: Homo sapiens

<400> SEQUENCE: 30
catctccaga gacaattcca agaacacgct gtatc            35

<210> SEQ ID NO 31
<211> LENGTH: 35
<212> TYPE: DNA
<213> ORGANISM: Homo sapiens

<400> SEQUENCE: 31
gtagaggtct ctgttaaggt tcttgtgcga catag            35

<210> SEQ ID NO 32
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Signal sequence for heavy chain variable region
      sequences as presented in original Figure 4

<400> SEQUENCE: 32

Met Gly Phe Gly Leu Ser Trp Val Phe Leu Val Ala Leu Leu Arg Gly
1               5                   10                  15

Val Gln Cys

<210> SEQ ID NO 33
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: Signal sequence for light chain variable region
      sequences as presented in original Figure 5

<400> SEQUENCE: 33

Met Glu Ala Pro Ala Gln Leu Leu Phe Leu Leu Leu Trp Leu Pro
1               5                   10                  15

Asp Thr Thr Gly
            20

<210> SEQ ID NO 34
<211> LENGTH: 428
<212> TYPE: DNA
<213> ORGANISM: Homo sapiens
<220> FEATURE:
<221> NAME/KEY: MISC_FEATURE
<223> OTHER INFORMATION: heavy chain variable region DNA sequences as
      presented in original Figure 2A-2B with coding sequence 1 to 421

<400> SEQUENCE: 34
atggggtttg ggctgagctg ggttttcctc gttgctcttt taagaggtgt ccagtgtcag     60
gtgcagctgg tggagtctgg gggaggcgtg gtccagcctg gaggtccct gagactctcc     120 tgtgcagcct ctggttcacc ttcagtagct atgctatgca ctgggtccgc caggctccgg    180
caaggggctg gagtgggtgg cagttatatc atatgatgga aaataaatac tacgcagact    240
ccgtgaaggg ccgattcacc atctagagac aattccaaga acacgctgta tctgcaaatg    300

```
aacagccaga gctgaggaca cggctgtgta ttactgtgcg agagatcgag gtatatcagc    360
aggtggaata ctactactac tacggtatgg acgtctgggg gcaagggacc acggtcaccg    420
tctcctca                                                             428

<210> SEQ ID NO 35
<211> LENGTH: 387
<212> TYPE: DNA
<213> ORGANISM: Homo sapiens
<220> FEATURE:
<221> NAME/KEY: MISC_FEATURE
<223> OTHER INFORMATION: light chain variable region DNA sequences as
      presented in original Figure 3 with coding sequence 1 to 387

<400> SEQUENCE: 35
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcaact ggcctccatt cactttcggc   360
cctgggacca agtggatat caaacgt                                         387

<210> SEQ ID NO 36
<211> LENGTH: 456
<212> TYPE: PRT
<213> ORGANISM: Homo sapiens
<220> FEATURE:
<221> NAME/KEY: MISC_FEATURE
<222> LOCATION: (1)..(456)
<223> OTHER INFORMATION: Golimumab Heavy Chain (HC)

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190
```

```
Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                    325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 37
<211> LENGTH: 215
<212> TYPE: PRT
<213> ORGANISM: Homo sapiens
<220> FEATURE:
<221> NAME/KEY: MISC_FEATURE
<222> LOCATION: (1)..(215)
<223> OTHER INFORMATION: Golimumab Light Chain (LC)

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Tyr Cys Gln Gln Arg Ser Asn Trp Pro Pro
            85                  90                      95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215
```

US 11,124,565 B2

METHOD FOR TREATING PRE-TYPE 1 DIABETES IN A HUMAN SUBJECT

FIELD OF THE INVENTION

The present invention relates to compositions and methods utilizing anti-TNF antibodies having a heavy chain (HC) comprising SEQ ID NO:36 and a light chain (LC) comprising SEQ ID NO:37 for use in the treatment or prevention of Type I Diabetes (T1D).

BACKGROUND OF THE INVENTION

TNF alpha is a soluble homotrimer of 17 kD protein subunits. A membrane-bound 26 kD precursor form of TNF also exists.

Cells other than monocytes or macrophages also produce TNF alpha. For example, human non-monocytic tumor cell lines produce TNF alpha and CD4+ and CD8+ peripheral blood T lymphocytes and some cultured T and B cell lines also produce TNF alpha.

TNF alpha causes pro-inflammatory actions which result in tissue injury, such as degradation of cartilage and bone, induction of adhesion molecules, inducing procoagulant activity on vascular endothelial cells, increasing the adherence of neutrophils and lymphocytes, and stimulating the release of platelet activating factor from macrophages, neutrophils and vascular endothelial cells.

TNF alpha has been associated with infections, immune disorders, neoplastic pathologies, autoimmune pathologies and graft-versus-host pathologies. The association of TNF alpha with cancer and infectious pathologies is often related to the host's catabolic state. Cancer patients suffer from weight loss, usually associated with anorexia.

The extensive wasting which is associated with cancer, and other diseases, is known as "cachexia". Cachexia includes progressive weight loss, anorexia, and persistent erosion of lean body mass in response to a malignant growth. The cachectic state causes much cancer morbidity and mortality. There is evidence that TNF alpha is involved in cachexia in cancer, infectious pathology, and other catabolic states.

TNF alpha is believed to play a central role in gram-negative sepsis and endotoxic shock, including fever, malaise, anorexia, and cachexia. Endotoxin strongly activates monocyte/macrophage production and secretion of TNF alpha and other cytokines. TNF alpha and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNF alpha increases in patients suffering from Gram-negative sepsis.

Thus, TNF alpha has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. Beneficial effects in open-label trials with a chimeric monoclonal antibody to TNF alpha (cA2) have been reported with suppression of inflammation and with successful retreatment after relapse in rheumatoid arthritis and in Crohn's disease. Beneficial results in a randomized, double-blind, placebo-controlled trial with cA2 have also been reported in rheumatoid arthritis with suppression of inflammation.

Other investigators have described mAbs specific for recombinant human TNF which had neutralizing activity in vitro. Some of these mAbs were used to map epitopes of human TNF and develop enzyme immunoassays and to assist in the purification of recombinant TNF. However, these studies do not provide a basis for producing TNF neutralizing antibodies that can be used for in vivo diagnostic or therapeutic uses in humans, due to immunogenicity, low specificity and/or pharmaceutical unsuitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems.

Putative receptor binding loci of hTNF has been disclosed and the receptor binding loci of TNF alpha as consisting of amino acids 11-13, 37-42, 49-57 and 155-157 of TNF have been disclosed.

Non-human mammalian, chimeric, polyclonal (e.g., antisera) and/or monoclonal antibodies (Mabs) and fragments (e.g., proteolytic digestion or fusion protein products thereof) are potential therapeutic agents that are being investigated in some cases to attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the readministration of the antibody or fragment. For example, repeated administration of antibodies or fragments comprising non-human portions can lead to serum sickness and/or anaphylaxis. In order to avoid these and other problems, a number of approaches have been taken to reduce the immunogenicity of such antibodies and portions thereof, including chimerization and humanization, as well known in the art. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins.

Accordingly, there is a need to provide anti-TNF antibodies or fragments that overcome one more of these problems, as well as improvements over known antibodies or fragments thereof.

SUMMARY OF THE INVENTION

The present invention provides isolated human, primate, rodent, mammalian, chimeric, humanized and/or CDR-grafted anti-TNF antibodies comprising all of the heavy chain variable CDR regions of SEQ ID NOS:1, 2 and 3 and/or all of the light chain variable CDR regions of SEQ ID NOS:4, 5 and 6, immunoglobulins, cleavage products and other specified portions and variants thereof, as well as anti-TNF alpha antibody compositions, encoding or complementary nucleic acids, vectors, host cells, compositions, formulations, devices, transgenic animals, transgenic plants, and methods of making and using thereof, as described and enabled herein, in combination with what is known in the art. These antibodies are described in U.S. Pat. No. 7,250,165 and related patents and applications in that family. The antibodies disclosed and claimed herein include the product designated Simponi®.

The present invention also provides at least one isolated anti-TNF antibody comprising all of the heavy chain variable CDR regions of SEQ ID NOS:1, 2 and 3 and/or all of the light chain variable CDR regions of SEQ ID NOS:4, 5 and 6 as described herein. An antibody according to the present invention includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention comprising all of the heavy chain variable CDR regions of SEQ ID NOS:1, 2 and 3 and/or all of the light chain variable CDR regions of SEQ ID NOS:4, 5 and 6. An antibody of the invention can include or be derived from any mammal, such as but not limited to a human, a mouse, a rabbit, a rat, a rodent, a primate, or any combination thereof, and the like.

The present invention provides, in one aspect, isolated nucleic acid molecules comprising, complementary, or hybridizing to, a polynucleotide encoding specific anti-TNF antibodies, comprising at least one specified sequence, domain, portion or variant thereof. The present invention further provides recombinant vectors comprising said anti-TNF antibody nucleic acid molecules, host cells containing such nucleic acids and/or recombinant vectors, as well as methods of making and/or using such antibody nucleic acids, vectors and/or host cells.

At least one antibody of the invention binds at least one specified epitope specific to at least one TNF protein, subunit, fragment, portion or any combination thereof. The at least one epitope can comprise at least one antibody binding region that comprises at least one portion of said protein, which epitope is preferably comprised of at least 1-5 amino acids of at least one portion thereof, such as but not limited to, at least one functional, extracellular, soluble, hydrophillic, external or cytoplasmic domain of said protein, or any portion thereof.

The at least one antibody can optionally comprise at least one specified portion of at least one complementarity determining region (CDR) (e.g., CDR1, CDR2 or CDR3 of the heavy or light chain variable region) and/or at least one constant or variable framework region or any portion thereof. The at least one antibody amino acid sequence can further optionally comprise at least one specified substitution, insertion or deletion as described herein or as known in the art.

The present invention also provides at least one isolated anti-TNF antibody as described herein, wherein the antibody has at least one activity, such as, but not limited to inhibition of TNF-induced cell adhesion molecules, inhibition of TNF binding to receptor, Arthritic index improvement in mouse model, (see, e.g., Examples 3-7). A(n) anti-TNF antibody can thus be screened for a corresponding activity according to known methods, such as but not limited to, at least one biological activity towards a TNF protein.

The present invention further provides at least one TNF anti-idiotype antibody to at least one TNF antibody of the present invention. The anti-idiotype antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention. An antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one TNF anti-idiotype antibody, comprising at least one specified sequence, domain, portion or variant thereof. The present invention further provides recombinant vectors comprising said TNF anti-idiotype antibody encoding nucleic acid molecules, host cells containing such nucleic acids and/or recombinant vectors, as well as methods of making and/or using such anti-idiotype antibody nucleic acids, vectors and/or host cells.

The present invention also provides at least one method for expressing at least one anti-TNF antibody, or TNF anti-idiotype antibody, in a host cell, comprising culturing a host cell as described herein under conditions wherein at least one anti-TNF antibody is expressed in detectable and/or recoverable amounts.

The present invention also provides at least one composition comprising (a) an isolated anti-TNF antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-TNF antibody method or composition, for administering a therapeutically effective amount to modulate or treat at least one TNF related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-TNF antibody, according to the present invention.

The present invention further provides at least one anti-TNF antibody method or composition, for diagnosing at least one TNF related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-TNF antibody, according to the present invention.

DESCRIPTION OF THE FIGURES

The patent or patent application file contains at least one drawing executed in color. Copy of this patent or patent application publication with color drawings will be provided by the United States Patent and Trademark Office upon request and payment of the necessary fees.

FIGS. 2A-B shows DNA sequences of the TNV mAb heavy chain variable regions. The germline gene shown is the DP-46 gene. 'TNVs' indicates that the sequence shown is the sequence of TNV14, TNV15, TNV148, and TNV196. The first three nucleotides in the TNV sequence define the translation initiation Met codon. Dots in the TNV mAb gene sequences indicate the nucleotide is the same as in the germline sequence. The first 19 nucleotides (underlined) of the TNV sequences correspond to the oligonucleotide used to PCR-amplify the variable region. An amino acid translation (single letter abbreviations) starting with the mature mAb is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb heavy chains use the J6 joining region.

FIG. 3 shows DNA sequences of the TNV mAb light chain variable regions. The germline gene shown is a representative member of the Vg/38K family of human kappa germline variable region genes. Dots in the TNV mAb gene sequences indicate the nucleotide is the same as in the germline sequence. The first 16 nucleotides (underlined) of the TNV sequences correspond to the oligonucleotide used to PCR-amplify the variable region. An amino acid translation of the mature mAb (single letter abbreviations) is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb light chains use the J3 joining sequence.

FIG. 4 shows deduced amino acid sequences of the TNV mAb heavy chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the DP-46 germline gene is shown on the top line for each domain. Dots indicate that the amino acid in the TNV mAb is identical to the germline gene. TNV148(B) indicates that the sequence shown pertains to both TNV148 and TNV148B. 'TNVs' indicates that the sequence shown pertains to all TNV mAbs unless a different sequence is shown. Dashes in the germline sequence (CDR3) indicate that the sequences are not known or do not exist in the germline gene.

FIG. 5 shows deduced amino acid sequences of the TNV mAb light chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the Vg/38K-type light chain germline gene is shown on the top line for each domain. Dots indicate that the amino acid in the TNV mAb is identical to the germline gene. TNV148(B) indicates that the sequence shown pertains to both TNV148 and TNV148B. 'All' indicates that the sequence shown pertains to TNV14, TNV15, TNV148, TNV148B, and TNV186.

FIG. 18 shows study schema for study CNTO148DML2001.

FIG. 19 shows simulated golimumab concentrations (median and 95% Prediction Interval) through Week 24 for various dosing regimens (without MTX) in virtual patients ages 6-21. Panel A: T1D (red) vs JIA (blue) and Panel B: T1D (red) vs pedUC (green).

FIG. 20 shows simulated Time Course for Free TNFα Suppression with Induction Period (1st month) in the left panel and Maintenance Period (through 6 months) in the right panel.

FIG. 21 shows features of the Ultrasafe.

FIG. 22 shows an illustration of the SIMPONI® VarioJect™ features.

FIG. 23 shows steps in the administration of the SIMPONI® using the VarioJect™ device.

FIG. 24 shows proposed design modifications to the VarioJect™ device.

DESCRIPTION OF THE INVENTION

Figure 1:
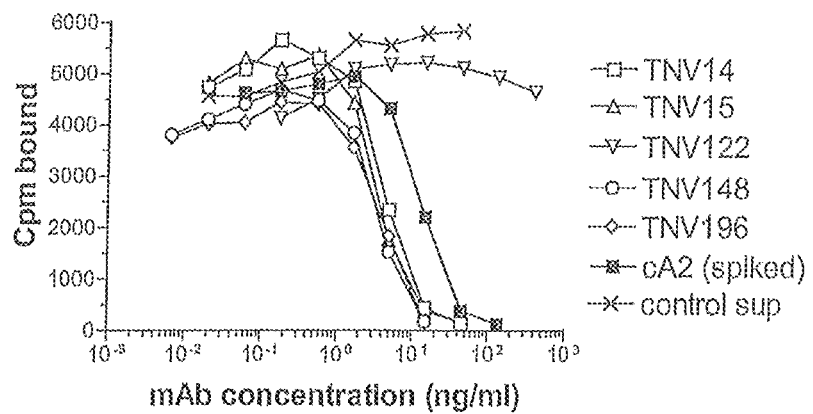
FIG. 1 shows a graphical representation showing an assay for ability of TNV mAbs in hybridoma cell supernatants to inhibit TNFα binding to recombinant TNF receptor. Varying amounts of hybridoma cell supernatants containing known amounts of TNV mAb were preincubated with a fixed concentration (5 ng/ml) of $^{125}$I-labeled TNFα. The mixture was transferred to 96-well Optiplates that had been previously coated with p55-sf2, a recombinant TNF receptor/IgG fusion protein. The amount of TNFα that bound to the p55 receptor in the presence of the mAbs was determined after washing away the unbound material and counting using a gamma counter. Although eight TNV mAb samples were tested in these experiments, for simplicity three of the mAbs that were shown by DNA sequence analyses to be identical to one of the other TNV mAbs (see Section 5.2.2) are not shown here. Each sample was tested in duplicate. The results shown are representative of two independent experiments.
Figure 6:
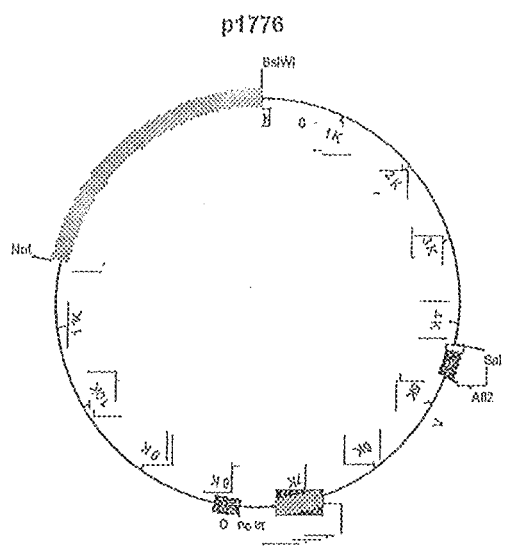
FIG. 6 shows schematic illustrations of the heavy and light chain expression plasmids used to make the rTNV148B-expressing C466 cells. p1783 is the heavy chain plasmid and p1776 is the light chain plasmid. The rTNV148B variable and constant region coding dom based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg. When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study.

The present invention provides isolated, recombinant and/or synthetic anti-TNF human, primate, rodent, mammalian, chimeric, humanized or CDR-grafted, antibodies comprising all of the heavy chain variable CDR regions of SEQ ID NOS:1, 2 and 3 and/or all of the light chain variable CDR regions of SEQ ID NOS:4, 5 and 6 and TNF anti-idiotype antibodies thereto, as well as compositions and encoding nucleic acid molecules comprising at least one polynucleotide encoding at least one anti-TNF antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-tumor necrosis factor alpha antibody," "anti-TNF antibody," "anti-TNF antibody portion," or "anti-TNF antibody fragment" and/or "anti-TNF antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an TNF receptor or binding protein, which can be incorporated into an antibody of the present invention. Such antibody optionally further affects a specific ligand, such as but not limited to where such antibody modulates, decreases, increases, antagonizes, angonizes, mitigates, alleviates, blocks, inhibits, abrogates and/or interferes with at least one TNF activity or binding, or with TNF receptor activity or binding, in vitro, in situ and/or in vivo. As a non-limiting example, a suitable anti-TNF antibody, specified portion or variant of the present invention can bind at least one TNF, or specified portions, variants or domains thereof. A suitable anti-TNF antibody, specified portion, or variant can also optionally affect at least one of TNF activity or function, such as but not limited to, RNA, DNA or protein synthesis, TNF release, TNF receptor signaling, membrane TNF cleavage, TNF activity, TNF production and/or synthesis. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian TNF. For example, antibody fragments capable of binding to TNF or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one TNF protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-TNF antibodies (also termed TNF antibodies) useful in the methods and compositions of the present invention can optionally be characterized by high affinity binding to TNF and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference).

Utility:

The isolated nucleic acids of the present invention can be used for production of at least one anti-TNF antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one TNF condition, selected from, but not limited to, at least one of an immune disorder or disease, a cardiovascular disorder or disease, an infectious, malignant, and/or neurologic disorder or disease.

Such a method can comprise administering an effective amount of a composition or a pharmaceutical composition comprising at least one anti-TNF antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts. Citations. All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Antibodies of the Present Invention:

At least one anti-TNF antibody of the present invention comprising all of the heavy chain variable CDR regions of SEQ ID NOS:1, 2 and 3 and/or all of the light chain variable CDR regions of SEQ ID NOS:4, 5 and 6 can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

Human antibodies that are specific for human TNF proteins or fragments thereof can be raised against an appropriate immunogenic antigen, such as isolated and/or TNF protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www._atcc.org, www._lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/

GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www._ncbi.nlm.nih.gov/entrez/query.fcgi; www._atcc.org/phage/hdb.html; www._sciquest.com/; www._abcam.com/; www._antibodyresource-.com/onlinecomp.html; www._public.iastate.edu/~pedro/research_tools.html; www._mgen.uni-heidelberg.de/SD/IT/IT.html; www._whfreeman.com/immunology/CH05/kuby05.htm; www._library.thinkquest.org/12429/Immune/Antibody.html; www.hhmi.org/grants/lectures/1996/vlab/; www._path.cam.ac.uk/~mrc7/mikeimages.html; www._antibodyresource.com/; mcb.harvard.edu/BioLinks/Immunology.html.www._immunologylink.com/; pathbox.wustl.edu/~hcenter/index.html; www._biotech.ufl.edu/~hcF; www._pebio.com/pa/340913/340913.html; www._nal.usda.gov/awic/pubs/antibody/; www._m.ehime-u.acjp/~yasuhito/Elisa.html; www._biodesign.com/table.asp; www._icnet.uk/axp/facs/davies/links.html; www.biotech.ufl.edu/~fccl/protocol.html; www._isac-net.org/sites geo.html; aximtl.imt.uni-marburg.de/~rek/AEPStart.html; baserv.uci.kun.nl/~jraats/linksl.html; www._recab.unihd.de/immuno.bme.nwu.edu/; www._mrc-cpe.cam.ac.uk/imt-doc/public/INTRO.html; www._ibt.unam.mx/vir/V_mice.html; imgt.cnusc.fr:8104/; www.biochem.ucl.ac.uk/~martin/abs/index.html; antibody.bath.ac.uk/; www.abgen.cvm.tamu.edu/lab/wwwabgen.html; www.unizh.ch/~honegger/AHOseminar/Slide01.html; www.cryst.bbk. ac.uk/~ubcg07s/; www.nimr.mrc.ac.uk/CC/ccaewg/ccaewg.htm; www.path.cam.ac.uk/~mrc7/humanisation/TAHHP.html; www.ibt.unam.mx/viestructure/stat_aim.html; www.biosci.missouri.edu/smithgp/index.html; www.cryst.bioc.cam.ac.uk/~fmolina/Webpages/Pept/spottech.html; www.jerini.de/frproducts.html; www.patents.ibm.com/ibm.html.Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The anti-TNF antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-TNF antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643, 768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies of the present invention can also be prepared using at least one anti-TNF antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-TNF antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109: 341-6 (1995); Whitelam et al., Biochem. Soc. Trans. 22:940-944 (1994); and references cited therein. See, also generally for plant expression of antibodies, but not limited to, each of the above references is entirely incorporated herein by reference.

The antibodies of the invention can bind human TNF with a wide range of affinities ($K_D$). In a preferred embodiment, at least one human mAb of the present invention can optionally bind human TNF with high affinity. For example, a human mAb can bind human TNF with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules.

Using the information provided herein, such as the nucleotide sequences encoding at least 70-100% of the contiguous amino acids of at least one of SEQ ID NOS:1, 2, 3, 4, 5, 6, 7, 8, specified fragments, variants or consensus sequences thereof, or a deposited vector comprising at least one of these sequences, a nucleic acid molecule of the present invention encoding at least one anti-TNF antibody comprising all of the heavy chain variable CDR regions of SEQ ID NOS:1, 2 and 3 and/or all of the light chain variable CDR regions of SEQ ID NOS:4, 5 and 6 can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS:1-3) or light chain (e.g., SEQ ID NOS: 4-6); nucleic acid molecules comprising the coding sequence for an anti-TNF antibody or variable region (e.g., SEQ ID NOS:7,8); and nucleic acid molecules which comprise a nucleotide sequence substantially different from those described above but which, due to the degeneracy of the genetic code, still encode at least one anti-TNF antibody as described herein and/or as known in the art. Of course, the genetic code is well known in the art. Thus, it would be routine for one skilled in the art to generate such degenerate nucleic acid variants that code for specific anti-TNF antibodies of the present invention. See, e.g., Ausubel, et al., supra, and such nucleic acid variants are included in the present invention. Non-limiting examples of isolated nucleic acid molecules of the present invention include SEQ ID NOS:10, 11, 12, 13, 14, 15, corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an anti-TNF antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide as Described Herein.

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids.

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids.

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Nucleic Acid Screening and Isolation Methods.

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids.

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes.

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells.

The present invention also relates to vectors that include isolated nucleic acid molecules of the present invention, host cells that are genetically engineered with the recombinant vectors, and the production of at least one anti-TNF antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www._atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www._atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody.

An anti-TNF antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-TNF Antibodies

The isolated antibodies of the present invention, comprising all of the heavy chain variable CDR regions of SEQ ID NOS:1, 2 and 3 and/or all of the light chain variable CDR regions of SEQ ID NOS:4, 5 and 6, comprise antibody amino acid sequences disclosed herein encoded by any suitable polynucleotide, or any isolated or prepared antibody. Preferably, the human antibody or antigen-binding fragment binds human TNF and, thereby partially or substantially neutralizes at least one biological activity of the protein. An antibody, or specified portion or variant thereof, that partially or preferably substantially neutralizes at least one biological activity of at least one TNF protein or fragment can bind the protein or fragment and thereby inhibit activitys mediated through the binding of TNF to the TNF receptor or through other TNF-dependent or mediated mechanisms. As used herein, the term "neutralizing antibody" refers to an antibody that can inhibit an TNF-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-TNF antibody to inhibit an TNF-dependent activity is preferably assessed by at least one suitable TNF protein or receptor assay, as described herein and/or as known in the art. A human antibody of the invention can be of any class (IgG, IgA, IgM, IgE, IgD, etc.) or isotype and can comprise a kappa or lambda light chain.

In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other trangenic non-human mammal comprising at least one human light chain (e.g., IgG, IgA☐ and IgM (e.g., γ1, γ2, γ3, γ4) transgenes as described herein and/or as known in the art. In another embodiment, the anti-human TNF human antibody comprises an IgG1 heavy chain and a IgG1 light chain.

At least one antibody of the invention binds at least one specified epitope specific to at least one TNF protein, subunit, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The at least one specified epitope can comprise any combination of at least one amino acid sequence of at least 1-3 amino acids to the entire specified portion of contiguous amino acids of the SEQ ID NO:9.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS:1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the antibody or antigen-binding fragment have the amino acid sequence of the corresponding CDR of at least one of mAb TNV148, TNV14, TNV15, TNV196, TNV118, TNV32, TNV86, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-TNF antibody can comprise at least one of a heavy or light chain variable region having a defined amino acid sequence. For example, in a preferred embodiment, the anti-TNF antibody comprises at least one of heavy chain variable region, optionally having the amino acid sequence of SEQ ID NO:7 and/or at least one light chain variable region, optionally having the amino acid sequence of SEQ ID NO:8. antibodies that bind to human TNF and that comprise a defined heavy or light chain variable region can be prepared using suitable methods, such as phage display (Katsube, Y., et al., *Int J Mol. Med*, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human TNF or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human TNF with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes.

The amino acids that make up anti-TNF antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
| --- | --- | --- | --- |
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |

| SINGLE LETTER CODE | THREE LETTER CODE | NAME | THREE NUCLEOTIDE CODON(S) |
|---|---|---|---|
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-TNF antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-TNF antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-TNF antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one TNF neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-TNF antibodies of the present invention can include, but are not limited to, at least one portion, sequence or combination selected from 1 to all of the contiguous amino acids of at least one of SEQ ID NOS:1, 2, 3, 4, 5, 6.

A(n) anti-TNF antibody can further optionally comprise a polypeptide of at least one of 70-100% of the contiguous amino acids of at least one of SEQ ID NOS:7, 8.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10-100% of the number of contiguous residues in an anti-TNF antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-1000% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

Anti-Idiotype Antibodies to Anti-Tnf Antibody Compositions.

In addition to monoclonal or chimeric anti-TNF antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Anti-Tnf Antibody Compositions.

The present invention also provides at least one anti-TNF antibody composition comprising at least one, at least two, at least three, at least four, at least five, at least six or more anti-TNF antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-TNF antibody amino acid sequence selected from the group consisting of 70-100% of the contiguous amino acids of SEQ ID NOS:1, 2, 3, 4, 5, 6, 7, 8, or specified fragments, domains or variants thereof. Preferred anti-TNF antibody compositions include at least one or two full length, fragments, domains or variants as at least one CDR or LBR containing portions of the anti-TNF antibody sequence of 70-100% of SEQ ID NOS:1, 2, 3, 4, 5, 6, or specified fragments, domains or variants thereof. Further preferred compositions comprise 40-99% of at least one of 70-100% of SEQ ID NOS:1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-TNF antibody compositions of the present invention can further comprise at least one of any suitable and effective amount of a composition or pharmaceutical composition comprising at least one anti-TNF antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium difficile, Clostridium botulinum*), *Camphlobacter* species (e.g., *Camphlobacter jejuni, Camphlobacter fetus*), *Heliocbacter* species, (e.g., *Heliocbacter pylori*), *Aeromonas* species (e.g., *Aeromonas sobria, Aeromonas hydrophila, Aeromonas caviae*), *Pleisomonas shigelloides, Yersinia enterocolitica, Vibrio* species (e.g., *Vibrio cholerae, Vibrio parahemolyticus*), *Klebsiella* species, *Pseudomonas aeruginosa,* and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-TNF antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* 18th Edition, Mack Publishing Co. (Easton, Pa.) 1990. Pharmaceutically acceptable carriers can be routinely selected that are suitable for the mode of administration, solubility and/or stability of the anti-TNF antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-TNF antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromthamine hydrochloride, or phosphate buffers. Preferred buffers for use in the present compositions are organic acid salts such as citrate.

Additionally, anti-TNF antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-TNF antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations.

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-TNF antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-TNF antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-TNF antibody, and a second vial comprising an aqueous diluent of prescribed buffer or preservative, wherein said packaging material comprises a label that instructs a patient to reconstitute the at least one anti-TNF antibody in the aqueous diluent to form a solution that can be held over a period of twenty-four hours or greater.

The at least one anti-TNF antibody used in accordance with the present invention can be produced by recombinant means, including from mammalian cell or transgenic preparations, or can be purified from other biological sources, as described herein or as known in the art.

The range of at least one anti-TNF antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyols, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-TNF antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-TNF antibody and preservative in an aqueous diluent is carried out using conventional dissolution and mixing procedures. To prepare a suitable formulation, for example, a measured amount of at least one anti-TNF antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-TNF antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-TNF antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-TNF antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-TNF antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-TNF antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-TNF antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-TNF antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-TNF antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications.

The present invention also provides a method for modulating or treating at least one TNF related disease, in a cell, tissue, organ, animal, or patient, as known in the art or as described herein, using at least one dual integrin antibody of the present invention.

The present invention also provides a method for modulating or treating at least one TNF related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aortic and peripheral aneuryisms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphedema, lipedema, unstable angina, reperfusion injury, post pump syndrome, ischemia-reperfusion injury, and the like. Such a method can optionally comprise administering an effective amount of a composition or pharmaceutical composition comprising at least one anti-TNF antibody to a cell, tissue, organ, animal or patient in need of such modulation, treatment or therapy.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *Mycobacterium tuberculosis, Mycobacterium avium* intracellulare, Pneumocystis carinii pneumonia, pelvic inflammatory disease, orchitis/epydimitis, *legionella*, lyme disease, influenza a, epstein-barr virus, viral-associated hemaphagocytic syndrome, vital encephalitis/aseptic meningitis, and the like.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasiaa, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992)

Any method of the present invention can comprise administering an effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10}$ M$^{-1}$. Preferred methods for determining monoclonal antibody specificity and affinity by competitive inhibition can be found in Harlow, et al., *antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2000); Kozbor et al., *Immunol. Today*, 4:72-79 (1983); Ausubel et al., eds. *Current Protocols in Molecular Biology*, Wiley Interscience, New York (1987-2000); and Muller, *Meth. Enzymol.*, 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules.

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNF □ with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2000).

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments.

Any method of the present invention can comprise a method for treating a TNF mediated disorder, comprising administering an effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist.

Typically, treatment of pathologic conditions is effected by administering an effective amount or dosage of at least one anti-TNF antibody composition that total, on average, a range from at least about 0.01 to 500 milligrams of at least one anti-TNF antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 μg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration.

Many known and developed modes of administration can be used according to the present invention for administering pharmaceutically effective amounts of at least one anti-TNF antibody according to the present invention. While pulmonary administration is used in the following description, other modes of administration can be used according to the present invention with suitable results.

TNF antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery.

The invention further relates to the administration of at least one anti-TNF antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-TNF antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration.

For pulmonary administration, preferably at least one anti-TNF antibody composition is delivered in a particle size effective for reaching the lower airways of the lung or sinuses. According to the invention, at least one anti-TNF antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention and are not intended as limiting the scope of the invention. Preferably, a composition comprising at least one anti-TNF antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1-5 µm, for good respirability.

Administration of TNF Antibody Compositions as a Spray.

A spray including TNF antibody composition protein can be produced by forcing a suspension or solution of at least one anti-TNF antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-TNF antibody composition protein delivered by a sprayer have a particle size less than about 10 µm, preferably in the range of about 1 µm to about 5 µm, and most preferably about 2 µm to about 3 µm.

Formulations of at least one anti-TNF antibody composition protein suitable for use with a sprayer typically include antibody composition protein in an aqueous solution at a concentration of about 0.1 mg to about 100 mg of at least one anti-TNF antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as TNF antibodies, or specified portions or variants, can also be included in the formulation.

Administration of TNF antibody compositions by a Nebulizer.

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 μm, preferably in the range of about 1 μm to about 5 μm, and most preferably about 2 μm to about 3 μm.

Formulations of at least one anti-TNF antibody suitable for use with a nebulizer, either jet or ultrasonic, typically include a concentration of about 0.1 mg to about 100 mg of at least one anti-TNF antibody protein per ml of solution. The formulation can include agents such as an excipient, a buffer, an isotonicity agent, a preservative, a surfactant, and, preferably, zinc. The formulation can also include an excipient or agent for stabilization of the at least one anti-TNF antibody composition protein, such as a buffer, a reducing agent, a bulk protein, or a carbohydrate. Bulk proteins useful in formulating at least one anti-TNF antibody composition proteins include albumin, protamine, or the like. Typical carbohydrates useful in formulating at least one anti-TNF antibody include sucrose, mannitol, lactose, trehalose, glucose, or the like. The at least one anti-TNF antibody formulation can also include a surfactant, which can reduce or prevent surface-induced aggregation of the at least one anti-TNF antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of TNF Antibody Compositions by a Metered Dose Inhaler.

In a metered dose inhaler (MDI), a propellant, at least one anti-TNF antibody, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-TNF antibody for use with a metered-dose inhaler device will generally include a finely divided powder containing at least one anti-TNF antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-TNF antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one anti-TNF antibody compositions via devices not described herein.

Oral Formulations and Administration.

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 55,871,753 are used to deliver biologically active agents orally are known in the art.

Mucosal Formulations and Administration.

For absorption through mucosal surfaces, compositions and methods of administering at least one anti-TNF antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration.

For transdermal administration, the at least one anti-TNF antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations.

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/ polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

Example 1: Cloning and Expression of TNF Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells.

The vector pC4 is used for the expression of TNF antibody. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can be used to express the TNF in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Example 2: Generation of High Affinity Human IgG Monoclonal Antibodies Reactive with Human TNF Using Transgenic Mice Summary Transgenic mice have been used that contain human heavy and light chain immunoglobulin genes to generate high affinity, completely human, monoclonal antibodies that can be used therapeutically to inhibit the action of TNF for the treatment of one or more TNF-mediated disease. (CBA/J×C57/BL6/J) $F_2$ hybrid mice containing human variable and constant region antibody transgenes for both heavy and light chains are immunized with human recombinant TNF (Taylor et al., Intl. Immunol. 6:579-591 (1993); Lonberg, et al., Nature 368:856-859 (1994); Neuberger, M., Nature Biotech. 14:826 (1996); Fishwild, et al., Nature Biotechnology 14:845-851 (1996)). Several fusions yielded one or more panels of completely human TNF reactive IgG monoclonal antibodies. The completely human anti-TNF antibodies are further characterized. All are IgG1κ. Such antibodies are found to have affinity constants somewhere between $1 \times 10^9$ and $9 \times 10^{12}$. The unexpectedly high affinities of these fully human monoclonal antibodies make them suitable candidates for therapeutic applications in TNF related diseases, pathologies or disorders.

Abbreviations

BSA—bovine serum albumin; $CO_2$—carbon dioxide; DMSO—dimethyl sulfoxide; EIA—enzyme immunoassay; FBS—fetal bovine serum; $H_2O_2$—hydrogen peroxide; HRP—horseradish peroxidase; ID—interadermal; Ig—immunoglobulin; TNF—tissue necrosis factor alpha; IP—intraperitoneal; IV—intravenous; Mab—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; v/v—volume per volume; w/v—weight per volume.

Materials and Methods.

Animals.

Transgenic mice that can express human antibodies are known in the art (and are commercially available (e.g., from GenPharm International, San Jose, Calif.; Abgenix, Freemont, Calif., and others) that express human immunoglobulins but not mouse IgM or Igκ. For example, such transgenic mice contain human sequence transgenes that undergo V(D)J joining, heavy-chain class switching, and somatic mutation to generate a repertoire of human sequence immunoglobulins (Lonberg, et al., Nature 368:856-859 (1994)). The light chain transgene can be derived, e.g., in part from a yeast artificial chromosome clone that includes nearly half of the germline human Vκ region. In addition, the heavy-chain transgene can encode both human μ and human γ1 (Fishwild, et al., Nature Biotechnology 14:845-851 (1996)) and/or γ3 constant regions. Mice derived from appropriate genotopic lineages can be used in the immunization and fusion processes to generate fully human monoclonal antibodies to TNF.

Immunization.

One or more immunization schedules can be used to generate the anti-TNF human hybridomas. The first several fusions can be performed after the following exemplary immunization protocol, but other similar known protocols can be used. Several 14-20 week old female and/or surgically castrated transgenic male mice are immunized IP and/or ID with 1-1000 μg of recombinant human TNF emulsified with an equal volume of TITERMAX or complete Freund's adjuvant in a final volume of 100-400 μL (e.g., 200). Each mouse can also optionally receive 1-10 μg in 100 μL physiological saline at each of 2 SQ sites. The mice can then be immunized 1-7, 5-12, 10-18, 17-25 and/or 21-34 days later IP (1-400 μg) and SQ (1-400 μg×2) with TNF emulsified with an equal volume of TITERMAX or incomplete Freund's adjuvant. Mice can be bled 12-25 and 25-40 days later by retro-orbital puncture without anticoagulant. The blood is then allowed to clot at RT for one hour and the serum is collected and titered using an TNF EIA assay according to known methods. Fusions are performed when repeated injections do not cause titers to increase. At that time, the mice can be given a final IV booster injection of 1-400 μg TNF diluted in 100 μL physiological saline. Three days later, the mice can be euthanized by cervical dislocation and the spleens removed aseptically and immersed in 10 mL of cold phosphate buffered saline (PBS) containing 100 U/mL penicillin, 100 μg/mL streptomycin, and 0.25 μg/mL amphotericin B (PSA). The splenocytes are harvested by sterilely perfusing the spleen with PSA-PBS. The cells are washed once in cold PSA-PBS, counted using Trypan blue dye exclusion and resuspended in RPMI 1640 media containing 25 mM Hepes.

Cell Fusion.

Fusion can be carried out at a 1:1 to 1:10 ratio of murine myeloma cells to viable spleen cells according to known methods, e.g., as known in the art. As a non-limiting example, spleen cells and myeloma cells can be pelleted together. The pellet can then be slowly resuspended, over 30 seconds, in 1 mL of 50% (w/v) PEG/PBS solution (PEG molecular weight 1,450, Sigma) at 37°C. The fusion can then be stopped by slowly adding 10.5 mL of RPMI 1640 medium containing 25 mM Hepes (37°C) over 1 minute. The fused cells are centrifuged for 5 minutes at 500-1500 rpm. The cells are then resuspended in HAT medium (RPMI 1640 medium containing 25 mM Hepes, 10% Fetal Clone I serum (Hyclone), 1 mM sodium pyruvate, 4 mM L-glutamine, 10 μg/mL gentamicin, 2.5% Origen culturing supplement (Fisher), 10% 653-conditioned RPMI 1640/Hepes media, 50 μM 2-mercaptoethanol, 100 μM hypoxanthine, 0.4 μM aminopterin, and 16 μM thymidine) and then plated at 200 μL/well in fifteen 96-well flat bottom tissue culture plates. The plates are then placed in a humidified 37°C incubator containing 5% $CO_2$ and 95% air for 7-10 days.

Detection of Human IgG Anti-TNF Antibodies in Mouse Serum.

Solid phase EIA's can be used to screen mouse sera for human IgG antibodies specific for human TNF. Briefly, plates can be coated with TNF at 2 μg/mL in PBS overnight. After washing in 0.15M saline containing 0.02% (v/v) Tween 20, the wells can be blocked with 1% (w/v) BSA in PBS, 200 μL/well for 1 hour at RT. Plates are used immediately or frozen at −20°C for future use. Mouse serum dilutions are incubated on the TNF coated plates at 50 μL/well at RT for 1 hour. The plates are washed and then probed with 50 μL/well HRP-labeled goat anti-human IgG, Fc specific diluted 1:30,000 in 1% BSA-PBS for 1 hour at RT. The plates can again be washed and 100 μL/well of the citrate-phosphate substrate solution (0.1M citric acid and 0.2M sodium phosphate, 0.01% $H_2O_2$ and 1 mg/mL OPD) is added for 15 minutes at RT. Stop solution (4N sulfuric acid) is then added at 25 μL/well and the OD's are read at 490 nm via an automated plate spectrophotometer.

Detection of Completely Human Immunoglobulins in Hybridoma Supernates.

Growth positive hybridomas secreting fully human immunoglobulins can be detected using a suitable EIA. Briefly, 96 well pop-out plates (VWR, 610744) can be coated with 10 μg/mL goat anti-human IgG Fc in sodium carbonate buffer overnight at 4°C. The plates are washed and blocked with 1% BSA-PBS for one hour at 37° C. and used immediately or frozen at −20°C. Undiluted hybridoma supernatants are incubated on the plates for one hour at 37° C. The plates are washed and probed with HRP labeled goat anti-human kappa diluted 1:10,000 in 1% BSA-PBS for one hour at 37° C. The plates are then incubated with substrate solution as described above.

Determination of Fully Human Anti-TNF Reactivity.

Hybridomas, as above, can be simultaneously assayed for reactivity to TNF using a suitable RIA or other assay. For example, supernatants are incubated on goat anti-human IgG Fc plates as above, washed and then probed with radiolabled TNF with appropriate counts per well for 1 hour at RT. The wells are washed twice with PBS and bound radiolabled TNF is quantitated using a suitable counter.

Human IgG1κ anti-TNF secreting hybridomas can be expanded in cell culture and serially subcloned by limiting dilution. The resulting clonal populations can be expanded and cryopreserved in freezing medium (95% FBS, 5% DMSO) and stored in liquid nitrogen.

Isotyping.

Isotype determination of the antibodies can be accomplished using an EIA in a format similar to that used to screen the mouse immune sera for specific titers. TNF can be coated on 96-well plates as described above and purified antibody at 2 μg/mL can be incubated on the plate for one hour at RT. The plate is washed and probed with HRP labeled goat anti-human $IgG_1$ or HRP labeled goat anti-human IgG3 diluted at 1:4000 in 1% BSA-PBS for one hour at RT. The plate is again washed and incubated with substrate solution as described above.

Binding Kinetics of Human Anti-Human TNF Antibodies with Human TNF.

Binding characteristics for antibodies can be suitably assessed using an TNF capture EIA and BIAcore technology, for example. Graded concentrations of purified human TNF antibodies can be assessed for binding to EIA plates coated with 2 μg/mL of TNF in assays as described above. The OD's can be then presented as semi-log plots showing relative binding efficiencies.

Quantitative binding constants can be obtained, e.g., as follows, or by any other known suitable method. A BIAcore CM-5 (carboxymethyl) chip is placed in a BIAcore 2000 unit. HBS buffer (0.01 M HEPES, 0.15 M NaCl, 3 mM EDTA, 0.005% v/v P20 surfactant, pH 7.4) is flowed over a flow cell of the chip at 5 µL/minute until a stable baseline is obtained. A solution (100 µL) of 15 mg of EDC (N-ethyl-N'-(3-dimethyl-aminopropyl)-carbodiimide hydrochloride) in 200 µL water is added to 100 µL of a solution of 2.3 mg of NHS (N-hydroxysuccinimide) in 200 µL water. Forty (40) µL of the resulting solution is injected onto the chip. Six µL of a solution of human TNF (15 µg/mL in 10 mM sodium acetate, pH 4.8) is injected onto the chip, resulting in an increase of ca. 500 RU. The buffer is changed to TBS/Ca/Mg/BSA running buffer (20 mM Tris, 0.15 M sodium chloride, 2 mM calcium chloride, 2 mM magnesium acetate, 0.5% Triton X-100, 25 µg/mL BSA, pH 7.4) and flowed over the chip overnight to equilibrate it and to hydrolyze or cap any unreacted succinimide esters.

Antibodies are dissolved in the running buffer at 33.33, 16.67, 8.33, and 4.17 nM. The flow rate is adjusted to 30 µL/min and the instrument temperature to 25°C. Two flow cells are used for the kinetic runs, one on which TNF had been immobilized (sample) and a second, underivatized flow cell (blank). 120 µL of each antibody concentration is injected over the flow cells at 30 µL/min (association phase) followed by an uninterrupted 360 seconds of buffer flow (dissociation phase). The surface of the chip is regenerated (tissue necrosis factor alpha/antibody complex dissociated) by two sequential injections of 30 µL each of 2 M guanidine thiocyanate.

Analysis of the data is done using BIA evaluation 3.0 or CLAMP 2.0, as known in the art. For each antibody concentration the blank sensogram is subtracted from the sample sensogram. A global fit is done for both dissociation ($k_d$, sec$^{-1}$) and association ($k_a$, mol$^{-1}$ sec$^{-1}$) and the dissociation constant ($K_D$, mol) calculated ($k_d/k_a$). Where the antibody affinity is high enough that the RUs of antibody captured are >100, additional dilutions of the antibody are run.

Results and Discussion.

Generation of Anti-Human TNF Monoclonal Antibodies.

Several fusions are performed and each fusion is seeded in 15 plates (1440 wells/fusion) that yield several dozen antibodies specific for human TNF. Of these, some are found to consist of a combination of human and mouse Ig chains. The remaining hybridomas secret anti-TNF antibodies consisting solely of human heavy and light chains. Of the human hybridomas all are expected to be IgG1κ.

Binding Kinetics of Human Anti-Human TNF Antibodies.

ELISA analysis confirms that purified antibody from most or all of these hybridomas bind TNF in a concentration-dependent manner. FIGS. 1-2 show the results of the relative binding efficiency of these antibodies. In this case, the avidity of the antibody for its cognate antigen (epitope) is measured. It should be noted that binding TNF directly to the EIA plate can cause denaturation of the protein and the apparent binding affinities cannot be reflective of binding to undenatured protein. Fifty percent binding is found over a range of concentrations.

Quantitative binding constants are obtained using BIAcore analysis of the human antibodies and reveals that several of the human monoclonal antibodies are very high affinity with $K_D$ in the range of $1 \times 10^{-9}$ to $7 \times 10^{-12}$.

Conclusions.

Several fusions are performed utilizing splenocytes from hybrid mice containing human variable and constant region antibody transgenes that are immunized with human TNF. A set of several completely human TNF reactive IgG monoclonal antibodies of the IgG1κ isotype are generated. The completely human anti-TNF antibodies are further characterized. Several of generated antibodies have affinity constants between $1 \times 10^9$ and $9 \times 10^{12}$. The unexpectedly high affinities of these fully human monoclonal antibodies make them suitable for therapeutic applications in TNF-dependent diseases, pathologies or related conditions.

Example 3: Generation of Human IgG Monoclonal Antibodies Reactive to Human TNFα

Summary (CBA/J×C57BL/6J) $F_2$ hybrid mice (1-4) containing human variable and constant region antibody transgenes for both heavy and light chains were immunized with recombinant human TNFα. One fusion, named GenTNV, yielded eight totally human IgG1κ monoclonal antibodies that bind to immobilized recombinant human TNFα. Shortly after identification, the eight cell lines were transferred to Molecular Biology for further characterization. As these Mabs are totally human in sequence, they are expected to be less immunogenic than cA2 (Remicade) in humans.

Abbreviations

BSA—bovine serum albumin; $CO_2$—carbon dioxide; DMSO—dimethyl sulfoxide; EIA—enzyme immunoassay; FBS—fetal bovine serum; $H_2O_2$—hydrogen peroxide; HC—heavy chain; HRP—horseradish peroxidase; ID—interadermal; Ig—immunoglobulin; TNF—tissue necrosis factor alpha; IP—intraperitoneal; IV—intravenous; Mab—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; TNFα—tumor necrosis factor alpha; v/v—volume per volume; w/v—weight per volume.

Introduction

Transgenic mice that contain human heavy and light chain immunoglobulin genes were utilized to generate totally human monoclonal antibodies that are specific to recombinant human TNFα. It is hoped that these unique antibodies can be used, as cA2 (Remicade) is used to therapeutically inhibit the inflammatory processes involved in TNFα-mediated disease with the benefit of increased serum half-life and decreased side effects relating to immunogenicity.

Materials and Methods.

Animals.

Transgenic mice that express human immunoglobulins, but not mouse IgM or Igκ, have been developed by GenPharm International. These mice contain functional human antibody transgenes that undergo V(D)J joining, heavy-chain class switching and somatic mutation to generate a repertoire of antigen-specific human immunoglobulins (1). The light chain transgenes are derived in part from a yeast artificial chromosome clone that includes nearly half of the germline human Vκ locus. In addition to several VH genes, the heavy-chain (HC) transgene encodes both human µ and human γ1 (2) and/or γ3 constant regions. A mouse derived from the HCo12/KCo5 genotypic lineage was used in the immunization and fusion process to generate the monoclonal antibodies described here.

Purification of Human TNFα.

Human TNFα was purified from tissue culture supernatant from C237A cells by affinity chromatography using a column packed with the TNFα receptor-Fc fusion protein (p55-sf2) (5) coupled to Sepharose 4B (Pharmacia). The cell supernatant was mixed with one-ninth its volume of 10× Dulbecco's PBS (D-PBS) and passed through the column at 4° C. at 4 mL/min. The column was then washed with PBS and the TNFα was eluted with 0.1 M sodium citrate, pH 3.5 and neutralized with 2 M Tris-HCl pH 8.5. The purified TNFα was buffer exchanged into 10 mM Tris, 0.12 M sodium chloride pH 7.5 and filtered through a 0.2 um syringe filter.

Immunizations.

A female GenPharm mouse, approximately 16 weeks old, was immunized IP (200 μL) and ID (100 μL at the base of the tail) with a total of 100 μg of TNFα (lot JG102298 or JG102098) emulsified with an equal volume of Titermax adjuvant on days 0, 12 and 28. The mouse was bled on days 21 and 35 by retro-orbital puncture without anti-coagulant. The blood was allowed to clot at RT for one hour and the serum was collected and titered using TNFα solid phase EIA assay. The fusion, named GenTNV, was performed after the mouse was allowed to rest for seven weeks following injection on day 28. The mouse, with a specific human IgG titer of 1:160 against TNFα, was then given a final IV booster injection of 50 μg TNFα diluted in 100 μL physiological saline. Three days later, the mouse was euthanized by cervical dislocation and the spleen was removed aseptically and immersed in 10 mL of cold phosphate-buffered saline (PBS) containing 100 U/mL penicillin, 100 μg/mL streptomycin, and 0.25 μg/mL amphotericin B (PSA). The splenocytes were harvested by sterilely perfusing the spleen with PSA-PBS. The cells were washed once in cold PSA-PBS, counted using a Coulter counter and resuspended in RPMI 1640 media containing 25 mM Hepes.

Cell Lines.

The non-secreting mouse myeloma fusion partner, 653 was received into Cell Biology Services (CBS) group on May 14, 1997 from Centocor's Product Development group. The cell line was expanded in RPMI medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of mycoplasma (Bionique Laboratories). Cells were maintained in log phase culture until fusion. They were washed in PBS, counted, and viability determined (>95%) via trypan blue dye exclusion prior to fusion.

Human TNFα was produced by a recombinant cell line, named C237A, generated in Molecular Biology at Centocor. The cell line was expanded in IMDM medium (JRH Biosciences) supplemented with 5% (v/v) FBS (Cell Culture Labs), 2 mM L-glutamine (all from JRH Biosciences), and 0.5:g/mL mycophenolic acid, and cryopreserved in 95% FBS and 5% DMSO (Sigma), then stored in a vapor phase liquid nitrogen freezer in CBS (13). The cell bank was sterile (Quality Control Centocor, Malvern) and free of mycoplasma (Bionique Laboratories).

Cell Fusion.

The cell fusion was carried out using a 1:1 ratio of 653 murine myeloma cells and viable murine spleen cells. Briefly, spleen cells and myeloma cells were pelleted together. The pellet was slowly resuspended over a 30 second period in 1 mL of 50% (w/v) PEG/PBS solution (PEG molecular weight of 1,450 g/mole, Sigma) at 37° C. The fusion was stopped by slowly adding 10.5 mL of RPMI media (no additives) (JRH) (37° C.) over 1 minute. The fused cells were centrifuged for 5 minutes at 750 rpm. The cells were then resuspended in HAT medium (RPMI/HEPES medium containing 10% Fetal Bovine Serum (JRH), 1 mM sodium pyruvate, 2 mM L-glutamine, 10 μg/mL gentamicin, 2.5% Origen culturing supplement (Fisher), 50 μM 2-mercaptoethanol, 1% 653-conditioned RPMI media, 100 μM hypoxanthine, 0.4 μM aminopterin, and 16 μM thymidine) and then plated at 200 μL/well in five 96-well flat bottom tissue culture plates. The plates were then placed in a humidified 37° C. incubator containing 5% $CO_2$ and 95% air for 7-10 days.

Detection of Human IgG Anti-TNFα Antibodies in Mouse Serum. Solid phase EIAs were used to screen mouse sera for human IgG antibodies specific for human TNFα. Briefly, plates were coated with TNFα at 1 μg/mL in PBS overnight. After washing in 0.15 M saline containing 0.02% (v/v) Tween 20, the wells were blocked with 1% (w/v) BSA in PBS, 200 μL/well for 1 hour at RT. Plates were either used immediately or frozen at −20° C. for future use. Mouse sera were incubated in two-fold serial dilutions on the human TNFα-coated plates at 50 μL/well at RT for 1 hour. The plates were washed and then probed with 50 μL/well HRP-labeled goat anti-human IgG, Fc specific (Accurate) diluted 1:30,000 in 1% BSA-PBS for 1 hour at RT. The plates were again washed and 100 μL/well of the citrate-phosphate substrate solution (0.1 M citric acid and 0.2 M sodium phosphate, 0.01% $H_2O_2$ and 1 mg/mL OPD) was added for 15 minutes at RT. Stop solution (4N sulfuric acid) was then added at 25 μL/well and the OD's were read at 490 nm using an automated plate spectrophotometer.

Detection of Totally Human Immunoglobulins in Hybridoma Supernatants.

Because the GenPharm mouse is capable of generating both mouse and human immunoglobulin chains, two separate EIA assays were used to test growth-positive hybridoma clones for the presence of both human light chains and human heavy chains. Plates were coated as described above and undiluted hybridoma supernatants were incubated on the plates for one hour at 37° C. The plates were washed and probed with either HRP-conjugated goat anti-human kappa (Southern Biotech) antibody diluted 1:10,000 in 1% BSA-HBSS or HRP-conjugated goat anti-human IgG Fc specific antibody diluted to 1:30,000 in 1% BSA-HBSS for one hour at 37° C. The plates were then incubated with substrate solution as described above. Hybridoma clones that did not give a positive signal in both the anti-human kappa and anti-human IgG Fc EIA formats were discarded.

Isotyping.

Isotype determination of the antibodies was accomplished using an EIA in a format similar to that used to screen the mouse immune sera for specific titers. EIA plates were coated with goat anti-human IgG (H+L) at 10:g/mL in sodium carbonate buffer overnight at 4EC and blocked as described above. Neat supernatants from 24 well cultures were incubated on the plate for one hour at RT. The plate was washed and probed with HRP-labeled goat anti-human $IgG_1$, $IgG_2$, $IgG_3$ or $IgG_4$ (Binding Site) diluted at 1:4000 in 1% BSA-PBS for one hour at RT. The plate was again washed and incubated with substrate solution as described above.

Results and Discussion.

Generation of Totally Human Anti-Human TNFα Monoclonal Antibodies. One fusion, named GenTNV, was performed from a GenPharm mouse immunized with recombinant human TNFα protein. From this fusion, 196 growth-positive hybrids were screened. Eight hybridoma cell lines were identified that secreted totally human IgG antibodies reactive with human TNFα. These eight cell lines each secreted immunoglobulins of the human IgG1κ isotype and all were subcloned twice by limiting dilution to obtain stable cell lines (>90% homogeneous). Cell line names and respective C code designations are listed in Table 1. Each of the cell lines was frozen in 12-vial research cell banks stored in liquid nitrogen.

Parental cells collected from wells of a 24-well culture dish for each of the eight cell lines were handed over to Molecular Biology group on 2-18-99 for transfection and further characterization.

TABLE 1

GenTNV Cell Line Designations

| Name | C Code Designation |
| --- | --- |
| GenTNV14.17.12 | C414A |
| GenTNV15.28.11 | C415A |
| GenTNV32.2.16 | C416A |
| GenTNV86.14.34 | C417A |
| GenTNV118.3.36 | C418A |
| GenTNV122.23.2 | C419A |
| GenTNV148.26.12 | C420A |
| GenTNV196.9.1 | C421A |

Conclusion

The GenTNV fusion was performed utilizing splenocytes from a hybrid mouse containing human variable and constant region antibody transgenes that was immunized with recombinant human TNFα prepared at Centocor. Eight totally human, TNFα-reactive IgG monoclonal antibodies of the IgG1κ isotype were generated. Parental cell lines were transferred to Molecular Biology group for further characterization and development. One of these new human antibodies may prove useful in anti-inflammatory with the potential benefit of decreased immunogenicity and allergic-type complications as compared with Remicade.

REFERENCES

Taylor, et al., International Immunology 6:579-591 (1993).
Lonberg, et al., Nature 368:856-859 (1994).
Neuberger, M. Nature Biotechnology 14:826 (1996).
Fishwild, et al., Nature Biotechnology 14:845-851 (1996).
Scallon, et al., Cytokine 7:759-770 (1995).

Example 4: Cloning and Preparation of Cell Lines Expressing Human Anti-TNFα Antibody Summary A panel of eight human monoclonal antibodies (mAbs) with a TNV designation were found to bind immobilized human TNFα with apparently high avidity. Seven of the eight mAbs were shown to efficiently block huTNFα binding to a recombinant TNF receptor. Sequence analysis of the DNA encoding the seven mAbs confirmed that all the mAbs had human V regions. The DNA sequences also revealed that three pairs of the mAbs were identical to each other, such that the original panel of eight mAbs contained only four distinct mAbs, represented by TNV14, TNV15, TNV148, and TNV196. Based on analyses of the deduced amino acid sequences of the mAbs and results of in vitro TNFα neutralization data, mAb TNV148 and TNV14 were selected for further study.

Because the proline residue at position 75 (framework 3) in the TNV148 heavy chain was not found at that position in other human antibodies of the same subgroup during a database search, site-directed DNA mutagenesis was performed to encode a serine residue at that position in order to have it conform to known germline framework e sequences. The serine modified mAb was designated TNV148B. PCR-amplified DNA encoding the heavy and light chain variable regions of TNV148B and TNV14 was cloned into newly prepared expression vectors that were based on the recently cloned heavy and light chain genes of another human mAb (12B75), disclosed in U.S. patent application No. 60/236,827, filed Oct. 7, 2000, entitled IL-12 Antibodies, Compositions, Methods and Uses, published as WO 02/12500 which is entirely incorporated herein by reference.

P3X63Ag8.653 (653) cells or Sp2/0-Ag14 (Sp2/0) mouse myeloma cells were transfected with the respective heavy and light chain expression plasmids and screened through two rounds of subcloning for cell lines producing high levels of recombinant TNV148B and TNV14 (rTNV148B and rTNV14) mAbs. Evaluations of growth curves and stability of mAb production over time indicated that 653-transfectant clones C466D and C466C stably produced approximately 125:g/ml of rTNV148B mAb in spent cultures whereas Sp2/0 transfectant 1.73-12-122 (C467A) stably produced approximately 25:g/ml of rTNV148B mAb in spent cultures. Similar analyses indicated that Sp2/0-transfectant clone C476A produced 18:g/ml of rTNV14 in spent cultures.

Introduction

A panel of eight mAbs derived from human TNFα-immunized GenPharm/Medarex mice (HCo12/KCo5 genotype) were previously shown to bind human TNFα and to have a totally human IgG1, kappa isotype. A simple binding assay was used to determine whether the exemplary mAbs of the invention were likely to have TNFα-neutralizing activity by evaluating their ability to block TNFα from binding to recombinant TNF receptor. Based on those results, DNA sequence results, and in vitro characterizations of several of the mAbs, TNV148 was selected as the mAb to be further characterized.

DNA sequences encoding the TNV148 mAb were cloned, modified to fit into gene expression vectors that encode suitable constant regions, introduced into the well-characterized 653 and Sp2/0 mouse myeloma cells, and resulting transfected cell lines screened until subclones were identified that produced 40-fold more mAb than the original hybridoma cell line.

Materials and Methods.

Reagents and Cells.

TRIZOL reagent was purchased from Gibco BRL. Proteinase K was obtained from Sigma Chemical Company. Reverse Transcriptase was obtained from Life Sciences, Inc. Taq DNA Polymerase was obtained from either Perkin Elmer Cetus or Gibco BRL. Restriction enzymes were purchased from New England Biolabs. QIAquick PCR Purification Kit was from Qiagen. A QuikChange Site-Directed Mutagenesis Kit was purchased from Stratagene. Wizard plasmid miniprep kits and RNasin were from Promega. Optiplates were obtained from Packard. $^{125}$Iodine was purchased from Amersham. Custom oligonucleotides were purchased from Keystone/Biosource International. The names, identification numbers, and sequences of the oligonucleotides used in this work are shown in Table 2.

TABLE 2

Oligonucleotides used to clone, engineer, or sequence the TNV mAb genes.

| Name | I.D. | Sequence |
|---|---|---|
| HG1-4b | 119 | 3'-TTGGTCCAGTCGGACTGG-5' (SEQ ID NO: 10) |
| HG1-5b | 354 | 3'-CACCTGCACTCGGTGCTT-5' (SEQ ID NO: 11) |
| HG1hg | 360 | 3'-CACTGTTTTGAGTGTGTACGGGCTTAAGTT-5' (SEQ ID NO: 12) |
| HG1-6 | 35 | 3'-GCCGCACGTGTGGAAGGG-5' (SEQ ID NO: 13) |
| HCK1-3E | 117 | 3'-AGTCAAGGTCGGACTGGCTTAAGTT-5' (SEQ ID NO: 14) |
| HuK-3'Hd | 208 | 3'-GTTGTCCCCTCTCACAATCTTCGAATTT-5' (SEQ ID NO: 15) |
| HVKRNAseq | 34 | 3'-GGCGGTAGACTACTCGTC-5' (SEQ ID NO: 16) |
| BsiWI | | M D W T W S I (SEQ ID NO: 17) |
| 5'14s | 366 | 5-TTT<u>CGTACG</u>CCACCATGGACTGGACCTGGAGCATC-3' (SEQ ID NO: 18) |
| 5'46s | 367 | 5'-TTTCGTACGCCACCATGGGGTTTGGGCTGAGCTG-3' (SEQ ID NO: 19) |
| 5'47s | 368 | 5'-TTTCGTACGCCACCATGGAGTTTGGGCTGAGCATG-3' (SEQ ID NO: 20) |
| 5'63s | 369 | 5'-TTTCGTACGCCACCATGAAACACCTGTGGTTCTTC-3' (SEQ ID NO: 21) |
| 5'73s | 370 | 5'-TTTCGTACGCCACCATGGGGTCAACCGCCATCCTC-3' (SEQ ID NO: 22) |
| T V T V S S | | BstBI (SEQ ID NO: 23) |
| HuH-J6 | 388 | 3'GTGCCAGTGGCAGAGGAGTCCATTC<u>AAGCTT</u>AAGTT-5' (SEQ ID NO: 24) |
| SalI M D M R V | | (SEQ ID NO: 25) |
| LK7s | 362 | 5'-TTT<u>GTCGAC</u>ACCATGGACATGAGGGTCC(TC)C-3' (SEQ ID NO: 26) |
| LVgs | 363 | 5'-TTTGTCGACACCATGGAAGCCCCAGCTC-3' (SEQ ID NO: 27) |
| T K V D I K | | (SEQ ID NO: 28)  Afl2 |
| HuL-J3 | 380 | 3'CTGGTTTCACCTATAGTTTG/CATTCA<u>GAATTC</u>GGCGCCTTT (SEQ ID NO: 29) |
| V148-QC1 | 399 | 5'-CATCTCCAGAGACAATtCCAAGAACACGCTGTATC-3' (SEQ ID NO: 30) |
| V148-QC2 | 400 | 3'-GTAGAGGTCTCTGTTAaGGTTCTTGTGCGACATAG-5' (SEQ ID NO: 31) |

The amino acids encoded by oligonucleotide 5'14s and HuH-J6 are shown above the sequence. The 'M' amino acid residue represents the translation start codon. The underlined sequences in oligonucleotides 5'14s and HuH-J6 mark the BsiWI and BstBI restriction sites, respectively. The slash in HuH-J6 corresponds to the exon/intron boundary. Note that oligonucleotides whose sequence corresponds to the minus strand are written in a 3'-5' orientation.

A single frozen vial of 653 mouse myeloma cells was obtained. The vial was thawed that day and expanded in T flasks in IMDM, 5% FBS, 2 mM glutamine (media). These cells were maintained in continuous culture until they were transfected 2 to 3 weeks later with the anti-TNF DNA described here. Some of the cultures were harvested 5 days after the thaw date, pelleted by centrifugation, and resuspended in 95% FBS, 5% DMSO, aliquoted into 30 vials, frozen, and stored for future use. Similarly, a single frozen vial of Sp2/0 mouse myeloma cells was obtained. The vial was thawed, a new freeze-down prepared as described above, and the frozen vials stored in CBC freezer boxes AA and AB. These cells were thawed and used for all Sp2/0 transfections described here.

Assay for Inhibition of TNF Binding to Receptor.

Hybridoma cell supernatants containing the TNV mAbs were used to assay for the ability of the mAbs to block binding of $^{125}$I-labeled TNFα to the recombinant TNF receptor fusion protein, p55-sf2 (Scallon et al. (1995) *Cytokine* 7:759-770). 50:1 of p55-sf2 at 0.5:g/ml in PBS was added to Optiplates to coat the wells during a one-hour incubation at 37° C. Serial dilutions of the eight TNV cell supernatants were prepared in 96-well round-bottom plates using PBS/0.1% BSA as diluent. Cell supernatant containing anti-IL-18 mAb was included as a negative control and the same anti-IL-18 supernatant spiked with cA2 anti-TNF chimeric antibody, Remicade, U.S. Pat. No. 5,770,198, entirely incorporated herein by reference) was included as a positive control. $^{125}$I-labeled TNFα (58:Ci/:g, D. Shealy) was added to 100:1 of cell supernatants to have a final TNFα concentration of 5 ng/ml. The mixture was preincubated for one hour at RT. The coated Optiplates were washed to remove unbound p55-sf2 and 50:1 of the $^{125}$I-TNFα/cell supernatant mixture was transferred to the Optiplates. After 2 hrs at RT, Optiplates were washed three times with PBS-Tween. 100:1 of Microscint-20 was added and the cpm bound determined using the TopCount gamma counter.

Amplification of V Genes and DNA Sequence Analysis.

Hybridoma cells were washed once in PBS before addition of TRIZOL reagent for RNA preparation. Between $7\times10^6$ and $1.7\times10^7$ cells were resuspended in 1 ml TRIZOL. Tubes were shaken vigorously after addition of 200 µl of chloroform. Samples were centrifuged at 4° C. for 10 minutes. The aqueous phase was transferred to a fresh microfuge tube and an equal volume of isopropanol was added. Tubes were shaken vigorously and allowed to incubate at room temperature for 10 minutes. Samples were then centrifuged at 4° C. for 10 minutes. The pellets were washed once with 1 ml of 70% ethanol and dried briefly in a vacuum dryer. The RNA pellets were resuspended with 40 µl of DEPC-treated water. The quality of the RNA preparations was determined by fractionating 0.5 µl in a 1% agarose gel. The RNA was stored in a –80° C. freezer until used.

To prepare heavy and light chain cDNAs, mixtures were prepared that included 3 µl of RNA and 1 µg of either oligonucleotide 119 (heavy chain) or oligonucleotide 117 (light chain) (see Table 1) in a volume of 11.5 µl. The mixture was incubated at 70° C. for 10 minutes in a water bath and then chilled on ice for 10 minutes. A separate mixture was prepared that was made up of 2.5 µl of 10× reverse transcriptase buffer, 10 µl of 2.5 mM dNTPs, 1 µl of reverse transcriptase (20 units), and 0.4 µl of ribonuclease inhibitor RNasin (1 unit). 13.5 µl of this mixture was added to the 11.5 µl of the chilled RNA/oligonucleotide mixture and the reaction incubated for 40 minutes at 42° C. The cDNA synthesis reaction was then stored in a –20° C. freezer until used.

The unpurified heavy and light chain cDNAs were used as templates to PCR-amplify the variable region coding sequences. Five oligonucleotide pairs (366/354, 367/354, 368/354, 369/354, and 370/354, Table 1) were simultaneously tested for their ability to prime amplification of the heavy chain DNA. Two oligonucleotide pairs (362/208 and 363/208) were simultaneously tested for their ability to prime amplification of the light chain DNA. PCR reactions were carried out using 2 units of PLATINUM™ high fidelity (HIFI) Taq DNA polymerase in a total volume of 50 µl. Each reaction included 2 µl of a cDNA reaction, 10 pmoles of each oligonucleotide, 0.2 mM dNTPs, 5 µl of 10×HIFI Buffer, and 2 mM magnesium sulfate. The thermal cycler program was 95° C. for 5 minutes followed by 30 cycles of (94° C. for 30 seconds, 62° C. for 30 seconds, 68° C. for 1.5 minutes). There was then a final incubation at 68° C. for 10 minutes.

To prepare the PCR products for direct DNA sequencing, they were purified using the QIAquick™ PCR Purification Kit according to the manufacturer's protocol. The DNA was eluted from the spin column using 50 µl of sterile water and then dried down to a volume of 10 µl using a vacuum dryer. DNA sequencing reactions were then set up with 1 µl of purified PCR product, 10 µM oligonucleotide primer, 4 µl BigDye Terminator™ ready reaction mix, and 14 µl sterile water for a total volume of 20 µl. Heavy chain PCR products made with oligonucleotide pair 367/354 were sequenced with oligonucleotide primers 159 and 360. Light chain PCR products made with oligonucleotide pair 363/208 were sequenced with oligonucleotides 34 and 163. The thermal cycler program for sequencing was 25 cycles of (96° C. for 30 seconds, 50° C. for 15 seconds, 60° C. for 4 minutes) followed by overnight at 4° C. The reaction products were fractionated through a polyacrylamide gel and detected using an ABI 377 DNA Sequencer.

Site-directed Mutagenesis to Change an Amino Acid.

A single nucleotide in the TNV148 heavy chain variable region DNA sequence was changed in order to replace Pro$^{75}$ with a Serine residue in the TNV148 mAb. Complimentary oligonucleotides, 399 and 400 (Table 1), were designed and ordered to make this change using the QuikChange™ site-directed mutagenesis method as described by the manufacturer. The two oligonucleotides were first fractionated through a 15% polyacrylamide gel and the major bands purified. Mutagenesis reactions were prepared using either 10 ng or 50 ng of TNV148 heavy chain plasmid template (p1753), 5 µl of 10× reaction buffer, 1 µl of dNTP mix, 125 ng of primer 399, 125 ng of primer 400, and 1 µl of Pfu DNA Polymerase. Sterile water was added to bring the total volume to 50 µl. The reaction mix was then incubated in a thermal cycler programmed to incubate at 95° C. for 30 seconds, and then cycle 14 times with sequential incubations of 95° C. for 30 seconds, 55° C. for 1 minute, 64° C. for 1 minute, and 68° C. for 7 minutes, followed by 30° C. for 2 minutes (1 cycle). These reactions were designed to incorporate the mutagenic oligonucleotides into otherwise identical, newly synthesized plasmids. To rid of the original TNV148 plasmids, samples were incubated at 37° C. for 1 hour after addition of 1 µl of DpnI endonuclease, which cleaves only the original methylated plasmid. One µl of the reaction was then used to transform Epicurian Coli XL1-Blue supercompetent *E. coli* by standard heat-shock methods and transformed bacteria identified after plating on LB-ampicillin agar plates. Plasmid minipreps were prepared using the Wizard™ kits as described by the manufacturer. After elution of sample from the Wizard™ column, plasmid DNA was precipitated with ethanol to further purify the plasmid DNA and then resuspended in 20 µl of sterile water. DNA sequence analysis was then performed to identify plasmid clones that had the desired base change and to confirm that no other base changes were inadvertently introduced into the TNV148 coding sequence. One µl of plasmid was subjected to a cycle sequencing reaction prepared with 3 µl of BigDye mix, 1 µl of pUC19 Forward primer, and 10 µl of sterile water using the same parameters described in Section 4.3.

Construction of Expression Vectors from 12B75 Genes.

Several recombinant DNA steps were performed to prepare a new human IgG1 expression vector and a new human kappa expression vector from the previously-cloned genomic copies of the 12B75-encoding heavy and light chain genes, respectively, disclosed in U.S. patent application No. 60/236,827, filed Oct. 7, 2000, entitled IL-12 Antibodies, Compositions, Methods and Uses, published as WO 02/12500 which is entirely incorporated herein by reference. The final vectors were designed to permit simple, one-step replacement of the existing variable region sequences with any appropriately-designed, PCR-amplified, variable region.

To modify the 12B75 heavy chain gene in plasmid p1560, a 6.85 kb BamHI/HindIII fragment containing the promoter and variable region was transferred from p1560 to pUC19 to make p1743. The smaller size of this plasmid compared to p1560 enabled use of QuikChange™ mutagenesis (using oligonucleotides BsiWI-1 and BsiWI-2) to introduce a unique BsiWI cloning site just upstream of the translation initiation site, following the manufacturer's protocol. The resulting plasmid was termed p1747. To introduce a BstBI site at the 3' end of the variable region, a 5' oligonucleotide primer was designed with SalI and BstBI sites. This primer was used with the pUC reverse primer to amplify a 2.75 kb fragment from p1747. This fragment was then cloned back into the naturally-occurring SalI site in the 12B75 variable region and a HindIII site, thereby introducing the unique BstB1 site. The resulting intermediate vector, designated p1750, could accept variable region fragments with BsiWI and BstBI ends. To prepare a version of heavy chain vector in which the constant region also derived from the 12B75 gene, the BamHI-HindIII insert in p1750 was transferred to pBR322 in order to have an EcoRI site downstream of the HindIII site. The resulting plasmid, p1768, was then digested with HindIII and EcoRI and ligated to a 5.7 kb HindIII-EcoRI fragment from p1744, a subclone derived by cloning the large BamHI-BamHI fragment from p1560 into pBC. The resulting plasmid, p1784, was then used as vector for the TNV Ab cDNA fragments with BsiWI and BstBI ends. Additional work was done to prepare expression vectors, p1788 and p1798, which include the IgG1 constant region from the 12B75 gene and differ from each other by how much of the 12B75 heavy chain J-C intron they contain.

To modify the 12B75 light chain gene in plasmid p1558, a 5.7 kb SalI/AflIII fragment containing the 12B75 promoter and variable region was transferred from p1558 into the XhoI/AflIII sites of plasmid L28. This new plasmid, p1745, provided a smaller template for the mutagenesis step. Oligonucleotides (C340salI and C340sal2) were used to introduce a unique SalI restriction site at the 5' end of the variable region by QuikChange™ mutagenesis. The resulting intermediate vector, p1746, had unique SalI and AflIII restriction sites into which variable region fragments could be cloned. Any variable region fragment cloned into p1746 would preferably be joined with the 3' half of the light chain gene. To prepare a restriction fragment from the 3' half of the 12B75 light chain gene that could be used for this purpose, oligonucleotides BAHN-1 and BAHN-2 were annealed to each other to form a double-stranded linker containing the restriction sites BsiW1, AflII, HindII, and NotI and which contained ends that could be ligated into KpnI and SacI sites. This linker was cloned between the KpnI and SacI sites of pBC to give plasmid p1757. A 7.1 kb fragment containing the 12B75 light chain constant region, generated by digesting p1558 with AflII, then partially digesting with HindIII, was cloned between the AflII and HindII sites of p1757 to yield p1762. This new plasmid contained unique sites for BsiWI and AflII into which the BsiWI/AflII fragment containing the promoter and variable regions could be transferred uniting the two halves of the gene.

cDNA Cloning and Assembly of Expression Plasmids. All RT-PCR reactions (see above) were treated with Klenow enzyme to further fill in the DNA ends. Heavy chain PCR fragments were digested with restriction enzymes BsiWI and BstBI and then cloned between the BsiWI and BstBI sites of plasmid L28 (L28 used because the 12B75-based intermediate vector p1750 had not been prepared yet). DNA sequence analysis of the cloned inserts showed that the resulting constructs were correct and that there were no errors introduced during PCR amplifications. The assigned identification numbers for these L28 plasmid constructs (for TNV14, TNV15, TNV148, TNV148B, and TNV196) are shown in Table 3.

The BsiWI/BstBI inserts for TNV14, TNV148, and TNV148B heavy chains were transferred from the L28 vector to the newly prepared intermediate vector, p1750. The assigned identification numbers for these intermediate plasmids are shown in Table 2. This cloning step and subsequent steps were not done for TNV15 and TNV196. The variable regions were then transferred into two different human IgG1 expression vectors. Restriction enzymes EcoRI and HindIII were used to transfer the variable regions into Centocor's previously-used IgG1 vector, p104. The resulting expression plasmids, which encode an IgG1 of the Gm(f+) allotype, were designated p1781 (TNV14), p1782 (TNV148), and p1783 (TNV148B) (see Table 2). The variable regions were also cloned upstream of the IgG1 constant region derived from the 12B75 (GenPharm) gene. Those expression plasmids, which encode an IgG1 of the G1m(z) allotype, are also listed in Table 3.

TABLE 3

Plasmid identification numbers for various heavy and light chain plasmids. The L28 vector or pBC vector represents the initial Ab cDNA clone. The inserts in those plasmids were transferred to an incomplete 12B75-based vector to make the intermediate plasmids. One additional transfer step resulted in the final expression plasmids that were either introduced into cells after being linearized or used to purify the mAb gene inserts prior to cell transfection. (ND) = not done.

| Gm(f+) Mab Heavy Chains | 128 vector Plasmid ID | Intermediate Plasmid ID | G1m(z) Expression Plasmid ID | Expression Plasmid ID |
|---|---|---|---|---|
| TNV14 | p1751 | p1777 | p1781 | p1786 |
| TNV15 | p1752 | (ND) | (ND) | (ND) |
| TNV148 | p1753 | p1778 | p1782 | p1787 |

TABLE 3-continued

Plasmid identification numbers for various heavy and light chain plasmids.
The L28 vector or pBC vector represents the initial Ab cDNA clone. The
inserts in those plasmids were transferred to an incomplete 12B75-based vector to make
the intermediate plasmids. One additional transfer step resulted in the final expression
plasmids that were either introduced into cells after being linearized or used to purify
the mAb gene inserts prior to cell transfection. (ND) = not done.

| Gm(f+) Mab | | Glm(z) | | |
|---|---|---|---|---|
| TNV148B | p1760 | p1779 | p1783 | p1788 |
| TNV196 | p1754 | (ND) | (ND) | (ND) |

| Light Chains | pBC vector Plasmid ID | Intermediate Plasmid ID | Expression Plasmid ID |
|---|---|---|---|
| TNV14 | p1748 | p1755 | p1775 |
| TNV15 | p1748 | p1755 | p1775 |
| TNV148 | p1749 | p1756 | p1776 |
| TNV196 | p1749 | p1756 | p1776 |

Light chain PCR products were digested with restriction enzymes SalI and SacII and then cloned between the SalI and SacII sites of plasmid pBC. The two different light chain versions, which differed by one amino acid, were designated p1748 and p1749 (Table 2). DNA sequence analysis confirmed that these constructs had the correct sequences. The SalI/AflII fragments in p1748 and p1749 were then cloned between the SalI and AflII sites of intermediate vector p1746 to make p1755 and p1756, respectively. These 5' halves of the light chain genes were then joined to the 3' halves of the gene by transferring the BsiWI/AflII fragments from p1755 and p1756 to the newly prepared construct p1762 to make the final expression plasmids p1775 and p1776, respectively (Table 2).

Cell Transfections, Screening, and Subcloning.

A total of 15 transfections of mouse myeloma cells were performed with the various TNV expression plasmids (see Table 3 in the Results and Discussion section). These transfections were distinguished by whether (1) the host cells were Sp2/0 or 653; (2) the heavy chain constant region was encoded by Centocor's previous IgG1 vector or the 12B75 heavy chain constant region; (3) the mAb was TNV148B, TNV148, TNV14, or a new HC/LC combination; (4) whether the DNA was linearized plasmid or purified Ab gene insert; and (5) the presence or absence of the complete J-C intron sequence in the heavy chain gene. In addition, several of the transfections were repeated to increase the likelihood that a large number of clones could be screened.

Sp2/0 cells and 653 cells were each transfected with a mixture of heavy and light chain DNA (8-12:g each) by electroporation under standard conditions as previously described (Knight D M et al. (1993) Molecular Immunology 30:1443-1453). For transfection numbers 1, 2, 3, and 16, the appropriate expression plasmids were linearized by digestion with a restriction enzyme prior to transfection. For example, SalI and NotI restriction enzymes were used to linearize TNV148B heavy chain plasmid p1783 and light chain plasmid p1776, respectively. For the remaining transfections, DNA inserts that contained only the mAb gene were separated from the plasmid vector by digesting heavy chain plasmids with BamHI and light chain plasmids with BsiWI and NotI. The mAb gene inserts were then purified by agarose gel electrophoresis and Qiex purification resins. Cells transfected with purified gene inserts were simultaneously transfected with 3-5:g of PstI-linearized pSV2gpt plasmid (p13) as a source of selectable marker. Following electroporation, cells were seeded in 96-well tissue culture dishes in IMDM, 15% FBS, 2 mM glutamine and incubated at 37° C. in a 5% $CO_2$ incubator. Two days later, an equal volume of IMDM, 5% FBS, 2 mM glutamine, 2×MHX selection (1×MHX=0.5:g/ml mycophenolic acid, 2.5:g/ml hypoxanthine, 50:g/ml xanthine) was added and the plates incubated for an additional 2 to 3 weeks while colonies formed.

Cell supernatants collected from wells with colonies were assayed for human IgG by ELISA as described. In brief, varying dilutions of the cell supernatants were incubated in 96-well EIA plates coated with polyclonal goat anti-human IgG Fc fragment and then bound human IgG was detected using Alkaline Phosphatase-conjugated goat anti-human IgG(H+L) and the appropriate color substrates. Standard curves, which used as standard the same purified mAb that was being measured in the cell supernatants, were included on each EIA plate to enable quantitation of the human IgG in the supernatants. Cells in those colonies that appeared to be producing the most human IgG were passaged into 24-well plates for additional production determinations in spent cultures and the highest-producing parental clones were subsequently identified.

The highest-producing parental clones were subcloned to identify higher-producing subclones and to prepare a more homogenous cell line. 96-well tissue culture plates were seeded with one cell per well or four cells per well in of IMDM, 5% FBS, 2 mM glutamine, 1×MHX and incubated at 37° C. in a 5% $CO_2$ incubator for 12 to 20 days until colonies were apparent. Cell supernatants were collected from wells that contained one colony per well and analyzed by ELISA as described above. Selected colonies were passaged to 24-well plates and the cultures allowed to go spent before identifying the highest-producing subclones by quantitating the human IgG levels in their supernatants. This process was repeated when selected first-round subclones were subjected to a second round of subcloning. The best second-round subclones were selected as the cell lines for development.

Characterization of Cell Subclones.

The best second-round subclones were chosen and growth curves performed to evaluate mAb production levels and cell growth characteristics. T75 flasks were seeded with $1×10^5$ cells/ml in 30 ml IMDM, 5% FBS, 2 mM glutamine, and 1×MHX (or serum-free media). Aliquots of 300 μl were taken at 24 hr intervals and live cell density determined. The analyses continued until the number of live cells was less than 1×10⁵ cells/ml. The collected aliquots of cell supernatants were assayed for the concentration of antibody present. ELISA assays were performed using as standard rTNV148B or rTNV14 JG92399. Samples were incubated for 1 hour on ELISA plates coated with polyclonal goat anti-human IgG Fc and bound mAb detected with Alkaline Phosphatase-conjugated goat anti-human IgG(H+L) at a 1:1000 dilution.

A different growth curve analysis was also done for two cell lines for the purpose of comparing growth rates in the presence of varying amounts of MHX selection. Cell lines C466A and C466B were thawed into MHX-free media (IMDM, 5% FBS, 2 mM glutamine) and cultured for two additional days. Both cell cultures were then divided into three cultures that contained either no MHX, 0.2×MHX, or 1× MHX (1×MHX=0.5:g/ml mycophenolic acid, 2.5:g/ml hypoxanthine, 50:g/ml xanthine). One day later, fresh T75 flasks were seeded with the cultures at a starting density of 1×10⁵ cells/ml and cells counted at 24 hour intervals for one week. Aliquots for mAb production were not collected. Doubling times were calculated for these samples using the formula provided in SOP PD32.025.

Additional studies were performed to evaluate stability of mAb production over time. Cultures were grown in 24-well plates in IMDM, 5% FBS, 2 mM glutamine, either with or without MHX selection. Cultures were split into fresh cultures whenever they became confluent and the older culture was then allowed to go spent. At this time, an aliquot of supernatant was taken and stored at 4° C. Aliquots were taken over a 55-78 day period. At the end of this period, supernatants were tested for amount of antibody present by the anti-human IgG Fc ELISA as outlined above.

Results and Discussion.
Inhibition of TNF Binding to Recombinant Receptor.

A simple binding assay was done to determine whether the eight TNV mAbs contained in hybridoma cell supernatant were capable of blocking TNFα binding to receptor. The concentrations of the TNV mAbs in their respective cell supernatants were first determined by standard ELISA analysis for human IgG. A recombinant p55 TNF receptor/IgG fusion protein, p55-sf2, was then coated on EIA plates and $^{125}$I-labeled TNFα allowed to bind to the p55 receptor in the presence of varying amounts of TNV mAbs. As shown in FIG. 1, all but one (TNV122) of the eight TNV mAbs efficiently blocked TNFα binding to p55 receptor. In fact, the TNV mAbs appeared to be more effective at inhibiting TNFα binding than cA2 positive control mAb that had been spiked into negative control hybridoma supernatant. These results were interpreted as indicating that it was highly likely that the TNV mAbs would block TNFα bioactivity in cell-based assays and in vivo and therefore additional analyses were warranted.

DNA Sequence Analysis.
Confirmation that the RNAs Encode Human mAbs.

As a first step in characterizing the seven TNV mAbs (TNV14, TNV15, TNV32, TNV86, TNV118, TNV148, and TNV196) that showed TNFα-blocking activity in the receptor binding assay, total RNA was isolated from the seven hybridoma cell lines that produce these mAbs. Each RNA sample was then used to prepare human antibody heavy or light chain cDNA that included the complete signal sequence, the complete variable region sequence, and part of the constant region sequence for each mAb. These cDNA products were then amplified in PCR reactions and the PCR-amplified DNA was directly sequenced without first cloning the fragments. The heavy chain cDNAs sequenced were >90% identical to one of the five human germline genes present in the mice, DP-46 (FIG. 2). Similarly, the light chain cDNAs sequenced were either 100% or 98% identical to one of the human germline genes present in the mice (FIG. 3). These sequence results confirmed that the RNA molecules that were transcribed into cDNA and sequenced encoded human antibody heavy chains and human antibody light chains. It should be noted that, because the variable regions were PCR-amplified using oligonucleotides that map to the 5' end of the signal sequence coding sequence, the first few amino acids of the signal sequence may not be the actual sequence of the original TNV translation products but they do represent the actual sequences of the recombinant TNV mAbs.

Unique Neutralizing mAbs.

Analyses of the cDNA sequences for the entire variable regions of both heavy and light chains for each mAb revealed that TNV32 is identical to TNV15, TNV118 is identical to TNV14, and TNV86 is identical to TNV148. The results of the receptor binding assay were consistent with the DNA sequence analyses, i.e. both TNV86 and TNV148 were approximately 4-fold better than both TNV118 and TNV14 at blocking TNF binding. Subsequent work was therefore focused on only the four unique TNV mAbs, TNV14, TNV15, TNV148, and TNV196.

Relatedness of the Four mAbs

The DNA sequence results revealed that the genes encoding the heavy chains of the four TNV mAbs were all highly homologous to each other and appear to have all derived from the same germline gene, DP-46 (FIG. 2). In addition, because each of the heavy chain CDR3 sequences are so similar and of the same length, and because they all use the J6 exon, they apparently arose from a single VDJ gene rearrangement event that was then followed by somatic changes that made each mAb unique. DNA sequence analyses revealed that there were only two distinct light chain genes among the four mAbs (FIG. 3). The light chain variable region coding sequences in TNV14 and TNV15 are identical to each other and to a representative germline sequence of the Vg/38K family of human kappa chains. The TNV148 and TNV196 light chain coding sequences are identical to each other but differ from the germline sequence at two nucleotide positions (FIG. 3).

The deduced amino acid sequences of the four mAbs revealed the relatedness of the actual mAbs. The four mAbs contain four distinct heavy chains (FIG. 4) but only two distinct light chains (FIG. 5). Differences between the TNV mAb sequences and the germline sequences were mostly confined to CDR domains but three of the mAb heavy chains also differed from the germline sequence in the framework regions (FIG. 4). Compared to the DP-46 germline-encoded Ab framework regions, TNV14 was identical, TNV15 differed by one amino acid, TNV148 differed by two amino acids, and TNV196 differed by three amino acids.

Cloning of cDNAs, Site-Specific Mutagenesis, and Assembly of Final Expression Plasmids.

Cloning of cDNAs. Based on the DNA sequence of the PCR-amplified variable regions, new oligonucleotides were ordered to perform another round of PCR amplification for the purpose of adapting the coding sequence to be cloned into expression vectors. In the case of the heavy chains, the products of this second round of PCR were digested with restriction enzymes BsiWI and BstBI and cloned into plasmid vector L28 (plasmid identification numbers shown in Table 2). In the case of the light chains, the second-round PCR products were digested with SalI and AflII and cloned into plasmid vector pBC. Individual clones were then sequenced to confirm that their sequences were identical to the previous sequence obtained from direct sequencing of PCR products, which reveals the most abundant nucleotide at each position in a potentially heterogeneous population of molecules.

Site-Specific Mutagenesis to Change TNV148.

mAbs TNV148 and TNV196 were being consistently observed to be four-fold more potent than the next best mAb (TNV14) at neutralizing TNFα bioactivity. However, as described above, the TNV148 and TNV196 heavy chain framework sequences differed from the germline framework sequences. A comparison of the TNV148 heavy chain sequence to other human antibodies indicated that numerous other human mAbs contained an Ile residue at position 28 in framework 1 (counting mature sequence only) whereas the Pro residue at position 75 in framework 3 was an unusual amino acid at that position.

A similar comparison of the TNV196 heavy chain suggested that the three amino acids by which it differs from the germline sequence in framework 3 may be rare in human mAbs. There was a possibility that these differences may render TNV148 and TNV196 immunogenic if administered to humans. Because TNV148 had only one amino acid residue of concern and this residue was believed to be unimportant for TNFα binding, a site-specific mutagenesis technique was used to change a single nucleotide in the TNV148 heavy chain coding sequence (in plasmid p1753) so that a germline Ser residue would be encoded in place of the Pro residue at position 75. The resulting plasmid was termed p1760 (see Table 2). The resulting gene and mAb were termed TNV148B to distinguish it from the original TNV148 gene and mAb (see FIG. 5).

Assembly of Final Expression Plasmids.

New antibody expression vectors were prepared that were based on the 12B75 heavy chain and light chain genes previously cloned as genomic fragments. Although different TNV expression plasmids were prepared (see Table 2), in each case the 5' flanking sequences, promoter, and intron enhancer derived from the respective 12B75 genes. For the light chain expression plasmids, the complete J-C intron, constant region coding sequence and 3' flanking sequence were also derived from the 12B75 light chain gene. For the heavy chain expression plasmids that resulted in the final production cell lines (p1781 and p1783, see below), the human IgG1 constant region coding sequences derived from Centocor's previously-used expression vector (p104). Importantly, the final production cell lines reported here express a different allotype (Gm(f+)) of the TNV mAbs than the original, hybridoma-derived TNV mAbs (G1m(z)). This is because the 12B75 heavy chain gene derived from the GenPharm mice encodes an Arg residue at the C-terminal end of the CH1 domain whereas Centocor's IgG1 expression vector p104 encodes a Lys residue at that position. Other heavy chain expression plasmids (e.g. p1786 and p1788) were prepared in which the J-C intron, complete constant region coding sequence and 3' flanking sequence were derived from the 12B75 heavy chain gene, but cell lines transfected with those genes were not selected as the production cell lines. Vectors were carefully designed to permit one-step cloning of future PCR-amplified V regions that would result in final expression plasmids.

PCR-amplified variable region cDNAs were transferred from L28 or pBC vectors to intermediate-stage, 12B75-based vectors that provided the promoter region and part of the J-C intron (see Table 2 for plasmid identification numbers). Restriction fragments that contained the 5' half of the antibody genes were then transferred from these intermediate-stage vectors to the final expression vectors that provided the 3' half of the respective genes to form the final expression plasmids (see Table 2 for plasmid identification numbers).

Cell Transfections and Subcloning.

Expression plasmids were either linearized by restriction digest or the antibody gene inserts in each plasmid were purified away from the plasmid backbones. Sp2/0 and 653 mouse myeloma cells were transfected with the heavy and light chain DNA by electroporation. Fifteen different transfections were done, most of which were unique as defined by the Ab, specific characteristics of the Ab genes, whether the genes were on linearized whole plasmids or purified gene inserts, and the host cell line (summarized in Table 5). Cell supernatants from clones resistant to mycophenolic acid were assayed for the presence of human IgG by ELISA and quantitated using purified rTNV148B as a reference standard curve.

Highest-Producing rTNV148B Cell Lines

Ten of the best-producing 653 parental lines from rTNV148B transfection 2 (produced 5-10:g/ml in spent 24-well cultures) were subcloned to screen for higher-producing cell lines and to prepare a more homogeneous cell population. Two of the subclones of the parental line 2.320, 2.320-17 and 2.320-20, produced approximately 50:g/ml in spent 24-well cultures, which was a 5-fold increase over their parental line. A second round of subcloning of subcloned lines 2.320-17 and 2.320-20 led The identification numbers of the heavy and light chain plasmids that encode each mAb are shown. In the case of transfections done with purified mAb gene inserts, plasmid p13 (pSV2gpt) was included as a source of the gpt selectable marker. The heavy chain constant regions were encoded either by the same human IgG1 expression vector used to encode Remicade ('old') or by the constant regions contained within the 12B75 (GenPharm/Medarex) heavy chain gene ('new'). H1/L2 refers to a "novel" mAb made up of the TNV14 heavy chain and the TNV148 light chain. Plasmids p1783 and p1801 differ only by how much of the J-C intron their heavy chain genes contain. The transfection numbers, which define the first number of the generic names for cell clones, are shown on the right. The rTNV148B-producing cell lines C466 (A, B, C, D) and C467A described here derived from transfection number 2 and 1, respectively. The rTNV14-producing cell line C476A derived from transfection number 3.

TABLE 5

Summary of Cell Transfections.

| Plasmids | HC | DNA | | Transfection no. | |
|---|---|---|---|---|---|
| mAb | HC/LC/2pt | vector | format | Sp2/0 | 653 |
| rTNV148B | 1783/1776 | old | linear | 1 | 2 |
| rTNV14 | 1781/1775 | old | linear | 3 | — |
| rTNV148B | 1788/1776/13 | new | insert | 4, 6 | 5, 7 |
| rTNV14 | 1786/1775/13 | new | insert | 8, 10 | 9, 11 |
| rTNV148 | 1787/1776/13 | new | insert | 12 | 17 |
| rH1/L2 | 1786/1776/13 | new | insert | 13 | 14 |
| rTNV148B | 1801/1776 | old | linear | 16 | |

ELISA assays on spent 24-well culture supernatants indicated that these second-round subclones all produced between 98 and 124:g/ml, which was at least a 2-fold increase over the first-round subclones. These 653 cell lines were assigned C code designations as shown in Table 6.

Three of the best-producing Sp2/0 parental lines from rTNV148B transfection 1 were subcloned. Two rounds of subcloning of parental line 1.73 led to the identification of a clone that produced 25:g/ml in spent 24-well cultures. This Sp2/0 cell line was designated C467A (Table 6).

Highest-Producing rTNV14 Cell Lines

Three of the best-producing Sp2/0 parental lines from rTNV14 transfection 3 were subcloned once. Subclone 3.27-1 was found to be the highest-producer in spent 24-well cultures with a production of 19:g/ml. This cell line was designated C476A (Table 6).

TABLE 6

Summary of Selected Production Cell Lines and their C codes. The first digit of the original clone names indicates which transfection the cell line derived from. All of the C-coded cell lines reported here were derived from transfections with heavy and light chain whole plasmids that had been linearized with restriction enzymes.

| Original mAb | Clone Name | Spent 24-well C code | Host Cell | Production |
|---|---|---|---|---|
| rTNV148B | 2.320-17-36 | C466A | 653 | 103:g/ml |
|  | 2.320-20-111 | C466B | 653 | 102:g/ml |
|  | 2.320-17-4 | C466C | 653 | 98:g/ml |
|  | 2.320-20-99 | C466D | 653 | 124:g/ml |
|  | 1.73-12-122 | C467A | Sp2/0 | 25:g/ml |
| rTNV14 | 3.27-1 | C476A | Sp2/0 | 19:g/ml |

Characterization of Subcloned Cell Lines

Figure 7:
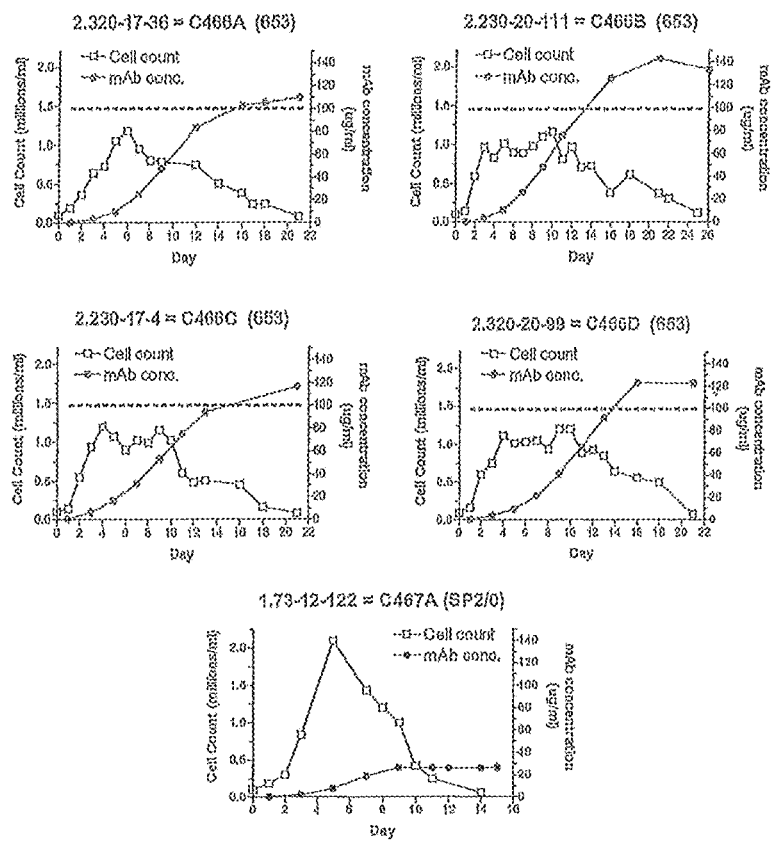

To more carefully characterize cell line growth characteristics and determine mAb-production levels on a larger scale, growth curves analyses were performed using T75 cultures. The results showed that each of the four C466 series of cell lines reached peak cell density between $1.0 \times 10^6$ and $1.25 \times 10^6$ cells/ml and maximal mAb accumulation levels of between 110 and 140:g/ml (FIG. 7). In contrast, the best-producing Sp2/0 subclone, C467A, reached peak cell density of $2.0 \times 10^6$ cells/ml and maximal mAb accumulation levels of 25:g/ml (FIG. 7). A growth curve analysis was not done on the rTNV14-producing cell line, C476A.

Figure 8:
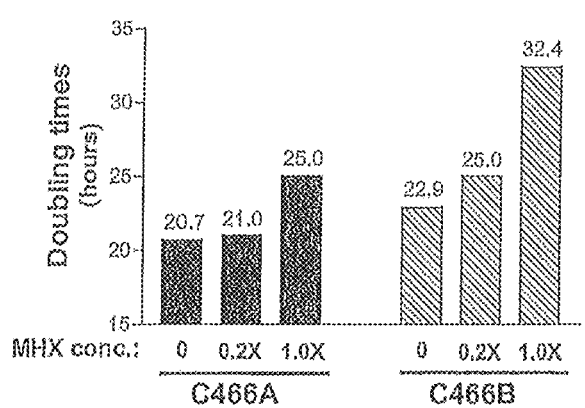

An additional growth curve analysis was done to compare the growth rates in different concentrations of MHX selection. This comparison was prompted by recent observations that C466 cells cultured in the absence of MHX seemed to be growing faster than the same cells cultured in the normal amount of MHX (1x). Because the cytotoxic concentrations of compounds such as mycophenolic acid tend to be measured over orders of magnitude, it was considered possible that the use of a lower concentration of MHX might result in significantly faster cell doubling times without sacrificing stability of mAb production. Cell lines C466A and C466B were cultured either in: no MHX, 0.2xMHX, or 1xMHX. Live cell counts were taken at 24-hour intervals for 7 days. The results did reveal an MHX concentration-dependent rate of cell growth (FIG. 8). Cell line C466A showed a doubling time of 25.0 hours in 1xMHX but only 20.7 hours in no MHX. Similarly, cell line C466B showed a doubling time of 32.4 hours in 1xMHX but only 22.9 hours in no MHX. Importantly, the doubling times for both cell lines in 0.2x MHX were more similar to what was observed in no MHX than in 1xMHX (FIG. 8). This observation raises the possibility than enhanced cell performance in bioreactors, for which doubling times are an important parameter, could be realized by using less MHX. However, although stability test results (see below) suggest that cell line C466D is capable of stably producing rTNV148B for at least 60 days even with no MHX present, the stability test also showed higher mAb production levels when the cells were cultured in the presence of MHX compared to the absence of MHX.

Figure 9:
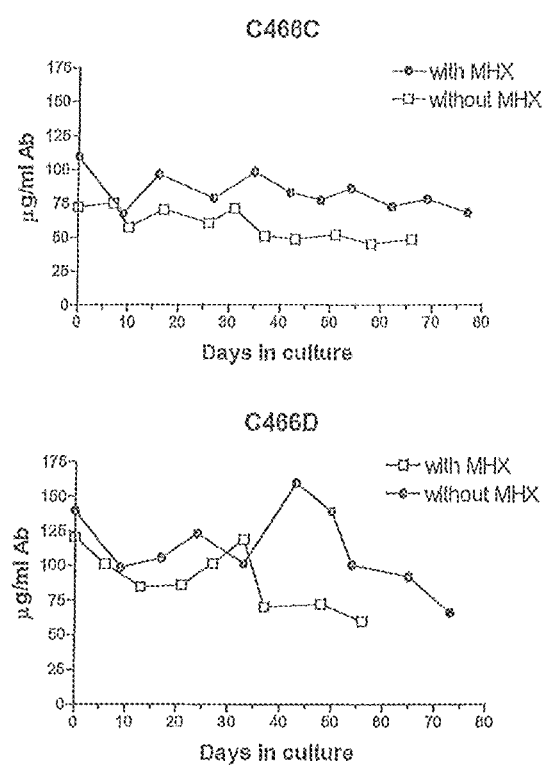

To evaluate mAb production from the various cell lines over a period of approximately 60 days, stability tests were performed on cultures that either contained, or did not contain, MHX selection. Not all of the cell lines maintained high mAb production. After just two weeks of culture, clone C466A was producing approximately 45% less than at the beginning of the study. Production from clone C466B also appeared to drop significantly. However, clones C466C and C466D maintained fairly stable production, with C466D showing the highest absolute production levels (FIG. 9).

Conclusion

From an initial panel of eight human mAbs against human TNFα, TNV148B was selected as preferred based on several criteria that included protein sequence and TNF neutralization potency, as well as TNV14. Cell lines were prepared that produce greater than 100:g/ml of rTNV148B and 19:g/ml rTNV14.

Example 5: Arthritic Mice Study Using Anti-TNF Antibodies and Controls Using Single Bolus Injection At approximately 4 weeks of age the Tg197 study mice were assigned, based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg.

Figure 10:
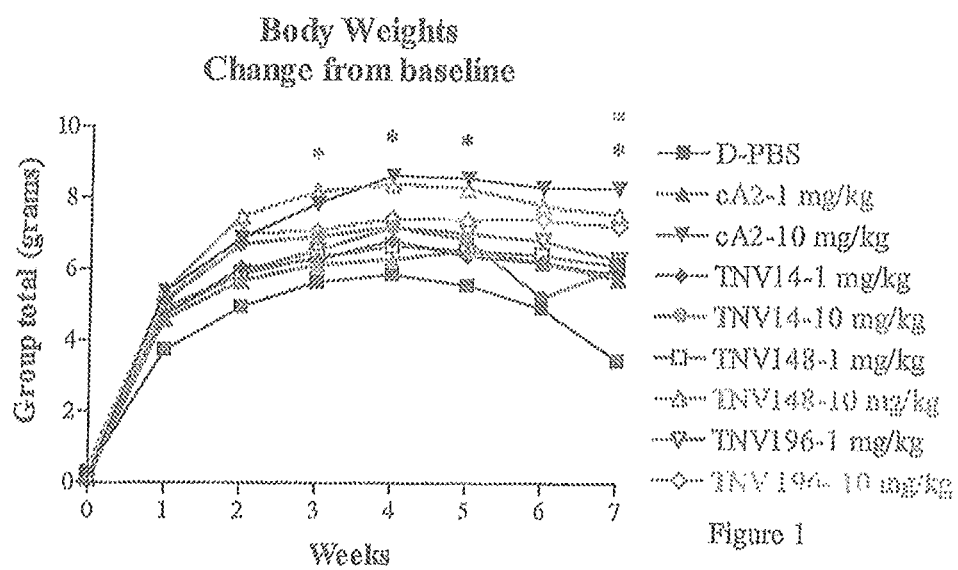

Results:

When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study. (See FIG. 10).

Figure 11A:
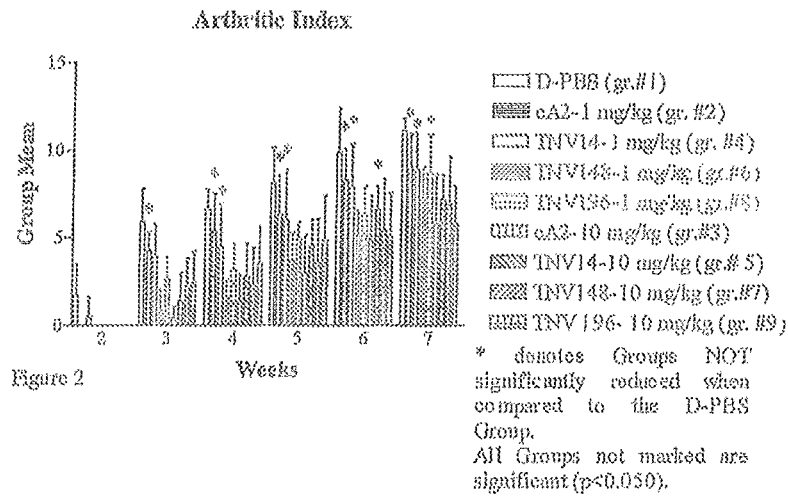
FIGS. 11A-C represent the progression of disease severity based on the arthritic index as presented in Example 4. The 10 mg/kg cA2-treated group's arthritic index was lower then the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.
Figure 11B:
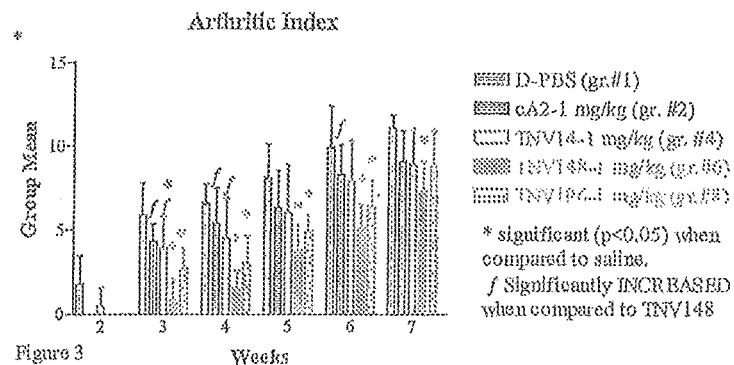
Figure 11C:
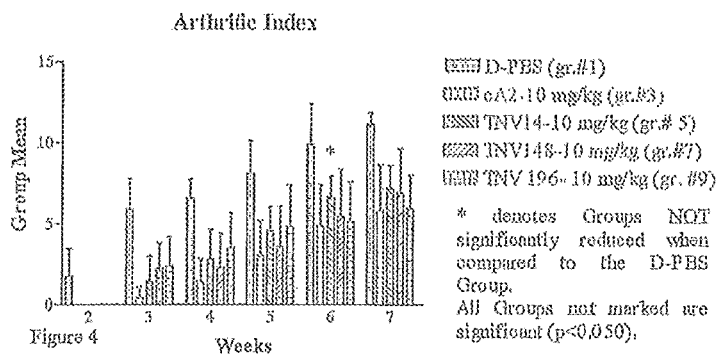

FIGS. 11A-C represent the progression of disease severity based on the arthritic index. The 10 mg/kg cA2-treated group's arthritic index was lower then the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.

Example 6: Arthritic Mice Study Using Anti-TNF Antibodies and Controls as Multiple Bolus Doses At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV148 at weeks 2, 3 and 4.

Figure 12:
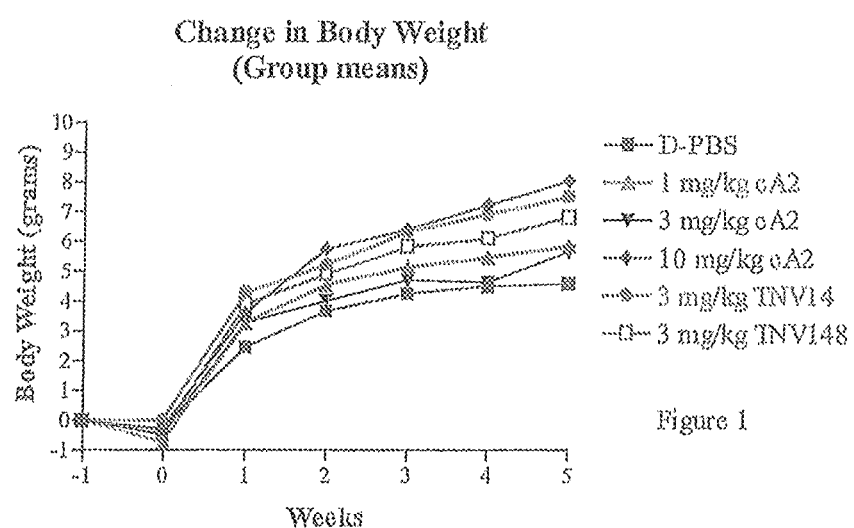
FIG. 12 shows arthritis mouse model mice Tg 197 weight changes in response to anti-TNF antibodies of the present invention as compared to controls in Example 5. At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV148 at weeks 2, 3 and 4.

Results:

No significant differences were noted when the weights were analyzed as a change from pre-dose. The animals treated with 10 mg/kg cA2 showed consistently higher weight gain than the D-PBS-treated animals throughout the study. (See FIG. 12).

Figure 13A:
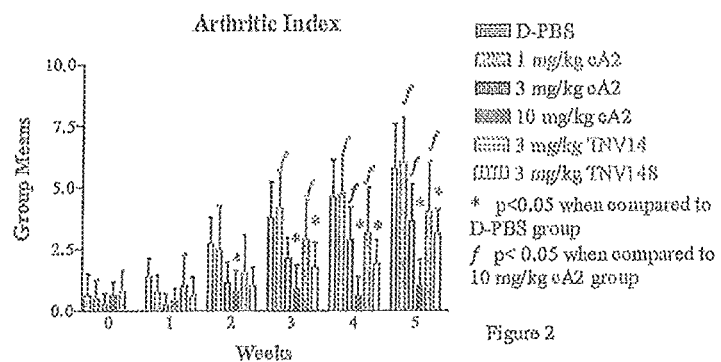
FIGS. 13A-C are graphs representing the progression of disease severity in Example 5 based on the arthritic index. The 10 mg/kg cA2-treated group's arthritic index was significantly lower then the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.
Figure 13B:
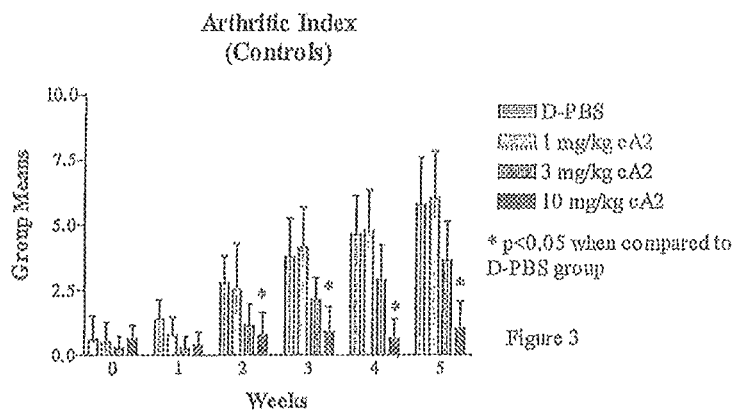
Figure 13C:
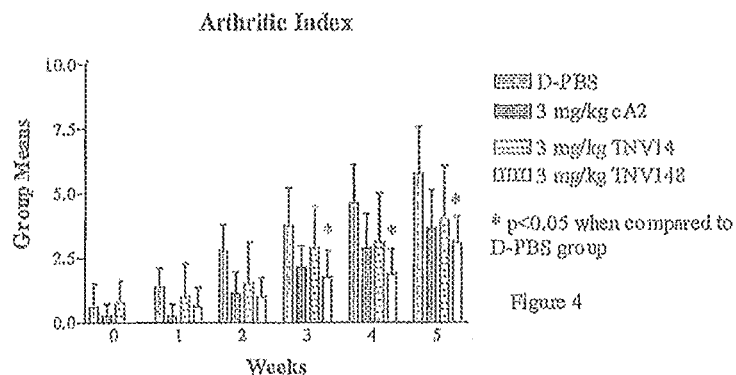

FIGS. 13A-C represent the progression of disease severity based on the arthritic index. The 10 mg/kg cA2-treated group's arthritic index was significantly lower then the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.

Example 7: Arthritic Mice Study Using Anti-TNF Antibodies and Controls as Single Intraperitoneal Bolus Dose At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

Figure 14:
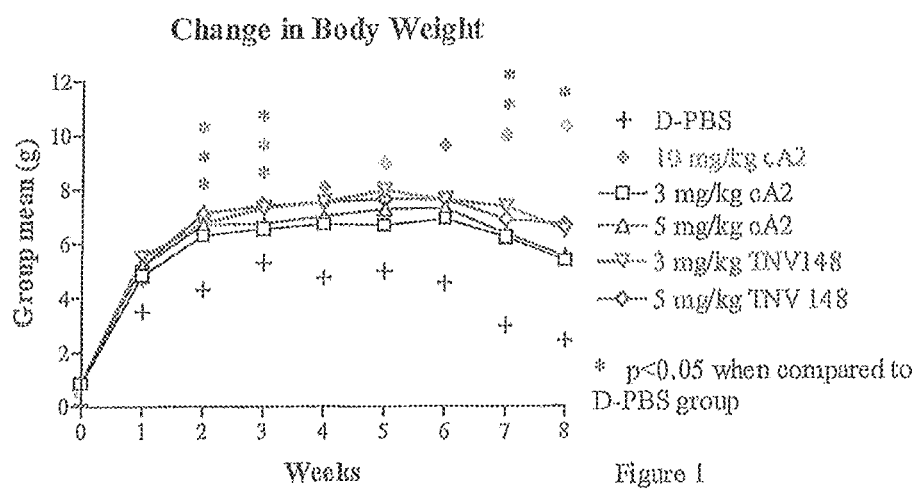
FIG. 14 shows arthritis mouse model mice Tg 197 weight changes in response to anti-TNF antibodies of the present invention as compared to controls in Example 6. At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

When the weights were analyzed as a change from pre-dose, all treatments achieved similar weight gains. The animals treated with either 3 or 5 mg/kg TNV148 or 5 mg/kg cA2 gained a significant amount of weight early in the study (at weeks 2 and 3). Only the animals treated with TNV148 maintained significant weight gain in the later time points. Both the 3 and 5 mg/kg TNV148-treated animals showed significance at 7 weeks and the 3 mg/kg TNV148 animals were still significantly elevated at 8 weeks post injection. (See FIG. 14).

Figure 15:
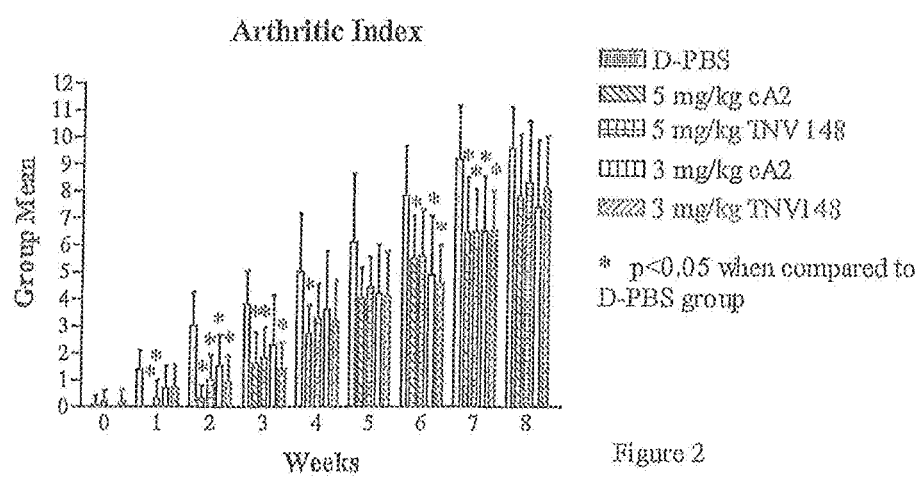
FIG. 15 represents the progression of disease severity based on the arthritic index as presented in Example 6. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

FIG. 15 represents the progression of disease severity based on the arthritic index. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

Example 8: Arthritic Mice Study Using Anti-TNF Antibodies and Controls as Single Intraperitoneal Bolus Dose Between Anti-TNF Antibody and Modified Anti-TNF Antibody To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco=S PBS (D-PBS) or antibody (TNV148, rTNV148B) at 1 mg/kg.

Figure 16:
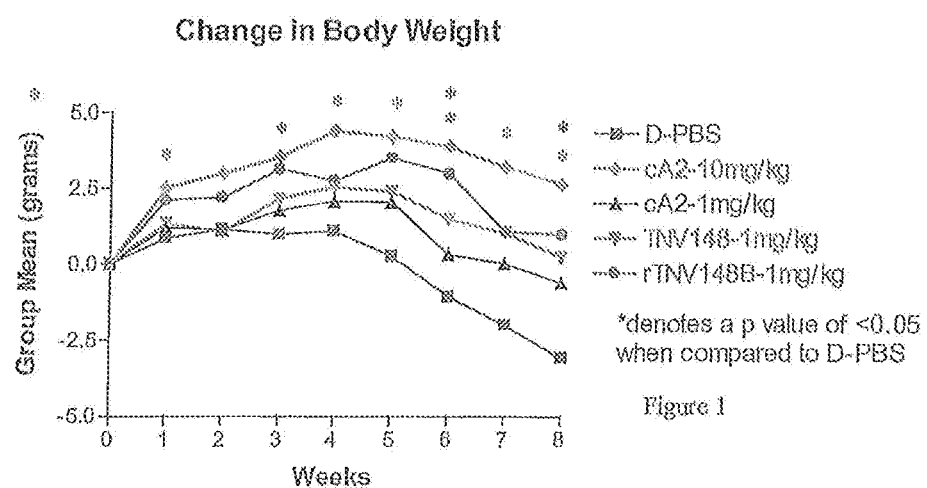
FIG. 16 shows arthritis mouse model mice Tg 197 weight changes in response to anti-TNF antibodies of the present invention as compared to controls in Example 7. To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco's PBS (D-PBS) or antibody (TNV148, rTNV148B) at 1 mg/kg.

When the weights were analyzed as a change from pre-dose, the animals treated with 10 mg/kg cA2 showed a consistently higher weight gain than the D-PBS-treated animals throughout the study. This weight gain was significant at weeks 1 and weeks 3-8. The animals treated with 1 mg/kg TNV148 also achieved significant weight gain at weeks 5, 6 and 8 of the study. (See FIG. 16).

Figure 17:
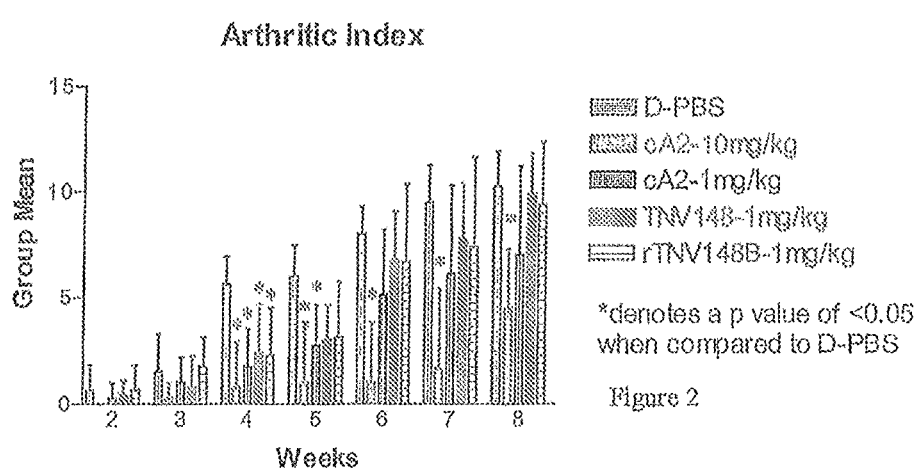
FIG. 17 represents the progression of disease severity based on the arthritic index as presented in Example 7. The 10 mg/kg cA2-treated group's arthritic index was lower then the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

FIG. 17 represents the progression of disease severity based on the arthritic index. The 10 mg/kg cA2-treated group's arthritic index was lower then the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

Example 9: Anti-TNF Antibody for the Treatment or Prevention of Type 1 Diabetes (T1D)

Introduction

The Sponsor is requesting a pre-IND Type B meeting to discuss development plans for SIMPONI® (golimumab) administered subcutaneously (SC) in the treatment of Type 1 diabetes (T1D) to determine whether benefit with SIMPONI® can be established in newly diagnosed T1D patients in a Phase 2a efficacy and safety study. This study in a newly diagnosed population would be an initial step in the development program to understand whether SIMPONI® would have benefit in pre-T1D patients to stabilize endogenous insulin production to prevent or delay disease progression.
Product Name and Application Number
SIMPONI® (golimumab)
Chemical Name and Structure
SIMPONI® (golimumab) is a human monoclonal antibody (mAb) with an immunoglobulin G (IgG) 1 heavy chain isotype (Glm [z] allotype) and a kappa light chain isotype. Golimumab has a heavy chain (HC) comprising SEQ ID NO:36 and a light chain (LC) comprising SEQ ID NO:37. Golimumab binds with high affinity to both soluble and transmembrane forms of tumor necrosis factor alpha (TNFα) and inhibits TNFα bioactivity. Golimumab is classified according to the Anatomical Therapeutic Chemical (ATC) Classification System as a TNFα inhibitor (ATC code: L04AB06).

Golimumab is approved under the trade name of SIMPONI® in the United States (US) and a total of 89 countries worldwide as of 6 Oct. 2015 for the treatment of rheumatoid arthritis (RA), psoriatic arthritis (PsA), and ankylosing spondylitis (AS) as a 50 mg SC injection administered once a month as well as in 67 countries for the treatment of ulcerative colitis (UC) as a 200 mg SC injection at Week 0, followed by 100 mg at Week 2 induction regimen, and maintenance therapy with 100 mg every 4 weeks thereafter.

Specifically in the US, SIMPONI® is approved for the following indications:
- in combination with methotrexate (MTX) for the treatment of adult patients with moderately to severely active RA
- alone or in combination with MTX for the treatment of adult patients with active PsA
- for the treatment of adult patients with active AS
- for the treatment of adult patients with ulcerative colitis Dosage Form, Route of Administration, and Dosing The Sponsor intends to use 2 dosage forms in the initial Phase 2a study to support the proposed doses across the target population. These 2 dosage forms are described below:

Prefilled Syringe
Each 50 mg single dose prefilled glass syringe (27 gauge ½ inch needle) contains 50 mg of SIMPONI® per 0.5 mL of solution.

VarioJect
A new pediatric presentation known as the VarioJect is being developed by the Sponsor as a platform device intended for multiple pediatric indications that provides tiered-fixed dosing in pediatric patients who are dosed by body surface area (BSA). The VarioJect is a manual injector capable of delivering doses of 10 mg through 45 mg in 5 mg increments.

Additional details are provided through the specification below and in the figures.

Disease Background
Disease Etiology and Prevalence

In the United States, T1D is one of the three most prevalent chronic diseases of childhood and approximately 3 million people have this disease (Daneman 2006, Stanescu, Lord et al. 2012). The annual incidence is highest in children and adolescents, at ~20 cases/100,000/year in those younger than 20 years old, accounting for nearly 15,000 new cases yearly. (Maahs, West et al. 2010, Stanescu, Lord et al. 2012) In the U.S. and worldwide, the incidence of T1D is on the rise, with increases of ~3-5% per year in most areas (Daneman 2006, Stanescu, Lord et al. 2012). In the US, between 2001 and 2009, the prevalence of T1D in children and adolescents rose by 23%. (JDRF 2013) The diagnosis of T1D increases during childhood and peaks in adolescence: in those 0-4, 5-9, 10-14, and 15-19 years old annual rates are 14, 22, 26, and 13 cases/100,000, respectively (Stanescu, Lord et al. 2012). Comparatively, T1D rates are much lower in adults, with the incidence only up to ~8/100,000 (Molbak, Christau et al. 1994). In children, the clinical course leading to diagnosis is relatively fulminant, with symptoms (ie, polydipsia, polyuria, and weight loss) usually apparent only days or weeks before diagnosis, whereas in adults the course is usually much more indolent, with milder symptoms occurring over months or longer. Children with new-onset and existing T1D frequently suffer the severe metabolic derangement of diabetic ketoacidosis (DKA) during which they are at high risk of cerebral edema, herniation and death.

Data from the past 4 decades demonstrate that T1D results from an autoimmune attack on the pancreatic beta cells (Mordes, Bortell et al. 1996, Eisenbarth 2004, Han, Donelan et al. 2013). A proinflammatory combination of innate and adaptive and cellular and humoral responses is responsible for T1D (Bluestone, Herold et al. 2010). Similar to other autoimmune diseases, T1D is hypothesized to occur in predisposed individuals who encounter a diabetogenic environmental trigger. (Atkinson, Bluestone et al. 2011) A number of HLA- and other immune system-associated genes are linked to T1D susceptibility (van Belle, Coppieters et al. 2011). Those with T1D appear to have abnormalities in both central and peripheral tolerance mechanisms that involve β-cell-reactive T cells (Eisenbarth 2004). Although both dietary and infectious factors have been implicated, none have been found to be causally associated with T1D. It is hypothesized that some environmental encounter activates an inflammatory response, that in predisposed individuals, results in the activation and recruitment of macrophages, dendritic cells, CD4 and CD8 T cells, and B cells to islets (Bluestone, Herold et al. 2010, Atkinson, Bluestone et al. 2011). Soluble factors, including proinflammatory cytokines and beta cell autoantibodies, participate in and amplify this response, and the end result is terminal destruction of beta cells.

Current Treatment Paradigm

Currently the only therapy available for those with T1D is exogenous insulin which must be given as multiple subcutaneous shots every day or by continuous plus pulse insulin via a subcutaneous pump. Insulin, as well as numerous blood glucose checks, are required every day in those with T1D and a careful balance of current blood glucose levels, diet, and exercise must be taken into consideration with every insulin administration to maintain the careful balance between hyper- and hypoglycemia, both of which can be life threatening. There are no adjunctive therapies or disease-modifying therapies available for those with T1D, and glycemic management with exogenous insulin is required for life for those who develop this disease. The positive effect of intensive insulin treatment on the outcome of microvascular complications was demonstrated by the landmark study Diabetes Control and Complications Trial (DCCT) in which subjects enrolled in the intensive treatment cohort (aiming at fasting and premeal blood glucose levels of 70 to 120 mg/dL, postmeal blood glucose levels of 180 mg/dL, and a hemoglobin $A_{1c}$ [$HbA_{1c}$, glycosylated hemoglobin] in the non-diabetic range) had a reduction in the onset and/or progression of nephropathy, retinopathy, and neuropathy relative to subjects enrolled in the conventional treatment cohort.

However, despite the development over the past decades of short- and long-acting insulin analogues that have a more favorable pharmacokinetic and pharmacodynamic profile compared to older generation types of insulin formulations, and the improved technology in insulin delivery devices, many subjects still fail to achieve the recommended target of $HbA_{1c}$ of less than 7%. A recent analysis using data from regional or national registries from 19 countries in Europe, North America, and Western Australia comparing glycemic control in >320,000 subjects with T1DM, showed that overall less than 30% of patients had an $HbA_{1c}$ of <7.5% (McKnight 2015). Limitations associated with T1DM treatments include fear of hypoglycemia, excessive glucose fluctuations, and body weight increases (Cryer 2003, Larger 2005).

The reported incidence of hypoglycemia varies considerably among studies, with greater incidence in both symptomatic and severe hypoglycemia observed in subjects (Cryer 1989). Furthermore, studies using continuous blood glucose measurements over prolonged periods have generally found that the frequency and duration of hypoglycemia, especially the nocturnal hypoglycemia, is even greater than what was previously thought (Guillod 2007, Wentholt 2007). Another factor that prevents patients with T1DM from achieving adequate glycemic is undesirable weight gain which often occurs as a consequence of intensive insulin treatment, with a subsequent reduction of glycosuria. It is estimated that the calories lost in the urine due to the prior poor glycemic control can account for 70% to 100% of the body weight gained when glucose control is improved by an intensified insulin regimen (Carlson 1993). Furthermore, by reversing the metabolic state from catabolism to anabolism, insulin has a lipogenic effect, leading to increase in body fat (Jacob 2006, Nair 1983), and an anti-catabolic effect on proteins leading to increases in lean body mass (Torbay 1985).

Differently from Type 2 Diabetes Mellitus (T2DM) for which many treatment options are available, insulin remains the mainstay of therapy for patients with T1DM. Since the discovery of the therapeutic use of animal insulin in 1922, various types of insulin have been developed, ranging from the traditional insulins to the more modern insulin analogues, with insulin lispro being the first short acting analogue approved by the FDA in 1996, and glargine the first long-acting analogue approved in 2000. Since then, other short and long-acting analogues have been approved and their use has become increasingly common. This is in part due to the need for achieving near euglycemia in subjects with T1DM and the marked increase in risk for severe hypoglycemia seen with non-analogue insulins. Indeed, the vast majority of clinical studies involving long-acting insulins that have compared their efficacy and tolerability to Neutral Protamine Hagedorn (NPH) insulin have shown that generally their once-daily dosing regimen appears to be similar to NPH in terms of glycemic control and are associated with a significantly lower rate of hypoglycemia (particularly at night), and less glucose fluctuation (Ratner 2000, Porcellati 2004, Hermansen 2004, Raskin 2007). With respect to short-acting analogues, these are generally similar to regular insulin in lowering $HbA_{1c}$, while they show other important advantages such as better control in post-prandial hyperglycemia, improved inter- and intra-patient variability, and reduced risk of hypoglycemia. Importantly, due to their improved pharmacokinetics these analogues provide greater flexibility and convenience to the patients, along with better compliance, as the short-acting analogues may be injected immediately before or even after a meal (compared with 30 minutes prior to meals for regular insulin) and the long-acting analogues once-daily (compared to twice daily for NPH).

Given that pramlintide is currently the only non-insulin agent approved as adjunctive therapy in T1DM and the shortcomings of insulin monotherapy, an unmet need exists for novel therapies in T1DM.

Rationale for Studies to Preserve β-Cell Function in New Onset T1D

As described above, the DCCT was a large study conducted in subjects with T1D to evaluate the potential benefits of intensive insulin therapy compared with standard insulin therapy on the development and progression of long-term complications (DCCT 1993). In an important analysis of results from the intensive treatment group from this study, subjects who retained significant residual β-cell function (as measured by C-peptide ≥2 pmol/mL) were compared with subjects who did not retain significant β-cell function (C-peptide <0.2 pmol/mL). Those with residual β-cell function, relative to those without residual β-cell function, were found to have a significantly reduced rate of severe hypoglycemic events and a reduced rate of progression of microvascular complications (DCCT 1987; DCCT 1998; Steffes 2003; Palmer 2004). Additionally, recent evaluation by of data from the DCCT study (Lachin et al) supports short- and long-term clinical benefits in those with stimulated C-peptide of ≥2 pmol/mL, and there does appear to be clinical benefits of maintenance of C-peptide even below the 0.2 pmol/mL threshold.

The notion that maintaining endogenous insulin production has important short- and long-term benefits in those with T1D has been some of the most important justification for numerous interventional trials in new onset T1D in the past 1 to 2 decades. Although an ultimate goal in this field may be "full" remission of T1D (and thus insulin independence), a more realistic, and likely a more achievable goal is to prevent destruction of β-cells present at diagnosis (often considered to be ~10-20% of baseline numbers). Even though individuals may still require some exogenous insulin, metabolic control would be improved and T1D-associated complications would be lessened. Recent data in T1D have supported this concept. Specifically, maintaining some graft function in T1D subjects receiving islet cell transplantation, even in those who have not achieved or lost full insulin independence, severe hypoglycemic events are lessened and glycemic control improved (Agarwal and Brayman 2012, Blau, Abegg et al. 2015). In the interventional, new onset trial of alefacept in T1D, individuals in the treatment arm maintained higher levels of C-peptide production than those in the placebo arm and had approximately half the incidences of major hypoglycemia (defined by BG levels of ≤55 mg/dL), even though insulin independence was not achieved (Rigby, J C I, 2015). Thus in addition to the well-accepted notion that preservation of some endogenous insulin production has important benefits on many long-term, in particular T1D-associated microvascular damage, there are important immediate benefits of lessening hypoglycemia in T1D, a condition which poses the most short-term morbidity and mortality in this disease.

Development Landscape in Type 1 Diabetes

With the elucidation of the autoimmune basis of T1D and following successful studies in rodent models, several small-scale clinical trials were conducted in the 1980s and '90s to evaluate potent, non-specific immune suppressants in patients recently diagnosed with T1D (Bougneres, Carel et al. 1988, Glandt and Herold 2004, Herold, Gitelman et al. 2009). At the time of clinical diagnosis, it is believed a substantial number (perhaps up to 20%) of β-cells remain but are dysfunctional due to exhaustion and local inflammation. These residual cells are likely responsible for the nadir in exogenous insulin often seen in the weeks to months following diagnosis, known as the "honeymoon" period. Early clinical trials used non-selective immune suppressants, including cyclosporine, azathioprine and/or prednisone (Harrison, Colman et al. 1985, Bougneres, Carel et al. 1988, Cook, Hudson et al. 1989, Bougneres, Landais et al. 1990). Although insulin independence was observed in some trials, this effect was lost when immune suppression was stopped. These studies demonstrated that if the inflammatory response to β-cells and the immune attack could be mitigated early in disease, functional beta cells could be spared.

A number of trials using other approaches to reverse diabetes autoimmunity (eg, nicotinamide, anti-oxidants) have been conducted which, taken together, have not shown efficacy (Chase, Butler-Simon et al. 1990, Ludvigsson, Samuelsson et al. 2001). Thus, the only consistent approaches to reverse diabetes autoimmunity have been in studies using potent immune suppressants proven in other conditions, which directly impact the activity of immune cells or their processes. Because of the at-risk population (ie, children) and therapeutic alternative (ie, insulin), an ideal therapy would have low immune to non-immune side effects, and preferably an extended off-therapy effect.

Over the past 2 decades biologic agents have been developed that target specific inflammatory mediators and cells and have significant efficacy in other human autoimmune and inflammatory conditions. A number of these agents have been able to reverse autoimmune disease in rodent models, which has provided the rationale for evaluation in T1D in clinical trials. Studies using anti-CD3, anti-CD20, LFA-3Ig, and CTLA4-Ig have shown the ability to slow, but not halt, beta cell loss (Pescovitz, Greenbaum et al. 2009, Gottlieb, Quinlan et al. 2010, Orban, Bundy et al. 2011, Sherry, Hagopian et al. 2011, Tolerx 2011, Gitelman, Gottlieb et al. 2013, Moran, Bundy et al. 2013); while IL1-beta blockade, anti-CD25, and anti-thymocyte globulin have no effect on β-cell loss (Gottlieb, Quinlan et al. 2010, Gitelman, Gottlieb et al. 2013, Moran, Bundy et al. 2013). As discussed in more detail below, only one class of agent, anti-TNFαs, namely etanercept, was shown in a small Phase I trial to not only preserve endogenous insulin production but actually increase it in newly diagnosed diabetics. Thus, compared to most other autoimmune conditions, no immunomodulatory agent (biologic or otherwise) has been shown to be consistently effective in T1D with a safety profile acceptable for routine use in children, the population that has the most to benefit from a T1D-disease modifying therapy.

Anti-Tumor Necrosis Factor Alpha Inhibitors

Tumor necrosis factor alpha (TNFα) is a principal proinflammatory cytokine produced primarily by macrophages and T cells in response to a variety of stimuli and mediates a wide range of biological activities. It is expressed as a 26 kilodalton (kDa) type II membrane protein that, upon proteolysis, is released as a soluble 17 kDa monomer that self-associates into the biologically active trimeric form. Tumor necrosis factor α is part of the TNF ligand superfamily, a group of related cytokines with overlapping functions that influence cell proliferation and cell death in processes ranging from development to immune response. As indicated by its name, TNFα was initially described as an inducer of apoptosis with murine tumor cell lines, but more recent studies suggest chronic inflammation due to TNFα can lead to tumor promotion and metastasis.

The functional activities modulated by TNFα can include cell activation leading to proliferation, differentiation, induction of cytokine and chemokine production and induction of adhesion proteins, or initiation of programmed cell death. The 2 receptors that engage TNFα are found on virtually all cell types. TNF receptor 1 (TNF-R1) (or p55) contains an intracellular death domain and can signal cytotoxic events, while TNF receptor 2 (TNF-R2) (or p75) appears to be involved in TNFα signaling in lymphocytes. The reasons for the complexity of the physiological response to TNFα production is multifactorial and include the biological form of TNFα present (soluble or transmembrane), the functional receptor (TNF-R1 and/or TNF-R2), accessory proteins, and signaling pathways available in the target cell, the tissue in which it is produced, and the timing and duration of expression.

While limited, local, expression of TNFα is important in the host inflammatory and protective immune response to injury and infectious pathogens, chronic expression of TNFα in specific organs can lead to significant pathology. High levels of TNFα have been implicated in the pathophysiology of diseases such as rheumatoid arthritis (RA), psoriatic arthritis (PsA), ankylosing spondylitis (AS), inflammatory bowel disease and T1D. Inhibition of TNF has been shown to mitigate disease activity in animal models of arthritis and colitis, and this has led to the successful clinical and commercial development of anti-TNFα agents, including the monoclonal antibodies (mAbs) golimumab, infliximab, adalimumab, and certolizumab pegol; and the soluble TNF receptor p75 fragment crystallizable (Fc) fusion protein, etanercept, for the treatment of immune-mediated inflammatory diseases such as RA, inflammatory bowel disease, and adjacent indications.

Mechanism of TNF Blockade in Type 1 Diabetes

Studies have shown that TNFα is a proinflammatory cytokine is critical in the autoimmune process and beta cell destruction in T1D. (Cavallo, Pozzilli et al. 1991, Rabinovitch 1998) Tumor necrosis factor-α produced by activated macrophages, dendritic cells, and CD4+ T cells promotes inflammation via its participation in the acute phase response, pro-proliferative effects, and activation and recruitment of other cells in the innate and adaptive immune response. Tumor necrosis factor-α, dendritic cells (DCs), monocytes, and CD4+ T cells are all found in the insulitic lesion in T1D, and all are implicated in beta cell inflammation (insulitis) and beta cell killing. (Cavallo, Pozzilli et al. 1991, Rabinovitch 1998) In preclinical studies, systemic treatment of non-obese diabetic (NOD) mice (a model of spontaneous autoimmune diabetes) with TNFα early in life increases the frequency and accelerates diabetes onset. Treatment with antibodies to TNFα slows the onset, decreases the frequency, and in some cases fully prevents diabetes. (Rabinovitch 1998) In some non-diabetes-prone mouse strains (eg, C57BL/6), systemic treatment with TNFα results in insulitis. (Rabinovitch 1998) Transgenic expression of TNFα in NOD mice islets (NF-α-NOD), which express TNFα early in life, accelerates disease progression. (Koulmanda, Bhasin et al. 2012) No studies have specifically used a TNFα inhibitor to prevent or reverse diabetes in rodent models of T1D.

Tumor necrosis factor-α appears to promote diabetes autoimmunity by enhancing the recruitment of inflammatory cells to the islets, activating cells and enhancing autoantigen presentation. (Rabinovitch 1998, Kodama, Davis et al. 2005) Tumor necrosis factor-α activates vascular endothelium, upregulating MHC I and adhesion molecules. (Argiles, Lopez-Soriano et al. 1994) In murine models of T1DM, some of the first cells to infiltrate islets are dendritic cells (DCs). (Argiles, Lopez-Soriano et al. 1994, Rabinovitch 1998) Dendritic cells and other antigen-presenting cells (APCs), which are critical for β-cell antigen presentation to T cells, are activated by TNFα by up regulation of MHC I and II and costimulatory molecules. (Rabinovitch 1998, Kleijwegt, Laban et al. 2010) Tumor necrosis factor-α also directly increases MHC I, and synergizes with IFNγ to upregulate MHC II, on beta cells, both of which appear to increase their susceptibility to T cell killing. (Atkinson, Bluestone et al. 2011)

In addition, there are important non-immune effects of TNFα that make blocking it attractive in T1D. Tumor necrosis factor-α has direct cytostatic effects and impairs insulin production and secretion, and it has cytocidal activity, killing beta cells directly. (Mandrup-Poulsen, Bendtzen et al. 1987, Kawahara and Kenney 1991, Dunger, Schroder et al. 1995, Rabinovitch 1998) Tumor necrosis factor-α also impairs insulin signaling and increases peripheral insulin resistance, which in experimental models can be reversed by blocking TNFα. (Rabinovitch 1998, Koulmanda, Bhasin et al. 2012) Patients with new-onset T1D have elevated serum TNFα levels compared with those with long-standing disease or healthy controls. (Cavallo, Pozzilli et al. 1991) There are case reports of patients with T1D who were started on TNFα blockers for other autoimmune diseases in whom insulin requirements dropped due to an apparent increase in insulin sensitivity. (Yazdani-Biuki, Stelzl et al. 2004, Boulton and Bourne 2007, van Eijk, Peters et al. 2007, Arif, Cox et al. 2010) Therefore, TNFα also has potent metabolic effects that may contribute to diabetes by increasing beta cell stress and death.

Data to support a role of TNFα in T1D, and that blocking it may have the ability to modify the course of disease in humans, comes from a report of a small, pilot clinical trial of etanercept in newly diagnosed T1D conducted by Mastrandrea et al. (Mastrandrea, Yu et al. 2009) Eligibility included patients aged 3-18 years, ~6 weeks from diagnosis, who were diabetes autoantibody (i.e., GAD-65 and/or islet cell antibody) positive, had normal WBC and platelet counts, and normal liver and renal function. Patients received etanercept 0.4 mg/kg (maximum 25 mg) dosed subcutaneously twice weekly for 24 weeks or placebo. The study enrolled 18 subjects (mean age ~12.5 years), 10 into the etanercept arm (0.4 mg/kg SQ twice weekly×24 weeks) and 8 into the placebo arm. Patients were followed for 6 months. Etanercept-treated participants showed lower insulin requirements and lower HbA1c than placebo participants, and, importantly, a 39% increase in C-peptide production from baseline assessed by 2-hour area under the curve (AUC)C-peptide level in response to a mixed-meal tolerance test (MMTT) was seen. In contrast, placebo group had a 20% decrease in C-peptide production. There were no severe adverse events in either group. Three etanercept-treated patients reported mild, transient paresthesias, but otherwise the frequency of adverse events (all mild) was similar in the two groups. Although there has been no follow up on these very promising initial observations, the Sponsor contends that the data generated in this study will provides vital rationale for a potential benefit of TNFα blockers in T1D and justify further study in this population.

The above evidence from preclinical and clinical studies demonstrates that TNFα has a critical role in T1D development and progression. There are immune, direct toxic, and metabolic effects of TNFα that suggest that blocking this cytokine is a very attractive approach to further investigate clinically. The fact that there are no disease modifying therapies available for those with T1D, and that there continues to be severe short and long-term morbidity and mortality even with the best glycemic control with insulin, supports the notion that there is a significant unmet need to find therapies to improve the course, glycemic control, and lives of those with T1D.

As discussed above, in T1D, like many other autoimmune disorders, TNFα appears to play a key role in disease initiation and progression. The clinical utility of TNFα blockade in other autoimmune disorders is well established. There are a number of FDA-approved agents to block TNFα, including adalimumab, golimumab, infliximab, certolizumab pegol and etanercept, and this class of biologic therapies has been the most extensively evaluated, prescribed and, have been successful in the treatment of a spectrum of autoimmune diseases in adults and children such as rheumatoid arthritis, psoriasis, psoriatic arthritis, ankylosing spondylitis, ulcerative colitis and Crohn's disease. There are a number of off-label and experimental uses for TNFα inhibitors. This includes allogeneic islet transplant regimens, where adding TNFα inhibitors have shown to improve graft survival, perhaps reflecting both beneficial immunologic and metabolic effects of blocking TNFα on beta cell survival in this indication. Golimumab, infliximab, certolizumab pegol and adalimumab are monoclonal antibodies that bind TNFα; whereas etanercept is a fusion protein consisting of the TNF receptor bound to an IgG tail and also binds lymphotoxin alpha (LTα). Lymphotoxin alpha appears to have a role in rodent autoimmune diabetes, but has not been shown to be directly involved in human T1D. With respect to clinical use in children, etanercept has been FDA-approved in children 2 years old and above with JIA since 1999, infliximab was approved in children 6 years old and above with Crohn's disease and ulcerative colitis in 2009 and 2011, respectively and adalimumab was approved for JIA in those 2 years old and above in 2008 and Crohn's disease in those 6 years old and above in 2014. Golimumab has been studied in over 200 children age 2 years old and above with JIA and pediatric UC. In addition to efficacy, the safety profiles of these agents in children are well documented and similar to the safety profile in adults across numerous indications.

In summary, there is strong pre-clinical and clinical data implicating TNFα in the immune and metabolic pathogenesis of T1D, and that blocking TNFα has the ability to interfere with diabetes autoimmunity and preserve beta cells. There is almost 2 decades of successful clinical experience of TNFα-blockers with in a variety of human autoimmune diseases, including in children as young as 2 years old. T1D continues to be a significant burden on individuals, their families and society and there is a significant unmet need for a disease modifying therapy in T1D which can assist in maintaining endogenous beta cell function and lessen the short- and long-term sequelae of this disease.

Clinical Experience with Golimumab

Adult Program

Description of Overall Development Program Across Indications

SIMPONI® (golimumab) administered as a SC injection is currently approved in the US for adults for the treatment of moderately to severely active rheumatoid arthritis (RA) in combination with methotrexate (MTX); active psoriatic arthritis (PsA), alone or in combination with MTX; active ankylosing spondylitis (AS); and moderately to severely active UC in patients with an inadequate response to or intolerance of prior treatments or requiring continuous steroid therapy.

The approved dosage in the adult rheumatology indications is 50 mg administered by SC injection once a month. The approved dosage for adults with UC is a 200 mg SC injection at Week 0 followed by 100 mg SC at Week 2 as induction (200 mg→100 mg), followed by maintenance therapy of 100 mg SC q4w.

Established Safety Profile

Long-term safety (safety extensions for up to 5 years) has been evaluated in studies for RA, AS, and PsA, and a long-term extension of approximately 4 years of follow-up has been completed in UC. More than 11,000 subjects have been exposed to golimumab in clinical studies, and since the product launch, another estimated 393,000 patients have been exposed to golimumab worldwide as of 6 Oct. 2015. (A listing of the all clinical studies in the program, along with the number of subjects exposed in each study is provided in Table 8).

The safety profile of golimumab is consistent with drug products in the TNFα inhibitor class.

The ADRs observed for golimumab in clinical studies are presented in Table 7.

The ADR frequencies in Table 7 are based on data from 5,717 golimumab-treated subjects in the Phase 2 and 3 clinical studies: 3,090 subjects in RA studies (C0524T02, C0524T05, C0524T06, C0524T11, C0524T28, C0524T12, and CNTO148ART3001), 394 subjects in the PsA study (C0524T08), 564 subjects in the AS studies (C0524T09, C0524T29), 1,245 subjects in UC studies (C0524T16, C0524T17, and C0524T18), 231 subjects in the severe, persistent asthma study (C0524T03), and 193 subjects with active nr-axial SpA (P07642 [MK-8259-006]).

The ADRs listed in the table below are classified according to frequency and SOC. The frequency categories are defined in the footnote of the table as Very common, Common, Uncommon, Rare, Very rare, and Not Known.

TABLE 7

Summary of golimumab adverse reactions in clinical studies

| | |
|---|---|
| Infections and infestations | |
| Very common: | Upper respiratory tract infection (nasophalyngitis, pharyngitis, laryngitis, and rhinitis) |
| Common: | Bacterial infections (such as cellulitis), lower respiratory tract infection (pneumonia), viral infections (such as influenza and herpes), bronchitis, sinusitis, superficial fungal infections, abscess |
| Uncommon: | Sepsis including septic shock, opportunistic infections (invasive fungal infections, bacterial, atypical mycobacterial and protozoal), arthritis bacterial, pyelonephritis |
| Rare: | Hepatitis B reactivation, histoplasmosis, coccidioidomycosis, pneumocystosis, tuberculosis, bursitis infective |
| Neoplasm benign and malignant | |
| Rare: | Lymphoma, leukemia |
| Not known: | Pediatric malignancy* |
| Investigations | |
| Common: | Alanine aminotransferase increased, aspartate aminotransferase increased |
| Uncommon: | Neutrophil count decreased |
| Blood and lymphatic system disorders | |
| Common: | Anemia |
| Uncommon: | Leukopenia, thrombocytopenia, pancytopenia |
| Immune system disorders | |
| Common: | Autoantibody positive, non-serious allergic reactions |
| Nervous system disorders | |
| Common: | Dizziness, paraesthesia |
| Rare: | Demyelinating disorders (central and peripheral) |
| Cardiac disorders | |
| Rare: | Congestive heart failure (new onset or worsening) |
| Vascular disorders | |
| Common: | Hypertension |
| Rare: | Vasculitis (systemic) |
| Respiratory, thoracic and mediastinal disorders | |
| Uncommon: | Interstitial lung disease |
| Gastrointestinal disorders | |
| Uncommon: | Constipation |
| Skin and subcutaneous tissue disorders | |
| Common: | Rash, alopecia |
| Uncommon: | Psoriasis: new onset, palmar/plantar, and pustular |
| Rare: | Vasculitis (cutaneous) |
| Musculoskeletal and connective tissue disorders | |
| Rare | Lupus-like syndrome |
| General disorders and administration site conditions | |
| Common: | Pyrexia, injection site reaction (injection site erythema, urticaria, induration, pain, bruising, pruritus, irritation, paraesthesia) |

*Observed with other TNFα blockers, but not observed in clinical studies with golimumab.

Pediatric Program
Description of Overall Pediatric Development Program Across Indications Golimumab is not currently approved for the use in pediatric patients. However, a study of SC golimumab in children with pJIA (CNTO148JIA3001) was conducted and a clinical development program with subcutaneously administered golimumab in pediatric UC is currently ongoing (CNTO148UCO1001).

CNTO148JIA3001 was a Phase 3, multicenter, double-blind, randomized withdrawal study with the primary objective to assess the clinical efficacy of SC administration of golimumab in pediatric subjects (ages 2 to less than 18 years) with pJIA manifested by ≥5 joints with active arthritis despite methotrexate (MTX) therapy for ≥3 months. The CNTO148JIA3001 study consisted of an open label phase where patients received SC golimumab 30 mg/m$^2$ q4w+MTX for 16 weeks, followed by a randomized withdrawal phase where patients who achieved an American College of Rheumatology (ACR) pediatric (Ped) 30 response at Week 16 received either golimumab 30 mg/m$^2$+MTX or placebo+MTX q4w through Week 48. There was also a long-term extension in which the median follow-up was approximately 2 years. A total of 173 subjects (75.7% female; 24.3% male) were enrolled in the study, and 154 subjects entered the randomized withdrawal phase at Week 16. The mean age was 11.2 years (52.0% aged 12 to 17 years; 48.0% aged 2 to 11 years) and the mean weight was 43.1 kg.

CNTO148UCO1001 was a Phase 1b, multicenter, open-label study to assess the PK, safety, and efficacy of golimumab in children with pediatric UC. This multicenter, open-label study enrolled pediatric subjects aged 2 through 17 years with moderately to severely active UC who demonstrated an inadequate response to, failed to tolerate, or had medical contraindication to conventional therapies (ie, IV or oral corticosteroids or the immunomodulators AZA or 6-MP), and were naïve to anti-TNFα agents. Subjects received weight-based dose regimens of SC golimumab as follows:

Subjects with body weight <45 kg: 90 mg/m$^2$ at Week 0 and 45 mg/m$^2$ at Week 2, and 45 mg/m$^2$ q4w starting at Week 6 among Week 6 responders Subjects with body weight ≥45 kg: 200 mg at Week 0 and 100 mg at Week 2, and 100 mg q4w starting at Week 6 among Week 6 responders The study was divided into 2 parts: the PK portion through Week 14, and the study extension through Week 126. The 14-Week PK portion of Study 1 (CNTO148UCO1001) has been completed and the study extension is ongoing. A total of 35 subjects (51.4% female; 48.6% male) were enrolled in study. The mean age was 13.4 years (71.4% aged 12 to 17 years; 28.6% aged 2 to 11 years) and the mean weight was 51.7 kg.

Established Safety Profile

Golimumab was well tolerated in pediatric subjects of 2 to <18 years of age. In general, the safety profile of golimumab in the pJIA and pediatric UC studies including the type and frequency of the adverse reactions seen was consistent with the known safety profile for the adult populations studied and consistent with other TNFα inhibitors. No new safety signals were observed.

Proposed Phase 2a New Onset T1D Study—CNTO148DML2001

The Sponsor is planning a Phase 2a new onset T1D study in newly diagnosed T1D patients to evaluate the effect of SIMPONI® on the preservation of β-cell s for maintenance of endogenous insulin. The results of this study will provide key information on whether SIMPONI® via TNFα blockade impacts T1D disease progression and support further development in new onset disease as well as in a "pre-disease" state, prior to onset of symptoms and requirement for exogenous insulin. The key aspects of this study are outlined below.

Study Design

This is a Phase 2a, randomized, double-blind, placebo-controlled, parallel-group, multicenter study of golimumab in subjects with T1D. Approximately 81 subjects of 6 to 21 years of age will be randomly assigned in a 2:1 ratio to receive golimumab or placebo, administered subcutaneously (SC). Study subjects who weigh <45 kg who are randomized to the golimumab treatment group will receive an induction dose of SC golimumab 60 mg/m$^2$ at Weeks 0 and 2 followed by a maintenance dose of 30 mg/m2 at Week 4 and q2w through Week 52. Study subjects who weigh ≥45 kg who are randomized to the golimumab treatment group will receive an induction dose of SC golimumab 100 mg at Weeks 0 and 2 followed by a maintenance dose of SC golimumab 50 mg at Week 4 and q2w through Week 52 (Section 0). Subjects randomized to the placebo treatment group will receive a SC placebo injection q2w through Week 52 (FIG. 18). To facilitate recruitment and retention of subjects, the Sponsor will allow self-administration of study agent at home.

During the study, all subjects will receive intensive management of their diabetes with exogenous insulin. Subjects, and when applicable their caretakers, must agree to follow the current recommendations of tight glycemic control with specific HbA1c targets as defined by the American Diabetes Association. These current recommendations are intended to achieve glucose levels that appear to decrease some of the short- and long-term sequela of T1D. Specific to this study, this will include a HbA1c target of less than 8% for those aged 6 to 12 years, less than 7.5% for those between from age 13 through 18 years, and less than 7% for those 19 years old and above. The subject's glycemic control will be monitored by the subject's primary care physician. In addition, HbA1c and other parameters of glycemic control will be assessed at screening, and during the study.

Study Population

Males and females 6 through 21 years of age with newly diagnosed T1D will be enrolled in this study. Participants will meet accepted criteria for enrollment in new onset T1D studies including meeting the current ADA definition of T1D, being positive for at least 1 of 5 recognized T1D autoantibodies, showing evidence of residual β-cell function (defined by a peak c-peptide of at least 0.2 pmol/mL following a mixed-meal tolerance test), and randomization in the trial within 100 days of T1D diagnosis. Exclusion criteria will focus on identifying individuals who may be at any particular risk due to immune or infectious risks if included in the trial.

The age range was chosen for the following reasons:
Unique Attributes of TID in Children and Young Adults Compared to Older Adults:

Recent data have confirmed that there are important differences in T1D disease in children and younger adults (ie, through ~age 21) and older adults. It is accepted that there are a number of clinical differences in the presentation and course of disease in younger and older individuals with newly diagnosed T1D, including what can be described as a more aggressive presentation (ie, more rapid need for full insulin replacement) and initial course in the younger group. In a recent report by Greenbaum et al that conducted a thorough evaluation of the natural history of c-peptide decline in placebo subjects in a number of recent new onset T1D studies, the findings showed similar rates of c-peptide decline in those ~7-21 years old with a more rapid decline than in those >21 years old, strongly suggesting that there is a different immunopathology in these "younger" and "older" individuals. In addition, to support this contention, in some immunotherapeutic trials in T1D there is different efficacy in the younger and older individuals. For example, alefacept (LFA3-Ig) and abatacept (CTLA4-Ig) appear to have preferential effects in younger individuals (<18 to 21 years of age) while thymoglobulin appears to have a beneficial effect only in older individuals (>21 years of age; (Gitelman, Gottlieb et al. 2013, Orban, Bundy et al. 2014, Rigby, Harris et al. 2015). Due to the nature and course of T1D and the lifelong and cumulative morbidity and mortality associated with this disease, those that will be most positively impacted by a therapy that slows or stabilizes disease progression are children and young adults. Because of the aforementioned differences in disease in this population compared with older adult individuals, the direct study of children and young adults with T1D is essential to most appropriately develop a disease modifying therapy that will be most impactful in this disease.

Data Supporting a Prospect of Benefit of TNFα Blockers in New Onset T1D in Children:

The Sponsor recognizes that demonstrating a clinical benefit with a therapeutic intervention in an adult population is sometimes desired prior to evaluation in a pediatric population. However, from the small etanercept pilot study (also referenced above), conducted by investigators at the University of Buffalo showed that there were beneficial effects on c-peptide production, HbA1c and exogenous insulin use in children 7-18 years old (protocol allowed for children as low as 3 years of age) with a 24 week course of the TNFα-blocker etanercept. Although this was a small trial (18 total participants with 10 receiving etanercept), the results were extremely promising, showing that there was on average an increase in endogenous insulin production with etanercept at 24 weeks versus at time of enrollment, during a time when there was loss in c-peptide in the placebo group. Given these results, and considering the extensive experience with golimumab and other TNFα blockers in both adult and pediatric indications, The Sponsor contends that the prospect of benefit for TNFα-blockade in children with newly diagnosed T1D has been demonstrated and therefore it is appropriate to evaluate golimumab in this particular population as a disease-modifying therapy.

Extensive Safety and Efficacy Experience of TNFα Blockers Including Golimumab

The Sponsor recognizes that some of the intended study population, in terms of age, may be considered a particularly susceptible population to evaluate immune therapies. We believe that in the case of golimumab itself and as a member of the class of TNFα-blockers, there is robust safety (and efficacy) experience in children down to the age of 2 in other autoimmune diseases. Etanercept has been FDA-approved in children 2 years old and above with JIA since 1999. Infliximab was approved in children 6 years old and above with Crohn's disease and ulcerative colitis in 2009 and 2011, respectively. Adalimumab was approved for JIA in those 2 years old and above in 2008 and Crohn's disease in those 6 years old and above in 2014. Golimumab has been studied in over 200 children ages 2 years old and above with JIA and is currently under registration for this indication in Europe. In addition all of the above agents are approved for a wide variety of autoimmune conditions in adults, including rheumatoid arthritis, Crohn's disease, ulcerative colitis and psoriasis. Thus, the safety and side effect profiles of TNFα-blocking agents, including golimumab, are well established not only in adults, but specifically the pediatric population, likely much more than any other immunotherapy that has been evaluated in T1D.

Taken together, there is strong rationale to focus the golimumab study in new-onset T1D on younger individuals and include only children and young adults 6 to 21 years old. Not only is there robust specific efficacy and safety data from golimumab and the class of TNFα-blockers in pediatric autoimmunity, but there has been extremely promising data in this younger age range that TNFα-blockade has the ability to slow, if not reverse, the loss of β-cells in those newly diagnosed T1D, thus meeting a critical bar of a "prospect of benefit" of TNFα-blockade in this age group. It is well agreed, and shown, that T1D diabetes is different in younger versus older individuals and that there can be a significantly different responses to immune therapy in these groups, where efficacy (or lack thereof) in one group may actually be misinformative to the other. The Sponsor is choosing the upper age "cut-off" as age 21, as many of these studies appears to show a differentiating break in the "younger" and "older" disease at this age. Age 6 has been an accepted lower age of enrollment in other new onset T1D studies (ie, abatacept and canakinumab) and is also the age cutoff for approved UC in children and inclusive of the JIA age range for the class of approved TNFα-blockers.

Dose Selection

The proposed dosing of golimumab in this trial integrates knowledge regarding disease-specific considerations in T1D, an understanding of the comparative efficacy of TNFα inhibition of etanercept in the aforementioned pilot trial in children with T1D, and the sponsor's experience with golimumab. In T1D, the destruction of β-cells is irreversible and appears to be rapid at the onset of clinical disease. For more inflammatory immune-mediated diseases, higher or more frequent induction doses followed by lower maintenance doses are often used, such as with the use of anti-TNFα agents for Crohn's disease and ulcerative colitis.[7,8,9] For T1D, there is also a need to quickly suppress disease activity to prevent further destruction of β-cell present at enrollment in study. Given that golimumab steady-state concentrations are generally established after 12 weeks, induction doses should be employed followed by a maintenance dosing regimen in order to achieve steady-state concentrations earlier to offset further β-cell loss. Data from previous adult and pediatric studies were evaluated along with population PK and mechanistic PK/target engagement (TE) modeling to determine the proposed dosing regimen for this Phase 2a new onset T1D study.

Considering the anticipated need for induction and maintenance dosing in T1D, various BSA-adjusted dose regimens were explored via simulation with a population PK model and a mechanistic PK/TE model that assesses free TNFα suppression. The population PK model for golimumab was based on an established polyarticular JIA model in which all subjects were on concomitant methotrexate (MTX). Since MTX has been previously shown to affect golimumab exposures and patients with T1D are not expected to be concomitantly treated with methotrexate, a 36% increase in golimumab clearance was accounted for in the simulations (FIG. 19). Analysis of subjects 6 to 21 years old using the CDC growth charts for height and weight were performed comparing the proposed T1D dosing regimen to JIA (FIG. 19 Panel A) and ped UC (FIG. 19 Panel B) with dosing regimens that have already been studied in the pediatric population. The simulations were based on the established JIA population PK model with faster clearance of golimumab (36%) due to non-co-administration of MTX in the T1D population. For a child, golimumab 30 mg/m² (50 mg/1.67 m²) would be approximately equivalent to 50 mg dose for an adult subject weighing 60 kg (with BSA of 1.67 m²). Thus the 30 mg/m² dose is designed to be similar to the 50 mg dose in adults and the 60 mg/m² dose to be similar to the 100 mg dose in adults. Based on these simulations, PK exposure for the proposed T1D dosing regimen is expected to be between the JIA and ped UC exposure (both simulated without MTX), though the q2w maintenance dosing interval will result in slightly higher trough concentrations. In adults, golimumab 50 mg q4w was the minimum effective dosing regimen for the treatment of RA, PsA, or AS. Due to the absence of concomitant MTX in T1D subjects, it is expected that the 30 mg/m² q4w dosing regimen that is the pediatric equivalent to the adult 50 mg q4w dose may not result in sufficient systemic exposure for suppressing TNFα; therefore the Sponsor contends a higher dose or more frequent dosing interval should be studied.

The mechanistic PK/TE model incorporated PK exposure from the above population PK model (with 36% higher clearance without concomitant MTX) paired with a target-mediated drug disposition (TMDD) model was used to assess the interaction between drug and target and to simulate the suppression of TNFα after anti-TNFα administration (FIG. 20). The PK/TE model was developed based on the assumption that the etanercept dosing regimen tested in T1D results in adequate TNFα suppression given the positive results previously observed.[6] The TNFα kinetic parameters were obtained from preclinical studies and allometric scaling, and the same set of TNFα kinetics parameters were used to compare the effect of golimumab and etanercept. TNFα suppression in the systemic circulation was also assumed to be representative of that in the pancreas. The golimumab dosing regimen was designed to approximate the extent of TNFα suppression following the etanercept dosing regimen in the pilot trial in children with new onset T1D,[6] (Mastrandrea, 2009), after accounting for the differences in PK and TNFα binding affinity between golimumab and etanercept. The PK/TE model suggested that an induction dose regimen of 60 mg/m² SC (to a maximum of 100 mg) at Week 0 and Week 2 followed by a maintenance dose regimen of 30 mg/m² SC (to a maximum of 50 mg) q2w or 60 mg/m² SC (to a maximum of 100 mg) q4w allows suppression of TNFα to a level closer to approximating that of etanercept, in contrast to the 30 mg/m² SC q4w maintenance dose (FIG. 20). The 30 mg/m² q2w and 60 mg/m² q4w maintenance dose regimens would have the same overall exposure (AUC) and similar TNFα suppression; however, the 60 mg/m² q4w regimen would have higher peak/trough concentration fluctuation and thus more fluctuation on suppression of TNFα. It is known that TNFα has direct cytostatic and cytocidal effects on beta cells. Thus the TNFα elevations that would be expected to occur during the troughs with the higher, but less frequent dosing, may be damaging to residual beta cells. As the golimumab exposure of these dosing regimens may be considered equivalent, the 30 mg/m² SC (to a maximum of 50 mg) q2w dose regimen was preferred as the simulations have shown the q2w maintenance dosing interval will result in slightly higher trough concentrations resulting in a smaller peak/trough fluctuation in an attempt to optimally protect β-cells from the direct effects of TNFα.

The safety and efficacy of golimumab has been extensively characterized in subjects with RA, PsA, AS and UC. In a Phase 2 study in subjects with RA, 4 different dosing regimens were evaluated (50 mg q2w or q4w and 100 mg q2w or q4w) of which all doses tested were generally well tolerated and effective in maintaining clinical response through Week 52. In pJIA, a 30 mg/m² q4w dosing regimen was studied up to a maximum of 50 mg (the approved adult RA dose). In ped UC, subjects below 45 kg received SC induction doses of 90 mg/m² (to a maximum of 200 mg) at Week 0 and 45 mg/m² (to a maximum of 100 mg) at Week 2 followed by a maintenance dosing regimen of 45 mg/m² (to a maximum of 100 mg) SC q4w while subjects 45 kg and above received induction doses of 200 mg at Week 0 and 100 mg at Week 2 followed by a maintenance dose of 100 mg q4w. To date, the dosing regimens studied were well tolerated overall with no new adverse drug reactions identified with frequency, type and severities similar to those observed in the adult rheumatology and IBD studies. In conclusion, considering disease specific issues of T1D, pharmacologic comparisons of golimumab and etanercept and specific clinical experience with golimumab, the 60 mg/m² SC (to a maximum of 100 mg) at Week 0 and Week 2 induction followed by a 30 mg/m² SC (to a maximum of 50 mg) q2w was selected as the recommended dose regimen. A weight cut-off (45 kg) will also be studied such that patients over the weight cut-off will receive golimumab from the already approved adult PFS presentations. The Sponsor used both disease- and therapy-specific considerations to develop this dosing regimen in an attempt to give this proof-of-concept trial the best opportunity for success. Although not a regimen specifically used in the past, the proposed T1D dosing regimen will achieve golimumab exposures observed between the aforementioned JIA and UC dosing in children (which the Agency has supported for study in overlapping age ranges) and thus mitigate safety concerns with this specific approach. If this trial is successful, considerations for dose ranging will be explored in subsequent clinical studies.

Duration of Treatment

Subjects will receive SC golimumab or placebo through Week 52. In part, a goal of this trial is to reproduce and extend findings of the 24 week pilot clinical trial of etanercept in T1D showing the β-cell sparing by neutralizing TNFα. Due to the natural history of β-cell loss following diagnosis documenting a statistically significant and clinically meaningful positive effect of a β-cell sparing agent in a trial of a reasonable size is most probable at approximately 1 year, and an accepted major (including primary) endpoint is the provoked c-peptide production at 12 months. In approved indications, golimumab is used as a chronic therapy and thus the proposed length of treatment is consistent with clinical use of this agent. Through a year of on-therapy evaluation, with an additional off-therapy evaluation, we believe we will obtain important efficacy and safety data to help guide further clinical development of this therapy in T1D.

Rationale and Selection of Major Endpoints

The major trial endpoints in study CNTO148DML2001 will be consistent with those used and accepted by leading T1D research networks (including T1D TrialNet and the Immune Tolerance Network) and cited by major health authority guidelines (including those of the FDA and EMA). Specifically, the primary endpoint is to stimulate c-peptide response (4 h AUC) following a mixed-meal tolerance test at Week 52, as an objective measure of endogenous insulin production. As this will be a placebo-controlled trial, a positive study will be defined as showing a statistically significant difference in the c-peptide AUC in the active versus placebo treatment groups at Week 52. Provoked c-peptide evaluations will also be conducted at approximately Weeks 13, 26, 39, 78, and 104 as secondary endpoints. The goal of these evaluations is to obtain insight on the time course of the effect of golimumab on β-cell preservation (Weeks 12, 26, and 38) and the off-therapy durability of response (Weeks 78 and 104 evaluations). Major secondary endpoints will evaluate other potential positive effects on glycemic control (HbA1c), insulin use (in U/kg/day), and rates of hypoglycemia (including levels ≤70, 55, and 35 mg/dL).

Safety Monitoring

In addition to evaluating the efficacy of golimumab in preventing the continued loss of β-cell function, there will be extensive safety evaluation. As an immune modulator, the focus of these evaluations will be to determine if there are increase risks of infection or untoward effects on immune status. This will include careful documentation of signs or symptoms of local or systemic infections during study visits and at home (using patient reported outcomes). The Sponsor will also be monitoring white blood cell counts and for indications of dampened immune response via regular evaluation of EBV and CMV status. Due to the experience of golimumab and other TNFα blockers, the Sponsor anticipates the likelihood of non-immune side effects to be low, but we will be monitoring for any clinical or chemical evidence of such effects via physical examinations and laboratory evaluations including renal function tests, liver function, and hematologic tests. The goal of this project is to determine if there is a beneficial effect on the progression of T1D, and although not expected, the Sponsor will be able to use the evaluations for this to determine if there are endocrinologic adverse effects, such as increased rates of hypoglycemia, poorer glycemic control or more rapid loss of endogenous beta cell function.

An independent, external Data Monitoring Committee (DMC) will be established to monitor data on an ongoing basis to ensure the continuing safety of the subjects enrolled in this study. The committee will meet periodically to review interim data. After the review, the DMC will make recommendations regarding the continuation of the study. The safety reviews will focus on particular AEs, SAES, and mortality.

SAE reports will be provided to the DMC members on an ongoing basis. The DMC will have access to unblinded data and review tabulated safety summaries (if appropriate) and any additional data that the DMC may request during the conduct of the study. No formal statistical hypothesis testing is planned. In addition, during the study, the Sponsor's study responsible physician (or designee) will regularly review blinded safety data from the sites and notify the DMC and appropriate Sponsor personnel of any issues. The protocol to be submitted with the Investigational New Drug (IND) Application to the Agency will describe all safety assessments and monitoring to be performed in this study and the makeup and roles and responsibilities of the DMC including specific stopping rules.

One important safety measure also includes exclusions of subjects who have immune suppression due to concurrent disorders or therapies, and exclude individuals with existing or history of significant infections, including tuberculosis.

Methods of Administration

Given the proposed regimen of q2w dosing during the maintenance portion of the Phase 2a study, the option for at-home administration is expected to aid in a patient's routine (ie, not needing to visit the site of care for every dose) and also increase study enrollment and retention. If a patient or caregiver is to perform at home administration, he/she should be instructed in injection techniques, and their ability to inject subcutaneously should be assessed to ensure the proper administration. In addition, it is recommended that the first self-injection or caregiver injection be performed under the supervision of a qualified healthcare professional.

Presentation Proposed for Use in the Phase 2a New Onset T1D Study

Ultrasafe

For pediatric subjects with body weight ≥45 kg, golimumab will be administered subcutaneously using the 50 mg PFS-U device, which is already approved for use in adults. For additional details, see below and FIG. 21.

SIMPONI® UltraSafe Passive® Needle Guard (PFS-U)

The UltraSafe is a manually-operated, single-use, disposable needle guard system that is an accessory to a prefilled syringe and is intended for use as a safety mechanism to reduce the occurrence of accidental needlesticks to healthcare professionals and patients or their caregivers after administration and during disposal of a used prefilled syringe. The UltraSafe accepts either a 0.5 mL or a 1.0 mL PFS. There is no direct drug product contact with the device whatsoever, either during assembly or use.

The device's clear plastic construction and the design of the viewing slot permit visualization of the syringe. The passive nature of the device permits normal needle insertion and when the plunger stopper of the syringe is fully advanced and the drug dose is delivered, the spring-aided guard is released. The guard automatically advances over the syringe and needle as the user relaxes their grip until it latches in a locked position.

The features of the UltraSafe are illustrated in FIG. 21

VarioJect

The Sponsor is developing a pediatric presentation known as the VarioJect as a platform device across multiple pediatric programs to facilitate BSA-dosing, and is planning to utilize the VarioJect device for this study. The Sponsor has previously discussed the data required to support the registration of the VarioJect device in other pediatric programs for SIMPONI® which include actual use and label comprehension assessments, data from a human factor study, and additional device performance data.

Dosage and device selection charts (Table 9) will be developed to allow healthcare providers, caregivers, and/or pediatric subjects (as applicable) to determine the corresponding absolute milligram (mg) dose and the combination of injection devices to be used.

SIMPONI® VarioJect

The VarioJect device would be intended for delivery of a single dose of drug, based on the BSA dose regimen, ranging from doses of 10 mg to 45 mg, in 5 mg increments. The VarioJect device is designed to be assembled with the same 1 mL Becton Dickson Hypak syringe containing 0.5 mL of SIMPONI® drug product (PFS) that has been used in the already approved SIMPONI SmartJect autoinjector and PFS-U. Note that the VarioJect device has no contact with the drug product, and therefore, the VarioJect device has no effect on the biochemical properties or stability of the drug product.

The VarioJect device has been developed as a platform technology by Ypsomed, Holding AG, Switzerland, an experienced supplier of prefilled pens for other indications. The device has been designed in accordance with the design control requirements of the Quality System regulation, 21 CFR Part 820.

The overall configuration of the VarioJect device and its features are depicted in FIG. 22.

FIG. 23 shows the device at the different stages of use: the device is primed, dose settings are selected by turning the plunger to the desired fixed dose, and the dose is administered by pushing the plunger.

To use the device, the user first removes the cap (FIG. 24, Step B), then primes the VarioJect by tapping the bubbles (visible though the viewing window as shown in FIG. 24, Step C) to the top of the syringe and pressing on the plunger to remove the air (FIG. 24, Step C). The user then dials the plunger to select the appropriate dose (FIG. 24, Step D). In the next step, the user presses the device against the skin at approximately a 90 degree angle, causing the needle guard to retract and the needle to be inserted into the selected SC injection site (FIG. 24, Step E), and then pushes the plunger to deliver the dose (FIG. 24, Step F). Following delivery, the user removes the device, allowing the needle guard to passively extend and lock over the needle, offering protection against accidental needle sticks (FIG. 24, Step F). After the dose is administered, the plunger locks in the down position, preventing reuse of the device.

The pen is designed to deliver between 0.10 mL to 0.45 mL in 0.05 mL increments. The requirement on dosage accuracy was established based on the *ISO* 11608-1 2012 *Needle-based injection systems for medical use, Requirements and test methods, Part 1: Needle-based injection systems, and USP* 31 *General Requirements/Injections*. The technical design requirement for delivery accuracy is that the pen must deliver the dialed dose −0.00/+0.05 mL, where 0.05 mL is the minimum increment. The needle protrusion distance of a nominal 4.5 mm limits the injection depth to subcutaneous tissue.

The device has a number of features to help ensure that it is used properly and safely. An orange priming band and white arrow indicating that the plunger should be pushed serve to remind the user that the device must be primed before use. The orange priming band disappears post-priming, indicating that this step has been completed, and the dose cannot be selected until the device has been primed. Graphics on the plunger align with the dose selection notch, clearly indicating the dose that is being selected, and detents provide tactile feedback to the user that the device is properly aligned. After dose administration, the plunger locks in the down position, and the dose that was delivered locks into the dose notch, both confirming and providing a record of the dose that was delivered. Additionally, the lock safeguards against the potential for unauthorized reuse of leftover product. When the pen is removed from the injection site, the needle guard automatically extends and locks out. This passive needle safety feature aids in reducing the potential for accidental needle sticks and also minimizes the visual exposure of the needle to some patients and caregivers who may have a fear of needles.

Development of the VarioJect

Design and development of the device were guided by *ISO* 11608-1 2012 *Needle-based injection systems for medical use, Requirements and test methods, Part 1: Needle-based injection systems* as well as *FDA Draft Guidance: Technical Considerations for Pen, Jet, and Related Injectors Intended for Use with Drugs and Biological Products*.

Testing will include bench tests ensuring accurate delivery of the drug product as well as other suitability and Human Factors studies.

Early studies have been conducted on form, features, and general usability of the device. One round of ethnographic research was conducted, in which the Sponsor observed and interviewed parents and children, where the child was taking insulin or growth hormone injections. In addition, 5 formative human factors studies including parents of pediatric subjects, caregivers, and children were conducted to test and refine the design. A draft picture-based IFU was developed and tested along with the device concepts. Results from the testing were positive, generally confirming the overall form of the selected device design and the IFU. Some design enhancements were incorporated to reduce use errors, and the updated design was retested with users. For example, the thumb rest was added to the plunger to help users understand the orientation in which the device should be held, and the flange geometry was adjusted to allow for preferred grips during use.

Future Development of the VarioJect

In preparation for clinical studies, the Sponsor has completed all verification and validation testing to assess safety, usability, and performance of the VarioJect device. Although the Sponsor does not anticipate any significant design changes to the device used for clinical studies, the Sponsor does intend to enhance the robustness of the VarioJect design based on findings during routine development efforts. During the Simulated Use Safety study, although the study successfully demonstrated the functionality of the sharps injury prevention feature of the device, it was noted that there were rare instances where select users, using very high forces exceeding typical delivery forces (>70 N), were capable of overcoming the maximum push-through forces during priming and dosing the device. Participants in the Simulated Use Study performed 26 to 33 VarioJect injections each (557 devices total among 18 participants) into a pad at a rapid rate, which is not considered representative use when injecting patients where users would take their time and excessive force would not be used. Note that this failure had not been observed previously in any of the multiple human factors studies performed with the device. The Sponsor intends to pursue minor design enhancements to further strengthen the priming and dosing end stop features by increasing the overlapping area between the contacting end stop surfaces to mitigate the risk of administering the incorrect dose to the patient.

The current specification for the priming end stop is 46 N and the specification for the dosing end stop is 69 N. The dosing end stop specification is 1.5× the priming end stop specification due to risk of an overdose resulting from failure of the dosing end stop. Verification tests of these features show that the current design exceeds the specifications by about 50% for priming and 35% for dosing. Based on results from the Simulated Use Safety study, the Sponsor is increasing the specifications and implementing minor design changes to increase the force required to push past the priming and dosing end stops. The proposed modifications will have no impact to the user interface (all forces to operate and use steps remain unchanged) and therefore, the device used clinically will be representative of the commercial device. The commercial device that includes these minor changes will be fully verified via bench testing to confirm that there is no impact to device performance and to ensure the specification has been increased and is appropriate for potential excessive force during use. Only minor changes will be made to the external features of the device. An overview of the changes is presented in FIG. 24.

External Features Accommodating the Modifications

1 Dose button will increase in diameter by 0.5-1.0 mm.
2 End cap will increase in diameter by 0.5-1.0 mm.

The improvements will increase the robustness of the device's performance while mitigating risks of incorrect dosing to the patient, without changing the user interface.

For the clinical study, appropriate training will be provided to minimize the potential for pushing past the end stop.

Suitability of the VarioJect for Pediatric Use

The injection characteristics of the VarioJect are similar in injection depth and duration to those performed by a healthcare provider using a manually injected subcutaneous hypodermic needle. Additionally, as described above, this manual injector has been designed with a number of features to help ensure that it is used properly and safely in pediatric patients and includes a passive needle safety feature. This important safety feature aids in reducing the potential for accidental needle sticks and also minimizes the exposure of the needle to some young patients who may have a fear of needles. The needle insertion depth of this device is only 4.5 mm, designed to limit the injection to subcutaneous tissue in pediatric patients. Additionally, similar to an insulin pen, this device is suitable for at-home administration by caregivers and patients, including self-administration by appropriately trained pediatric patients capable of self-administration.

An overview of the risk management activities related to in-home-use and needle length, are discussed below.

In-Home-Use

In early development of the VarioJect device, the Sponsor conducted ethnographic research in the homes of children who require injections, primarily insulin and human growth hormone. Insights were gleaned from this research that led to design improvements to help ensure safe and effective use of VarioJect in the home environment, and these improvements were subsequently confirmed to be effective in human factors studies.

Examples include:
- Clear dose labeling and detents on the dose selection knob to provide assurance of correct dose selection, a primary concern for parent caregivers
- Recording of the dose in the dose selection notch after use to allow users to confirm the correct dose was delivered
- Sequencing the use steps to allow parents to prepare the dose, then go to their child to perform the injection, a common practice for at-home injections of children
- Structuring the instructions to allow users to easily find where they are in the injection process, in case they are interrupted during the procedure In addition, risks associated with at-home injections were captured in the Application FMEA to ensure proper mitigation.

Examples include:
- Improper transportation or storage of the device by the user, or expired product, leading to degraded drug. Clear labeling was added to help ensure proper refrigeration and inspection of the product prior to use.
- Choking hazard associated with the cap. Holes were added to the cap to allow for breathing in the event of airway blockage, and warnings added to keep out of reach of children.
- Unintentional access to the device by a child. Users instructed to keep device inside package when warming to limit unintentional access.

Furthermore, an analysis was performed on the potential for abuse of the device that might occur in the home environment. Novo Nordisk Engineering, an expert on drug delivery devices used in a home setting, including insulin delivery pens prescribed for children, was hired by the Sponsor to investigate abuse potential for the VarioJect device. Analysis of different abuse scenarios was included in the Application FMEA, along with appropriate mitigations, including specifications to make it difficult for users to separate the syringe from the device or extract a second dose from the syringe.

The VarioJect and its associated instructions for use also have several safety features, as well as features to improve overall usability that facilitate in-home-use. To confirm that this device is appropriate for in-home-use in the intended population, the Sponsor will conduct a pediatric Human Factors validation study designed to evaluate in-home-use by subjects (both pediatric subjects and caregivers) considered representative of the intended user population. During the human factors validation study, all injections will be performed in a room designed to represent a home-like setting for patients and caregivers. Prescribing a self-injectable to pediatrics is a serious matter to the health care community and training is always provided as a requirement before caregivers can inject their children at home or to allow patients to self-inject. The device and IFU was developed within this context. Furthermore, the Sponsor has evaluated the injection naïve patient population in formative testing. Based on this testing, the VarioJect is considered reasonably intuitive to users. The Sponsor has taken steps to improve the design based on prior formative testing. As an example, formative testing has shown that untrained users are inclined to skip steps related to priming (ensuring proper device orientation and tapping bubbles to the top). In order to mitigate the risk of improper priming, which can cause under dosing which is classified as a low risk to users, the Sponsor has incorporated colored graphics on the device and clear step-by-step instructions. Although there has been significant focus and effort to improve the usability of the device and associated IFU, the required training has proven to be the best way to ensure proper use. As such, for the human factors study, all patients and family caregivers will be provided with representative, though minimal, training thus mimicking the real-world context in which these devices will be deployed. The Sponsor views the simulated human factors study as pivotal to demonstrating that the device is safe for in-home-use and is sufficient to address the clinical risks associated with this device. However, in order to address regulatory requirements, the Sponsor intends to conduct an actual use study on the VarioJect (in pediatric UC patients) designed to capture and document real-life VarioJect handling and use experience data from injections administered by subjects and caregivers in the home-setting, including complaints and failures in use. The actual use study is considered as additional support of the pivotal human factors data.

Needle Length

A 4.5 mm needle length was chosen for VarioJect based on published literature[1,2] pertaining to needle lengths for injecting subcutaneously in children. This needle length was chosen to account for both manufacturing tolerances on glass syringes as well as tolerances associated with assembly of the syringe in the VarioJect in order to appropriately balance the small risks of intramuscular and intradermal delivery. Based on data provided in the published literature, the risk of intramuscular injections in the 7-17 year age group is low, and although the risk of intramuscular injections is slightly higher for the 2-6 year age group, the risk is still low. Likewise, the risk of intradermal injections in the 2-6 year age group is low, and although slightly higher for the 7-17 year age group, the risk is still low. A pig biodistribution study was conducted to further evaluate the depth of injection with the VarioJect. This study demonstrated that the depth of injection using VarioJect falls within the range expected for a needle and syringe. This conclusion supports the anticipated result as depth of injection with a needle and syringe is impacted by the person administering the injection and depends on the angle of insertion and how far the needle is inserted, whereas the proposed delivery method with VarioJect would have a fixed needle insertion angle and depth. Accounting for the manufacturing dimensional variation on glass syringes as well as variation associated with assembly of the syringe in the VarioJect, the tolerance for depth of injection is ±1.25 mm. The commercially anticipated tolerance is much less as demonstrated by historical needle protrusion measurements with the SIMPONI® SmartJect autoinjector (7.4-8.6 mm) which uses the same BD Hypak syringe. Furthermore, there is generally a wide variation in syringe and needle selection and administration technique used to administer many liquid drugs subcutaneously, yet published studies have not found significant clinical concerns related to subcutaneous injection variability. And, as a class, mAbs do not appear to require precise or device-specific administration into a particular location in the subcutaneous space to be safe and effective, and small variations in PK (although not expected) are not likely to impact efficacy outcomes. Nonetheless, safety assessments will be collected as part of the proposed study.

Overview of Development Goals in Type 1 Diabetes Leading to Evaluation in "Pre-T1D"

As noted above, progression of T1D is associated with a significant impact on quality of life in early stages and eventual morbidity and mortality. To date, a number of compounds have been explored in those newly diagnosed with T1D to maintain residual beta cell function, which in turn will improve glycemic control and reduce short- and long-term complications of disease. However, the Sponsor believes there is an unmet medical need and important opportunity to delay or prevent T1D in those who are at high risk. It is well established that the autoimmune-mediated β-cell loss, was initiated many years before the clinical diagnosis. The autoimmune process that is occurring at the time of clinical diagnosis, and thus being targeted in "new onset" studies, is likely very similar to that which had been occurring in the preceding months or years, and thus agents that show (even modest) efficacy in newly diagnosed T1D can be considered as candidates to examine in those at high risk of developing T1D (ie, "Pre-T1D"). This is evidenced through the support/approval of the Agency for studies of abatacept (NCT01773707) and teplizumab (NCT01030861) in those with serologic evidence of T1D autoimmunity but has not yet met diabetes mellitus clinical criteria. In high-risk patients who can be identified to progress towards disease (ie, auto-antibody positive and dysglycemia), treating earlier to intercept or delay onset of disease may have both near and long-term benefits. In the near term, young children/adolescents may avoid the requirement of multiple daily injections of exogenous insulin. Further, it is expected that patients diagnosed with T1D at younger ages may have more aggressive disease. Therefore, delaying onset by 2 or more years may avoid more rapid progression of β-cell destruction. In the long-term, early preservation of β-cell mass and good glycemic control may mitigate severe complications later in life such as cardiovascular disease or hospitalization which are associated with significant morbidity and mortality, and socioeconomic burden.

As the Sponsor believes there is a continuum of disease progression in T1D, if positive results are observed in the trial outlined herein, in addition to consideration for developing as a therapy in new-onset disease, the Sponsor would anticipate further evaluation in T1D pre-disease or "interception". The Sponsor considers that children/adolescent patients 6 to 21 years of age with ≥2 auto-antibodies for T1D with dysglycemia who are not yet insulin dependent are patients greatest at-risk for progression to clinical disease and would most benefit from treatment in the pre-disease state. The Sponsor proposes to take a staged approach in determining whether golimumab is an effective treatment that provides benefit in the target population described above.

The Sponsor's first step in the staged approach is to establish the benefit-risk of golimumab in new onset T1D study described in this Briefing Document. The results of this study will provide key information on the effect of golimumab on preservation of β-cell mass as well as the safety profile in this patient population. In the early planning stages of a pilot study in 6 to 21 year olds who have not yet met the formal clinical diagnosis of T1D but who have a first degree relative with T1D, and are double auto-antibody positive for T1D with slightly elevated HbA1c (ie, 5.6 to 6.4%). The goal of this pilot study is to obtain early safety and efficacy information to establish the mechanism of benefit with golimumab in the pre-disease state. This trial would start after the study in new-onset individuals discussed above. These two initial studies will be complementary and provide key data to inform planning for a larger, more formal, "proof-of-concept" clinical trial in those at high risk for developing T1D study to assess the benefit-risk of treatment with golimumab in the target pre-T1D population.

The Sponsor intends to communicate the results from these two initial studies in the context of preparations for the proof-of-concept study in those at risk for T1D to align with the Agency on a robust development plan for golimumab in the treatment of pre-T1D.

TABLE 8

Studies in Support of the Simponi Pediatric Presentations
Cross-reference will be made to data previously submitted as this presentation is
already approved for use in adults.

A - VarioJect Actual Use Study

Study:
VarioJect Actual Use Study (includes assessment of labeling comprehension, safety, and device durability/robustness). This study will be conducted as a substudy of CNTO148UCO1002 which will be conducted to provide PK data in pediatric with body weight <45 kg to support an extrapolation based approach to the pediatric UC indication, and to demonstrate that the VarioJect device can achieve the expected drug exposure in the intended pediatric population.
Objectives:
To provide supportive data that the VarioJect as designed, together with the appropriate training and written Instructions for Use, is suitable for at-home administration by subjects or their caregivers. To provide supportive safety data TABLE 8-continued Studies in Support of the Simponi Pediatric Presentations
Cross-reference will be made to data previously submitted as this presentation is already approved for use in adults.

demonstrating that the VarioJect is suitable for use in the pediatric patient population. To provide supportive VarioJect durability and robustness data.
Description:
All study participants performing the injection will be asked to complete a questionnaire regarding their experience using the VarioJect following the second at-home administration. All device complaints and device-related AEs will be captured and investigated including the return of the device for inspection. A visual assessment of a random sampling of approximately 50-100 used VarioJect devices will be performed to assess device durability and robustness.
Comments:
Study and questionnaire are designed to capture and document real-life VarioJect handling and use experience data from injections administered by subjects and caregivers in the home-setting, including complaints and failures in use.

B - PFS-U Actual Use Study

Study:
PFS-U Actual Use Study (includes assessment of labeling comprehension and safety). This study will be conducted as a substudy of CNTO0148UCO1002.
Objectives:
To provide supportive data that the PFS-U as designed, together with the appropriate training and written Instructions for Use, is suitable for at-home administration by pediatric subjects or their caregivers. To provide supportive safety data demonstrating that the PFS-U is suitable for use in the pediatric patient population.
Description:
All study participants performing the injection will be asked to complete a questionnaire regarding their experience using the PFS-U following the second at-home administration. All device complaints and device-related AEs will be captured and investigated including the return of the device for inspection.
Comments:
Study and questionnaire are designed to capture and document real-life PFS-U handling and use experience data from injections administered by subjects and caregivers in the home-setting, including complaints and failures in use.

C - Pediatric Summative Human Factors Study

Study:
Pediatric Summative Human Factors (includes assessment of label comprehension)
Objectives:
The objectives of this study are to provide pivotal device usability data indicating that the VarioJect and PFS-U can be used safely in the intended population (by caregivers, Health Care Professionals [HCP], or self-administration) under realistic conditions and to validate the device instructions for use.
Description:
Simulated device use study in the target population, in a representative use environment conducted by human factors experts, as guided by FDA guidance: *Applying Human Factors and Usability Engineering to Medical Devices to Optimize Safety and Effectiveness in Design* (2011). In this study, approximately 45 subjects will be divided into 3 groups. Group 1 will be a mix of family caregivers and HCP (VarioJect injection). Group 2 will be pediatric subjects capable of self-injection (VarioJect injection). Group 3 will be pediatric subjects capable of self-injection (PFS-U injection). Overall performance success is achieved when the user delivers the complete dose without making any use errors that could result in serious harm. The proposed study assigns pass/fail criteria at the individual task level, and behaviors such as errors, close calls, and/or difficulties will be recorded at the individual task level. Subjective participant feedback will be collected in narrative form, and participants will be asked open-ended questions about the procedure and device design. Participants will be asked probe questions to evaluate their knowledge and understanding of the instructions provided in the IFU.
Comments:
Protocol, along with the instructions for use, has been submitted to the FDA for review and comment (eCTD IND 100181; Sequence No. 0307). Included with this submission was a summary of the use errors seen thus far in formative studies and a discussion of how these studies informed product design and labeling. The results of this human factors study will be summarized in the sBLA, along with the final HFS report, and is intended to support the registration of the new VarioJect and to extend the use of the PFS-U for pediatric use.

D - VarioJect Performance Testing

Study:
1.) Verification testing
2.) Functional stability testing
3.) Accelerated and real-time aging of device components
4.) Assembly process validation

TABLE 8-continued

Studies in Support of the Simponi Pediatric Presentations
Cross-reference will be made to data previously submitted as this presentation is already approved for use in adults.

5.) Simulated use (safety) study
6.) Biocompatibility testing
7.) Shipping testing
8.) Biochemical testing following VarioJect delivery
Objectives:
The objective of these studies is to demonstrate that the VarioJect device meets its design requirements.
Description:
1. Verification testing is conducted according to the following.
   ISO 11608:2012 *Needle-based injection systems for medical use - Requirements and test methods.* VarioJect is designated D2-integrated, single dose, non-replaceable container, whereby a portion of the deliverable volume is expelled.
   FDA Draft Guidance *Technical Considerations for Pen, Jet, and Related Injectors Intended for Use with Drugs and Biological Products.*
Key elements of the development and test program include:
   Design and verification that doses selected and dialed meet accuracy criteria throughout the shelf life of the product
   Design and verification that needle extension is limited and appropriate for subcutaneous administration
   Verification of design and manufacturing durability in expected use
   Verification that device safety features intended to protect against accidental needle sticks operate reliably
2. Functional stability testing evaluates aging of the drug-device combination product followed by device testing to ensure device functionality. The assembled product is stored at the recommended temperature of 2-8° C., as well as accelerated (25° C.) conditions.
3. For accelerated aging testing, device sub-assemblies are exposed to elevated temperature aging followed by assembly with the drug-filled PFS and device testing to ensure device functionality. The accelerated aging data is supported by real time aging testing of device sub-assemblies stored at room temperature.
4. Assembly process validation involves assembly of drug-device combination product using equipment that will be used to assemble the VarioJect for commercial launch, followed by device testing.
5. The simulated use (safety) study will include 500+ mock injections demonstrating successful operation of needle safety feature following ISO 23908:2011 *Sharps injury protection - Requirements and test methods - Sharps protection features for single-use hypodermic needles, introducers for catheters and needles used for blood sampling* and *Guidance for Industry and FDA Staff: Medical Devices with Sharps Injury Prevention Features.*
6. Biocompatibility testing is performed in accordance with ISO-10993-1:2009 *Biological evaluation of medical devices - Part 1: Evaluation and testing within a risk management process* for skin contacting surface device having limited contact duration (≤24 hours).
7. Shipping testing is performed in accordance with ASTM D4169: Standard Practice for Performance Testing of Shipping Containers and Systems, and includes an assessment of container closure integrity.
8. Biochemical testing following VarioJect delivery is conducted to determine if the shear forces on SIMPONI generated during delivery through the VarioJect had an adverse effect on the biochemical attributes of SIMPONI.

Abbreviations FDA = Food and Drug Administration; HCP = Health Care Professional; HFS = Human Factors Study; IFU = Instructions for use; PFS = prefilled syringe; PFS-U = prefilled syringe in the UltraSafe Passive ® needle guard; PK = pharmacokinetic(s); sBLA = Supplemental Biologics License Application; UC = ulcerative colitis.

TABLE 9

Dose chart for study CNTO148DML2001 in pediatric subjects with Type 1 Diabetes with body weight <45

First Induction Dose (at Week 0)
Dose (mg) from VarioJect and/or PFS-U
Body weight rounded to the nearest 5 kg and height rounded to the nearest 10 cm
See device selection table for additional administration instructions

| Height (cm) | Weight (kg) | | | | | | | |
|---|---|---|---|---|---|---|---|---|
| | 10 | 15 | 20 | 25 | 30 | 35 | 40 | 45 |
| 70 | 55 | 65 | 75 | 85 | | | | |
| 80 | 55 | 70 | 80 | 90 | | | | |
| 90 | 60 | 75 | 85 | 95 | 105 | 105 | | |
| 100 | 65 | 75 | 90 | 100 | 110 | 110 | 125 | 200 |
| 110 | 65 | 80 | 95 | 105 | 115 | 115 | 135 | 200 |
| 120 | 70 | 85 | 100 | 110 | 120 | 120 | 140 | 200 |
| 130 | | 90 | 100 | 115 | 125 | 125 | 145 | 200 |
| 140 | | 90 | 105 | 120 | 130 | 130 | 150 | 200 |
| 150 | | | 110 | 120 | 135 | 135 | 155 | 200 |
| 160 | | | 115 | 125 | 140 | 140 | 160 | 200 |
| 170 | | | | 130 | 145 | 145 | 165 | 200 |
| 180 | | | | | 145 | 145 | 170 | 200 |

TABLE 9-continued

Dose chart for study CNTO148DML2001 in pediatric subjects with Type 1 Diabetes with body weight <45

Second Induction Dose (at Week 2) and Maintenance Dose (q4w)
Dose (mg) from VarioJect and/or PFS-U
Body weight rounded to the nearest 5 kg and height rounded to the nearest 10 cm
See device selection table for additional administration instructions

| Height | Weight (kg) | | | | | | | |
|---|---|---|---|---|---|---|---|---|
| (cm) | 10 | 15 | 20 | 25 | 30 | 35 | 40 | 45 |
| 70 | 25 | 30 | 35 | 40 | | | | |
| 80 | 30 | 35 | 40 | 45 | | | | |
| 90 | 30 | 35 | 40 | 45 | 50 | 55 | | |
| 100 | 30 | 40 | 45 | 50 | 55 | 60 | 65 | 100 |
| 110 | 35 | 40 | 45 | 50 | 55 | 60 | 65 | 100 |
| 120 | 35 | 40 | 50 | 55 | 60 | 65 | 70 | 100 |
| 130 | | 45 | 50 | 55 | 60 | 65 | 70 | 100 |
| 140 | | 45 | 55 | 60 | 65 | 70 | 75 | 100 |
| 150 | | | 55 | 60 | 65 | 70 | 75 | 100 |
| 160 | | | 55 | 65 | 70 | 75 | 80 | 100 |
| 170 | | | | 65 | 70 | 75 | 80 | 100 |
| 180 | | | | | 75 | 80 | 85 | 100 |

| Device selection | |
|---|---|
| DOSE (mg) | DEVICES[a] |
| 25 | 1 VarioJect* |
| 30 | 1 VarioJect* |
| 35 | 1 VarioJect* |
| 40 | 1 VarioJect* |
| 45 | 1 VarioJect* |
| 50 | 1 PFS-U-50** |
| 55 | 2 VarioJect* |
| 60 | 2 VarioJect* |
| 65 | 2 VarioJect* |
| 70 | 2 VarioJect* |
| 75 | 2 VarioJect* |
| 80 | 2 VarioJect* |
| 85 | 2 VarioJect* |
| 90 | 2 VarioJect* |
| 95 | 1 PFS-U-50, 1 VarioJect*** |
| 100 | 1 PFS-U-100** |
| 105 | 1 PFS-U-50, 2 VarioJect*** |
| 110 | 1 PFS-U-100, 1 VarioJect*** |
| 115 | 1 PFS-U-100, 1 VarioJect*** |
| 120 | 1 PFS-U-100, 1 VarioJect*** |
| 125 | 1 PFS-U-100, 1 VarioJect*** |
| 130 | 1 PFS-U-100, 1 VarioJect*** |
| 135 | 1 PFS-U-100, 1 VarioJect*** |
| 140 | 1 PFS-U-100, 1 VarioJect*** |
| 145 | 1 PFS-U-100, 1 VarioJect*** |
| 150 | 1 PFS-U-100, 1 PFS-U-50** |
| 155 | 1 PFS-U-100, 2 VarioJect*** |
| 160 | 1 PFS-U-100, 1 PFS-U-50, 1 VarioJect*** |
| 165 | 1 PFS-U-100, 1 PFS-U-50, 1 VarioJect*** |
| 170 | 1 PFS-U-100, 1 PFS-U-50, 1 VarioJect*** |
| 175 | 1 PFS-U-100, 1 PFS-U-50, 1 VarioJect*** |
| 180 | 1 PFS-U-100, 1 PFS-U-50, 1 VarioJect*** |

KEY
*VarioJect Only
**PFS-U Only
***Combinations of VarioJect and PFS-U
[a]The VarioJect is designed to administer SC doses of golimumab in 5 mg increments from 10 mg to 45 mg.

Regulatory Considerations

Plans to Open IND for T1D

The Sponsor is planning to open an IND for the study of golimumab for the treatment of T1D by 2Q 2016. SIMPONI® has been approved in the US for the treatment of Rheumatoid Arthritis, Psoriatic Arthritis, Ankylosing Spondylitis and Ulcerative Colitis.

The Sponsor has the following active BLAs with the Division of Pulmonary, Allergy, and Rheumatology Products (DPARP) or the Division of Gastroenterology and In-Born Error Products DGIEP).

BLA125289: For golimumab (SIMPONI®) approved on 24 Apr. 2009 with the following indications:
  SIMPONI®, in combination with methotrexate, is indicated for the treatment of adult patients with moderately to severely active rheumatoid arthritis.
  SIMPONI®, alone or in combination with methotrexate, is indicated for the treatment of adult patients with active psoriatic arthritis.
  SIMPONI® is indicated for the treatment of adult patients with active ankylosing spondylitis.
  SIMPONI® is indicated in adult patients with moderately to severely active ulcerative colitis who have demonstrated corticosteroid dependence or who have had an inadequate response to or failed to tolerate oral aminosalicylates, oral corticosteroids, azathioprine, or 6-mercaptopurine for:
    inducing and maintaining clinical response
    improving endoscopic appearance of the mucosa during induction
    inducing clinical remission
    achieving and sustaining clinical remission in induction responders The Sponsor has 4 active INDs in support of the golimumab development program with DPARP or DGIEP
  IND 09925 for the study of CNTO148 (golimumab) for the treatment of moderately to severely active rheumatoid arthritis (including polyarticular JIA)
  IND 12723 for the study of CNTO148 (golimumab) for the treatment of active psoriatic arthritis
  IND 12729 for the study of CNTO148 (golimumab) for the treatment of active ankylosing spondylitis
  IND 100181 for the study of CNTO148 (golimumab) for the treatment of ulcerative colitis (including pediatric UC)

As noted in the IND requirements table below (Table 10), the Sponsor proposes to either submit items to the new IND or cross-refer to IND 09925 or BLA125289. These will be text cross-references only (no electronic hyperlinks).

TABLE 10

IND requirements Table

| IND Requirement | IND/BLA Reference |
|---|---|
| Introductory Statement and General Investigational Plan [21 CR 312.23(a)(3)] | To be included in new IND |

TABLE 10-continued

IND requirements Table

| IND Requirement | IND/BLA Reference |
| --- | --- |
| Investigator's Brochure [21 CFR 312.23(a)(5)] | To be included in new IND |
| Protocols [21 CFR 312.23(a)(6)1 | To be included in new IND |
| Chemistry, Manufacturing, and Control Information [21 CFR 312.23(a)(7)] | |
| 1. Chemistry and Manufacturing Introduction | To be included in new IND |
| 2. Drug Substance [21 CFR 312.23(a)(7)(iv)(a)] | Cross-reference to IND 09925 |
| 3. Drug Product [21 CFR 312.23 (a)(7)(iv)(b)] | Cross-reference to IND 09925 or IND 100181 and if applicable, include new and unique information to clinical trials conducted under the new IND |
| 4. A brief general description of the composition, manufacture, and control of any placebo to be used in the proposed clinical trial(s) [21 CFR 312.23(a)(7)(iv)(c)] | Cross-reference to IND 09925 or IND 100181 and if applicable, include new and unique information to clinical trials conducted under the new IND |
| 5. a copy of all labels and labeling to be provided to each investigator [21 CFR 312.23(a)(7)(iv)(d)] | To be included in the new IND |
| Pharmacology and Toxicology Information [21 CFR 312.23(a)(8)] | |
| 1. Pharmacology and Drug Distribution [21 CFR 312.23(a)(8)(i)] | Cross reference to BLA 125289 |
| 2. Toxicology: Integrated Summary [21 CFR 312.23(a)(8)(ii)(a)] | Cross reference to BLA 125289 |
| 3. Toxicology: Full Data Tabulation [21 CFR 312.23(a)(8)(ii)(b)] | Cross reference to BLA 125289 |
| 4. Toxicology: GLP Certification [21 CFR 312.23(a)(8)(iii)] | Cross reference to BLA 125289 |
| Previous Human Experience with the Investigational Drug [21 CFR 312.23(a)(9)] | Cross reference to BLA 125289 |
| 21 CFR 312.23(a)(10) | |
| (i) Drug dependence and abuse potential | Cross-reference to BLA 125289 |
| (ii) Radioactive drugs | N/A |
| (iii) Pediatric studies | Status of pediatric program to be included in new IND |

It will be clear that the invention can be practiced otherwise than as particularly described in the foregoing description and examples.

Numerous modifications and variations of the present invention are possible in light of the above teachings and, therefore, are within the scope of the appended claims.

What is claimed is:

1. A method for treating pre-Type 1 Diabetes (pre-T1D) in a human subject, wherein the subject is 6 to 21 years of age and has ≥2 auto-antibodies for T1D, and wherein said pre-T1D is prior to onset of symptoms and requirement for exogenous insulin, the method comprising administering to the subject an anti-TNF antibody comprising:
   a. a heavy chain (HC) complementary determining region (CDR) 1 comprising an amino acid sequence of SEQ ID NO: 1;
   b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
   c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
   d. a light chain (LC) CDR1 comprising an amino acid sequence of SEQ ID NO: 4; wherein position 7 of SEQ ID NO: 4 is tyrosine;
   e. a LC CDR2 comprising an amino acid sequence of SEQ ID NO: 5; and
   f. a LC CDR3 comprising an amino acid sequence of SEQ ID NO: 6;
   wherein said anti-TNF antibody is administered with a medical device suitable for self-administration, and wherein the device is a prefilled syringe with an ULTRASAFE PASSIVE® (needle guard) if the subject weighs ≥45 kg and VARIOJECT™ (injector) if the subject weighs <45 kg.

2. The method according to claim 1, wherein the device is the VARIOJECT™ (injector) with a 4.5 mm needle length.

3. A method for treating pre-Type 1 Diabetes (pre-T1D) in a human subject, wherein the subject is 6 to 21 years of age and has ≥2 auto-antibodies for T1D, and wherein said pre-T1D is prior to onset of symptoms and requirement for exogenous insulin, the method comprising administering to the subject a composition comprising an anti-TNF antibody comprising:
   a. a heavy chain (HC) complementary determining region (CDR) 1 comprising an amino acid sequence of SEQ ID NO: 1;
   b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
   c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
   d. a light chain (LC) CDR1 comprising an amino acid sequence of SEQ ID NO: 4; wherein position 7 of SEQ ID NO: 4 is tyrosine;
   e. a LC CDR2 comprising an amino acid sequence of SEQ ID NO: 5; and
   f. a LC CDR3 comprising an amino acid sequence of SEQ ID NO: 6;
   wherein said composition is administered with a medical device suitable for self-administration, and wherein the device is a prefilled syringe with an ULTRASAFE PASSIVE® (needle guard) if the subject weighs ≥45 kg and VARIOJECT™ (injector) if the subject weighs <45 kg.

4. The method according to claim 3, wherein the device is the VARIOJECT™ (injector) with a 4.5 mm needle length.

5. A method for treating pre-Type I Diabetes (pre-T1D) in a human subject, wherein the subject is 6 to 21 years of age and has ≥2 auto-antibodies for T1D, and wherein said pre-T1D is prior to onset of symptoms and requirement for exogenous insulin, the method comprising using a medical device to administer a composition comprising at least one isolated mammalian anti-TNF antibody comprising:

a. a heavy chain (HC) complementary determining region (CDR) 1 comprising an amino acid sequence of SEQ ID NO: 1;
b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
d. a light chain (LC) CDR1 comprising an amino acid sequence of SEQ ID NO: 4; wherein position 7 of SEQ ID NO: 4 is tyrosine;
e. a LC CDR2 comprising an amino acid sequence of SEQ ID NO: 5; and
f. a LC CDR3 comprising an amino acid sequence of SEQ ID NO: 6;
wherein said device is suitable for subcutaneously (SC) administering said composition comprising at least one anti-TNF antibody.

6. The method according to claim 4, wherein the device is suitable for self-administration and the device is selected from the group consisting of: prefilled syringe, prefilled syringe with an ULTRASAFE PASSIVE® (needle guard), and a VARIOJECT™ (injector).

7. The method according to claim 5, wherein the device is the VARIOJECT™ (injector) with a 4.5 mm needle length.

8. A method for treating pre-Type 1 Diabetes (pre-T1D) in a human subject, wherein the subject is about 6 to 21 years of age and has about ≥2 auto-antibodies for T1D, wherein said pre-T1D is prior to onset of symptoms and requirement for exogenous insulin, the method comprising administering to the subject an anti-TNF antibody comprising:
a. a heavy chain (HC) complementary determining region (CDR) 1 comprising an amino acid sequence of SEQ ID NO: 1;
b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
d. a light chain (LC) CDR1 comprising an amino acid sequence of SEQ ID NO: 4; wherein position 7 of SEQ ID NO: 4 is tyrosine;
e. a LC CDR2 comprising an amino acid sequence of SEQ ID NO: 5; and
f. a LC CDR3 comprising an amino acid sequence of SEQ ID NO: 6.

* * * * *